United States Patent
Gozin et al.

(10) Patent No.: US 10,774,171 B2
(45) Date of Patent: *Sep. 15, 2020

(54) ENERGETIC COMPOUNDS AND COMPOSITIONS

(71) Applicant: Technology Innovation Momentum Fund (Israel) Limited Partnership, Tel-Aviv (IL)

(72) Inventors: Michael Gozin, Tel-Aviv (IL); Alex Aizikovich, Rehovot (IL); Avital Shlomovich, Natania (IL); Adva Cohen, Rishon-LeZion (IL); Tali Pechersky, Ashdod (IL)

(73) Assignee: Technology Innovation Momentum Fund (Israel) Limited Partnership, Tel-Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/199,313

(22) Filed: Nov. 26, 2018

(65) Prior Publication Data

US 2019/0092895 A1 Mar. 28, 2019

Related U.S. Application Data

(63) Continuation of application No. 15/515,209, filed as application No. PCT/IL2015/051057 on Oct. 28, 2015, now Pat. No. 10,196,477.

(30) Foreign Application Priority Data

Oct. 30, 2014 (IL) .......................................... 235415

(51) Int. Cl.
| | |
|---|---|
| C07D 257/02 | (2006.01) |
| C07D 403/04 | (2006.01) |
| C07D 403/06 | (2006.01) |
| C07D 403/14 | (2006.01) |
| C07F 7/08 | (2006.01) |
| C08G 18/61 | (2006.01) |
| C08G 18/73 | (2006.01) |
| C08G 18/38 | (2006.01) |
| C07D 487/18 | (2006.01) |
| C07D 487/22 | (2006.01) |

(52) U.S. Cl.
CPC ....... *C08G 18/3851* (2013.01); *C07D 257/02* (2013.01); *C07D 403/04* (2013.01); *C07D 403/06* (2013.01); *C07D 403/14* (2013.01); *C07D 487/18* (2013.01); *C07D 487/22* (2013.01); *C07F 7/08* (2013.01); *C08G 18/61* (2013.01); *C08G 18/73* (2013.01)

(58) Field of Classification Search
CPC .. C07D 257/02; C07D 403/04; C07D 403/06; C07D 403/14; C07F 7/08; C08G 18/73
USPC ................ 544/179, 182, 183; 514/182, 183; 149/122
See application file for complete search history.

(56) References Cited

U.S. PATENT DOCUMENTS

| | | |
|---|---|---|
| 3,375,230 A | 3/1968 | Oja et al. |
| 5,139,588 A | 8/1992 | Poole |
| 5,397,075 A | 3/1995 | Behr et al. |
| 5,501,823 A | 3/1996 | Lund et al. |
| 5,531,941 A | 7/1996 | Poole |
| 5,545,272 A | 8/1996 | Poole et al. |
| 5,589,662 A | 12/1996 | Schleicher et al. |
| 5,610,444 A | 3/1997 | Austruy et al. |
| 5,622,380 A | 4/1997 | Khandhadia et al. |
| 5,628,528 A | 5/1997 | DeSautelle et al. |
| 5,700,532 A | 12/1997 | Chiou |
| 5,727,813 A | 3/1998 | Stratton et al. |
| 5,756,929 A | 5/1998 | Lundstrom et al. |
| 5,783,773 A | 7/1998 | Poole |
| 5,806,888 A | 9/1998 | Adamini |
| 5,872,329 A | 2/1999 | Burns et al. |
| 5,899,399 A | 5/1999 | Brown et al. |
| 6,074,502 A | 6/2000 | Burns et al. |
| 6,077,371 A | 6/2000 | Lundstrom et al. |
| 6,552,051 B2 | 4/2003 | Bottaro et al. |
| 6,620,266 B1 | 9/2003 | Williams et al. |
| 7,776,169 B2 | 8/2010 | Miller et al. |
| 8,580,054 B2 | 11/2013 | Pagoria et al. |
| 8,608,196 B2 | 12/2013 | Quioc et al. |
| 10,196,477 B2 * | 2/2019 | Gozin .................. C07D 257/02 |
| 2017/0226270 A1 | 8/2017 | Gozin et al. |

FOREIGN PATENT DOCUMENTS

| | | |
|---|---|---|
| DE | 102011118462 | 5/2013 |
| RU | 2261873 | 10/2005 |

(Continued)

OTHER PUBLICATIONS

Communication Pursuant to Article 94(3) EPC dated Mar. 8, 2019 From the European Patent Office Re. Application No. 15855730.6. (4 Pages).

(Continued)

*Primary Examiner* — Venkataraman Balasubramanian

(57) ABSTRACT

Energetic nitrogen-rich monomers represented by the general Formula I:

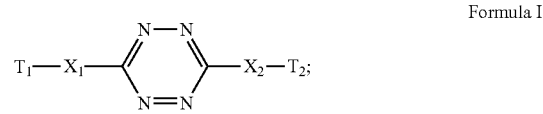

Formula I wherein each of X1 and X2 is independently NR or a covalent bond, R is H or C1-4 alkyl, each of T1 and T2 is independently a moiety selected from the group consisting of a triazole moiety, a tetrazole moiety and a guanidine moiety, at least one of T1 and T2 being substituted by at least one polymerizable group, are disclosed herein, as well as polymers based thereon, and uses of such polymers.

16 Claims, 2 Drawing Sheets

(56) References Cited

FOREIGN PATENT DOCUMENTS

| WO | WO 98/54113 | 12/1998 |
|---|---|---|
| WO | WO 2012/172176 | 12/2012 |
| WO | WO 2016/067292 | 5/2016 |

OTHER PUBLICATIONS

Translation Dated Mar. 14, 2019 of Notification of Office Action dated Feb. 28, 2019 From the State Intellectual Property Office of the People's Republic of China Re. Application No. 201580058321.X. (2 Pages).
International Preliminary Report on Patentability dated May 11, 2017 From the International Bureau of WIPO Re. Application No. PCT/IL2015/051057. (10 Pages).
International Search Report and the Written Opinion dated Jan. 25, 2016 From the International Searching Authority Re. Application No. PCT/IL2015/051057.
Official Action dated Jul. 10, 2018 From the US Patent and Trademark Office Re. U.S. Appl. No. 15/515,209. (18 pages).
Restriction Official Action dated Feb. 23, 2018 From the US Patent and Trademark Office Re. U.S. Appl. No. 15/515,209. (8 pages).
Supplementary European Search Report and the European Search Opinion dated Mar. 20, 2018 From the European Patent Office Re. Application No. 15855730.6. (10 Pages).
Babad et al. "The Chemistry of Phosgene", Chemical Reviews, 73(1): 75-91, 1973.
Betzler et al. "Synthesis of Glycidyl-5-(Carboxyethyl-1H-Tetrazole)Polymer and 1,2-Bis(5-Carboxyethyl-1H-Tetrazolyl)Ethane as Polymeric Precursor", European Journal of Organic Chemistry, 2013(3): 509-514, 2013.
Binder et al. "Surface-Modified Nanoparticles Via Thermal and Cu(I)-Mediated 'Click' Chemistry: Generation of Luminescent CdSe Nanoparticles With Polar Ligands Guiding Supramolecular Recognition", Journal of Materials Chemistry, 17: 2125-2132, Advance Article Mar. 6, 2007.
Bussels et al. "Multiblock Copolymers Synthesized by Miniemulsion Polymerization Using Multifunctional RAFT Agents", Macromolecules, 37(25): 9299-9301, Dec. 2004.
Chavez et al. "3,3'-Azobis(6-amino-1,2,4,5-Tetrazine): A Novel High-Nitrogen Energetic Material", Angewandte Chemie International Edition, 39(10): 1791-1793, 2000.
Clavier et al. "S-Tetrazines as Building Blocks for New Functional Molecules and Molecular Materials", Chemical Review, 110: 3299-3314, Mar. 22, 2010.
Ding et al. "Synthesis, Characterization and Photovoltaic Applications of a Low Band Gap Polymer Based on S-Tetrazine and Dithienosilole", Chemical Communication, 46(45): 8668-8670, Published Online Oct. 18, 2010. Scheme 1, 2.
Dippold "Nitrogen-Rich Energetic Materials Based on 1,2,4-Triazole Derivatives", Dissertation zur Erlangung des Doktorgrades der Fakultaet fuer Chemie and Pharmazie der Ludwig-Maximilians-Universitaet Muenchen, Germany, p. 1-273, Aug. 1, 2013.
Fu et al. "Synthesis and Characteristics of a Novel, High-Nitrogen, Heat-Resistant, Insensitive Material (NOG2Tz)", Journal of Materials Chemistry, 22: 60-63, 2012.
Fu et al. "Synthesis and Characteristics of Novel, High-Nitrogen 1,2,4-Oxadiazoles", Royal Society of Chemistry, RSC Advances, 4: 11859-11861, 2014.
Ghule et al. "Quantum-Chemical Investigation of Substituted S-Tetrazine Derivatives as Energetic Materials", Bulletin of the Korean Chemical Society, 33(2): 564-570, 2012. Figs.1-3, Table 1, Conclusions.
Gromadzki et al. "Morphology of Polystyrene-Block-Poly(Styrene-Co-Acrylonitrile) and Polystyrene-Block-Poly(Styrene-Co-Acrylonitrile-Co-5-Vinyltetrazole) Diblock Copolymers Prepared by Nitroxide-Mediated Radical Polymerization and 'Click' Chemistry", European Polymer Journal, 44: 189-199, Available Online Nov. 13, 2007.
Hiskey et al. "Insensitive High-Nitrogen Compounds", NTIS, No. DE-2001-776133, LA-UR-01-1493, 10 P., 2001.
Kizhnyaev et al. "Branched Tetrazole-Containing Polymers", Polymer Science, Series A, 49(1): 28-34, 2007.
Kizhnyaev et al. "Synthesis and Properties of Tetrazole-Containing Oligomers", Polymers Science, Series B, 53(5-6): 317-323, 2011.
Kizhnyaev et al. "Synthesis of Energetic Polynuclear and Polymeric Nitroazole Systems", Russian Journal of Applied Chemistry, 82(10): 1769-1775, 2009.
Klapoetke et al. "Investigation of Nitrogen-Rich Enegetic Polymers Based on Alkylbridged Bis-(1-Methyl-Tetrazolylhydrazines)", Journal of Polymer Science, Part A: Polymer Chemistry, 48: 122-127, 2010.
Klapoetke et al. "Nitrogen-Rich Polymers Based on 5-Bromo-1-Vinyl-1H-Tetrazole", European Journal of Organic Chemistry, 2010: 1169-1175, 2010.
Klapoetke et al. "Thermally Stable 3,6-Disubstituted 1,2,4,5-Tetrazines", Zeitschrift fur Naturforschung B, XP055456186, 68(12): 1310-1320, Dec. 1, 2013. Scheme 2, Compounds (7), (8) and (9); p. 1310, col. 2, Para. 2.
Klapotke et al. "Investigation of Nitrogen-Rich Energetic Polymers Based on Alkylbridged bis-(1-Methyl-Tetrazolylhydrazines)", Journal of Polymer Science, Part A: Polymer Chemistry, 48 (1): 122-127, Nov. 24, 2009. Scheme 3, Conclusions;Table 3.
Lee et al. "An Improved Synthesis of 5-Amino-3-Nitro-1H-1,2,4-Triazole (ANTA), A Useful Intermediate for the Preparation of Insensitive High Explosives", Journal of Energetic Materials, 9(5): 415-428, 1991.
Pagoria et al. "A Review of Energetic Materials Synthesis", Thermochimica Acta, 384: 187-204, 2002.
Pasquinet "Nitrogen-Rich Polymers as Candidates for Energetic Applications", New Polymers for Special Applications, INTECH, Chap.10: 313-338, 2012.
Provatas "Energetic Polymers and Plasticisers for Explosive Fomulations—Review of Recent Advances", Defense Science & Technology Organisation, Department of Defense, DSTO-TR-0966, p. 1-37, Apr. 2000.
Qi et al. "A Novel Stable High-Nitrogen Energetic Material: 4,4'-Azobis(1,2,4-Traizole)", Journal of Materials Chemistry, 21: 3221-3225, 2011.
Qin et al. "Click Polymerization: Progress, Chellenges, and Opportunities", Macromolecules, 43: 8693-8702, Sep. 28, 2010.
Rudakov et al. "Synthesis and Properties of Alkylnitramino-1,2,4,5-Tetrazines", Chemistry of Heterocyclic Compounds, 50(1): 53-64, Apr. 2014.
Saikia et al. "Synthesis and Characterization of 3,6-Bis(1H-1,2,3,4-Tetrazol-5-Ylamino)-1,2,4,5-Tetrazine(BTATz): Novel High-Nitrogen Content Insensitive High Energy Material", Journal of Hazardous Materials, 170(1): 306-313, Available Online May 3, 2009. p. 307, Scheme 2.
Sayed et al. "1,2-Dipolar Cycloaddition Polymerization Reactions of Novel Macromolecules Containing Sym-Tetrazine Rings", Polymer, 49: 2253-2259, Available Online Feb. 29, 2008.
Sayed et al. "Synthesis of High Metal-Complexation Linear Elastomers Containing Sym-1,2,4,5-Tetrazine Rings", Journal of Applied Polymer Science, 114: 3915-3922, Published Online Aug. 19, 2009.
Sheremetev et al. "A mild and Efficient Synthesis of 3-Hetarylamino-S-Tetrazines", Mendeleev Communications, 22: 302-304, 2012.
Shin et al. "Synthesis of Polymers Including Both Triazole and Tetrazole by Click Reaction", Bulletin of the Korean Chemical Society, 32(2): 547-552, 2011.
Sproll "Investigation of nitrogen-Rich Polymers Based on Tetrazoles and Triazoles", Dissertation zur Erlangung des Doktorgrades der Fakultaet fuer Chemie and Pharmazie der Ludwig-Maximilians-Universitaet Muenchen, Germany, p. 317, Nov. 24, 2009.
Terao et al. "Synthesis d an Insulated Molecular Wire by Click Polymerization", Chemical Communications, 48: 1577-1579, 2012.
Tian et al. "Preparation and Properties of a New Polytriazole Resin Made From Dialkyne and Triazide Compounds and Its Composite", Polymer Bulletin, 60: 457-465, 2008.
Wei et al. "Molecular Design of 1,2,4,5-Tetrazine-Based High-Energy Density Materials", Journal of Physical Chemistry A, 113: 9404-9412, Jul. 30, 2009.
Xue et al. "Energetic Polymer Salts From 1-Vinyl-1,2,4-Triazole Derivatives", Journal of Polymer Science, Part A: Polymer Science, 46: 2414-2421, 2008.

(56) References Cited

OTHER PUBLICATIONS

Zhou "Synthesis of New Tetrazines Functionalized With Photoactive and Electroactive Groups",Thesis of Doctorat, Ecole Normale Superieure de Cachan, France, p. 3-262, Jul. 20, 2012. p. 51, Ex.73-74.

Notification of Office Action and Search Report dated Feb. 28, 2019 From the State Intellectual Property Office of the People's Republic of China Re. Application No. 201580058321.X.

Office Action dated Nov. 13, 2019 and Search Report From the State Intellectual Property Office of the People's Republic of China Re. Application No. 201580058321.X. (7 Pages).

Translation Dated Nov. 19, 2019 of Office Action dated Nov. 13, 2019 From the State Intellectual Property Office of the People's Republic of China Re. Application No. 201580058321.X. (4 Pages).

* cited by examiner

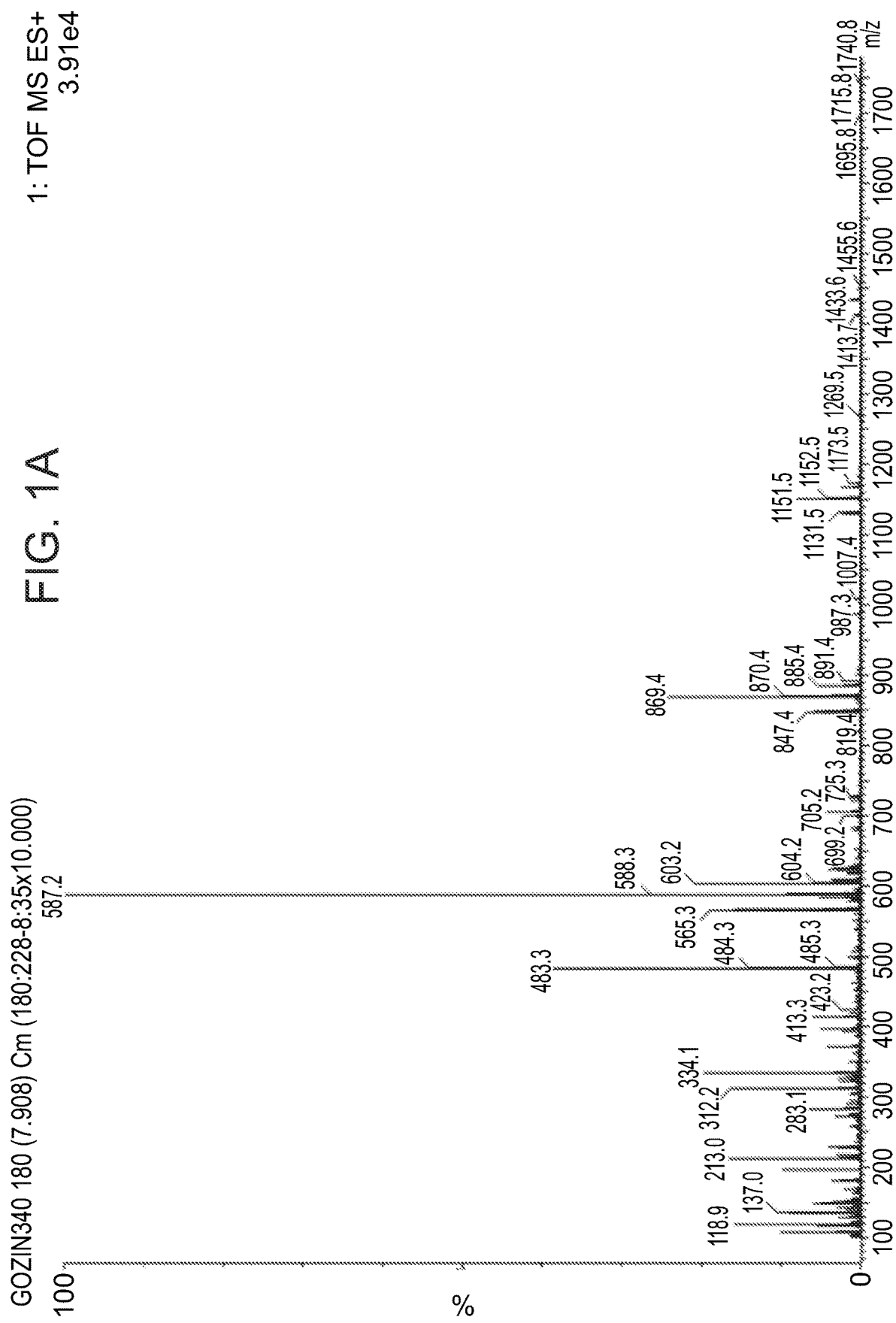

ENERGETIC COMPOUNDS AND COMPOSITIONS

RELATED APPLICATIONS

This application is a continuation of U.S. patent application Ser. No. 15/515,209 filed on Mar. 29, 2017, which is a national phase of PCT Patent Application No. PCT/IL2015/051057 having International Filing Date of Oct. 28, 2015, which claims the benefit of priority of Israel Patent Application No. 235415 filed on Oct. 30, 2014, the contents of which are incorporated herein by reference in their entirety.

FIELD AND BACKGROUND OF THE INVENTION

The present invention, in some embodiments thereof, relates to chemistry and, more particularly, but not exclusively, to energetic monomers, energetic macrocycles, energetic oligomers, energetic polymers and uses thereof.

Water-free fire protection systems are desired for providing superior protection for terrestrial, aerial and marine vessels, as well as for buildings, computer rooms, telecommunications facilities, museums and facilities operating emergency power generators, where exposure to water can cause a severe damage. These systems designed to rapidly fill the protected compartment with inert gas that can suffocate the fire, leaving practically no residues behind after they discharge. Similar requirements are present in the design and manufacturing of automotive airbags. The source of the inert gas can be storage tanks or chemical substances that can rapidly produce large quantities of inert gases. In some circumstances, the speed and capacity at which storage tanks can dispense inert gases are insufficient, and thus the most reliable and commonly used source of inert gases in such systems is the chemical substances.

Problems associated with chemical substances that can rapidly produce large quantities of inert gases are associated with the stability of these chemical substances, being highly energetic in some cases, and the toxicity thereof and of the residues they leave after discharge.

As a partial solution to the problem, $CBrF_3$, known as Halon 1301, was used since 1960's in "clean" fire-protection systems, due to this material high efficiency in fire-extinguishing and relatively low toxicity. Unfortunately, it was found that Halon 1301 is associated with the significant damage to the ozone layer and its use and manufacturing was restricted or altogether stopped. Halon 1301 was replaced by more environmentally-friendly hydroflourocarbons (HFCs); however, the latter materials were found to be 10-fold less effective in fire-extinguishing than Halon 1301 and HFCs' toxicity doses were found to be too close to concentrations of HFCs required for the fire-extinguishing. Moreover, upon exposure to an open flame, HFCs can decompose, releasing large quantities of a highly toxic and corrosive hydrogen fluoride that possesses great health hazards to occupants and rescue personnel, and damages equipment.

The materials capable to produce airbag's inflating gases should also be stable until detonated and be non-toxic. Nonetheless, the material which is still used today in many automotive airbags is nitrogen gas-generating compound sodium azide ($NaN_3$). Although $NaN_3$ has some advantages of operating at relatively low temperature, producing almost exclusively $N_2$ as the output gas, the major problem associated with sodium azide is its extreme toxicity, being comparable to the toxicity of sodium cyanide, making the use-in-manufacturing and disposal of $NaN_3$ very difficult and expensive, as well as a growing health hazard and grave environmental problem.

Energetic compounds have been used to inflate automobile airbags and aircraft occupant restraint bags. However, previously known nitrogen gas-generating materials are generally limited in one or more ways, e.g., they are overly impact-sensitive, difficult to synthesize on a large scale, difficult to shape, cast of mold, and generally not sufficiently energetic.

Castable energetic compounds are generally classified as either melt-castable or cast-cured. Melt-castable systems include those in which the energetic compound may be melted and cast into any type of mold. Cast-cured systems involve a mixture of one or more energetic compounds with a polymeric binder, cross-linker, plasticizer, and catalyst that is cast into any type of mold and allowed to cure in place.

While the bulk majority of energetic compounds and propellants are small, discrete molecules, the polymeric versions of these small molecules possess a number of significant potential advantages, which include, possibility to form intricate shapes by various processing methods (e.g. melt injection), potential for recovery/reuse (e.g. extrusion from a casing and then remolding), low inhalation hazard due to very low volatility even in a molten state, low dermal toxicity hazard (polymers are not readily absorbed through a skin by a direct contact), potential to control initiation and detonation velocity or rate of deflagration (propellants), by adjusting polymer chemical composition, microstructure and morphology. In general, energetic polymers are a class of energetic compounds, which are formed by polymerizing energetic monomers. In addition, energetic polymers may be formed by attaching energetic moieties to polymeric main chains (backbone functionalization). Energetic polymers can be both melt-castable and cast-cured, and can further be formed (polymerize) from their building blocks into any desirable shape.

A state-of-the-art overview of the various energetic polymers, employed for energetic compounds and propellant formulations, relevant to academic research and industrial R&D, as well as to industry and defense organizations, is provided in, for example, "Energetic Polymers", by How Ghee Ang and Sreekumar Pisharath, ISBN: 978-3-527-33155-0; "Energetic Polymers and Plasticizers for Explosive Formulations—A Review of Recent Advances" by Arthur Provatas, 2000, DSTO-TR-0966; "Investigation of Nitrogen-Rich Polymers Based on Tetrazoles and Triazoles" by Stefan M. Sproll, 2009, Ph.D. Thesis under supervision of Prof. Thomas M. Klapötke; and "Nitrogen-Rich Energetic Materials Based on 1,2,4-Triazole Derivatives" by Alexander A. Dippold, 2013, Ph.D. Thesis under supervision of Prof. Thomas M. Klapötke.

U.S. Pat. No. 3,375,230 teaches polymers having a high nitrogen content and more particularly is concerned with organic nitrogen-containing polymers, having a nitrogen-to-carbon atomic ratio greater than 1.

Additional prior art is found, for example, in Kizhnyaev, V. N. et al., *Polymer Science Series B*, 2011, 53(5-6), pp. 317-323; Xue, H. et al., *Journal of Polymer Science Part A: Polymer Chemistry*, 2008, 46(7), pp. 2414-2421; and Klapötke, T. M. et al., *Journal of Polymer Science Part A: Polymer Chemistry*, 2010, 48(1), pp. 122-127.

SUMMARY OF THE INVENTION

According to an aspect of some embodiments of the present invention there is provided a polymer selected from the group consisting of:

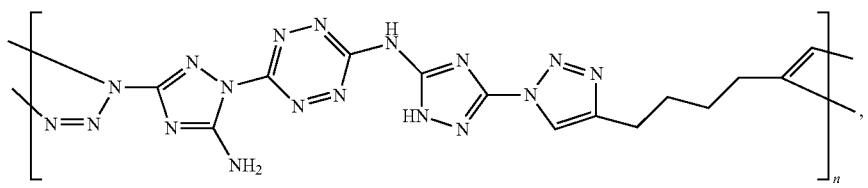
(TAUP133)
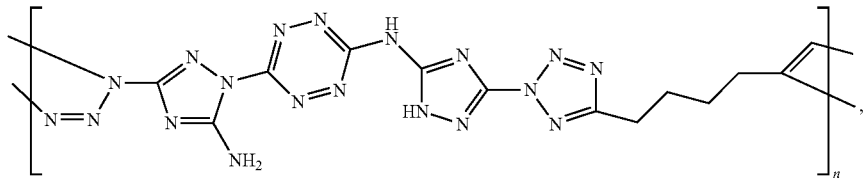
(TAUP183)
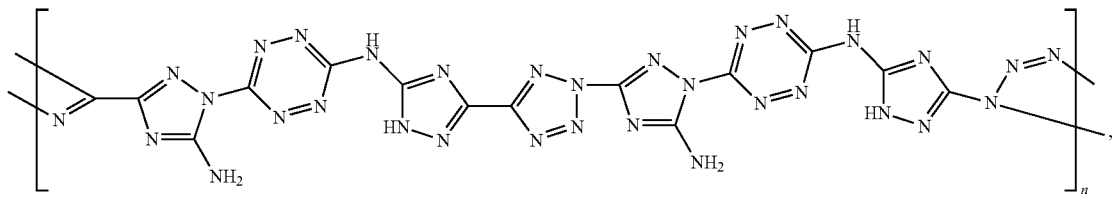
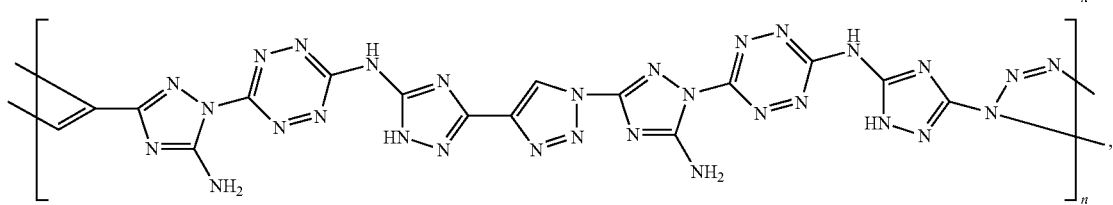
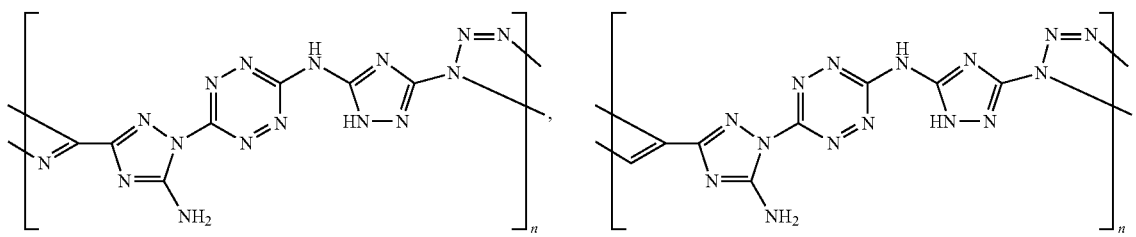
(AS199)
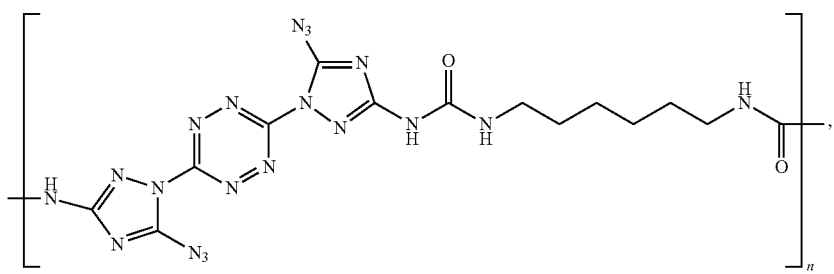
(TAUP5000)
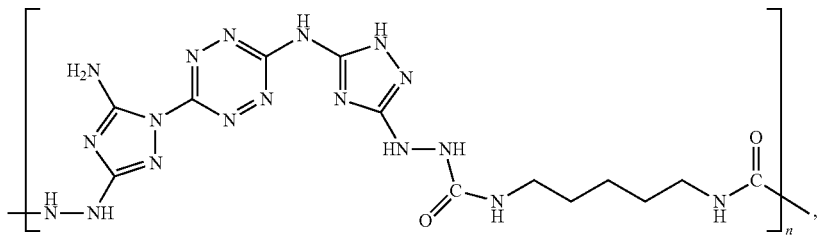

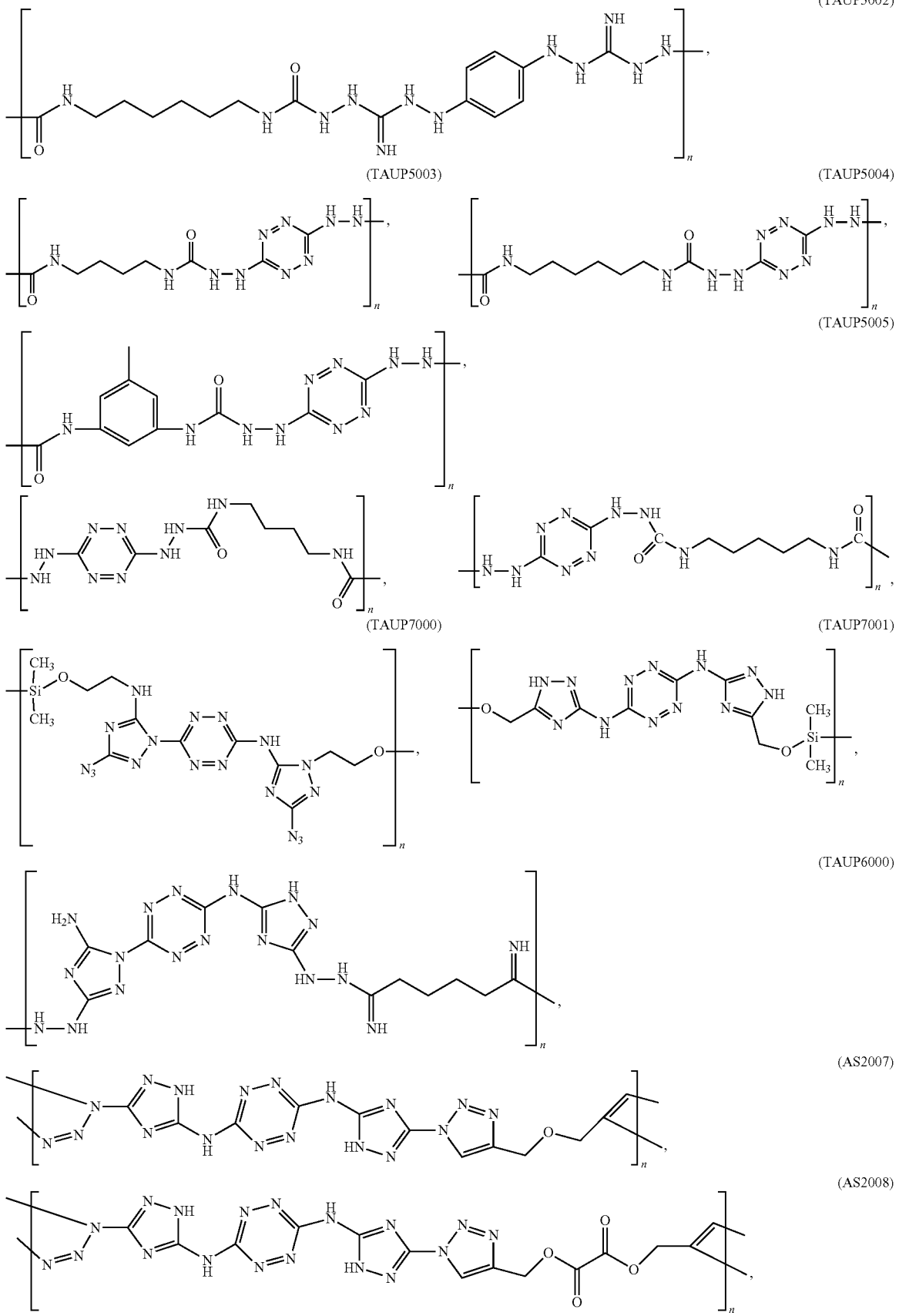

-continued
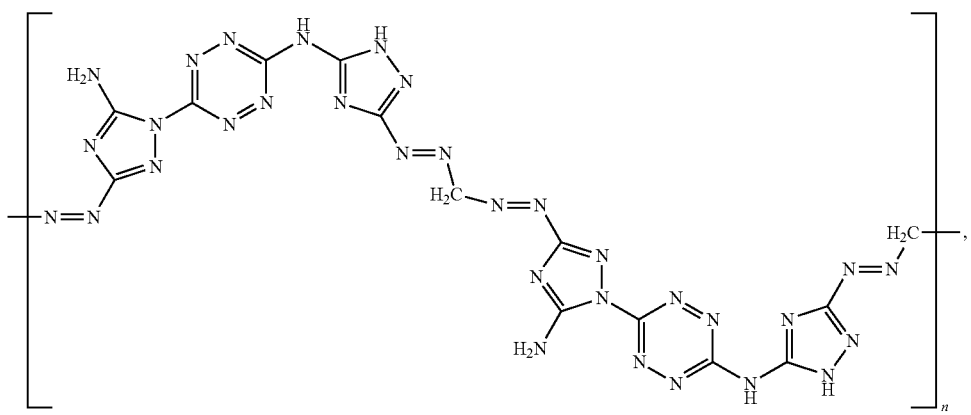
(TAUP2000)
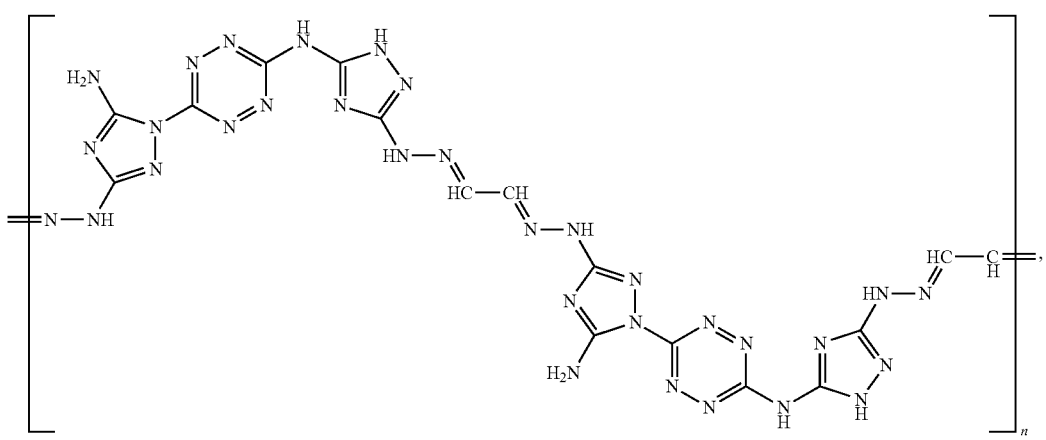
(TAUP3000)
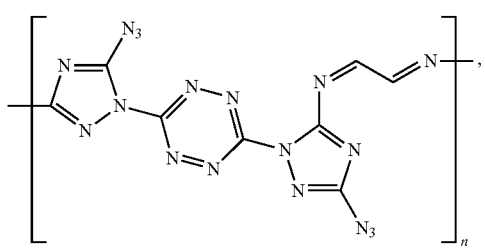
(AS196)
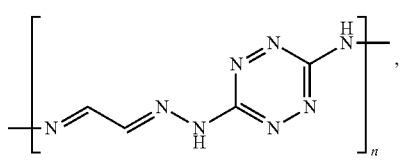
(AZ159)
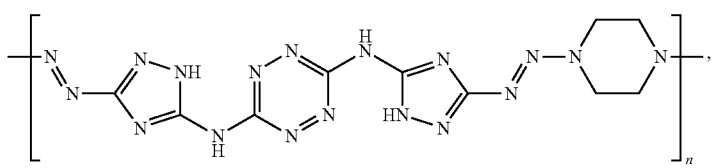
(TP121)
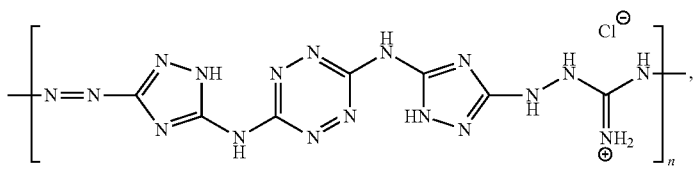
(TP113)
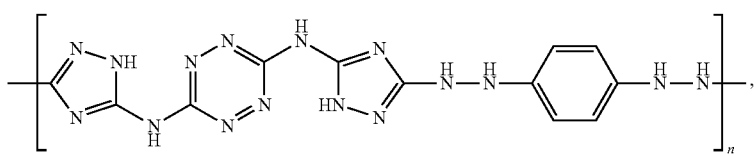
(TP116)

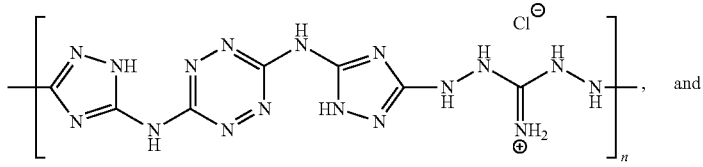
(TP138)
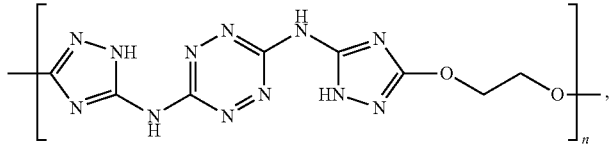
(TP143)
wherein n is an integer equal or greater than 2 and each of the polymers is linear or cyclic.
According to an aspect of some embodiments of the present invention there is provided a compound selected from the group consisting of:
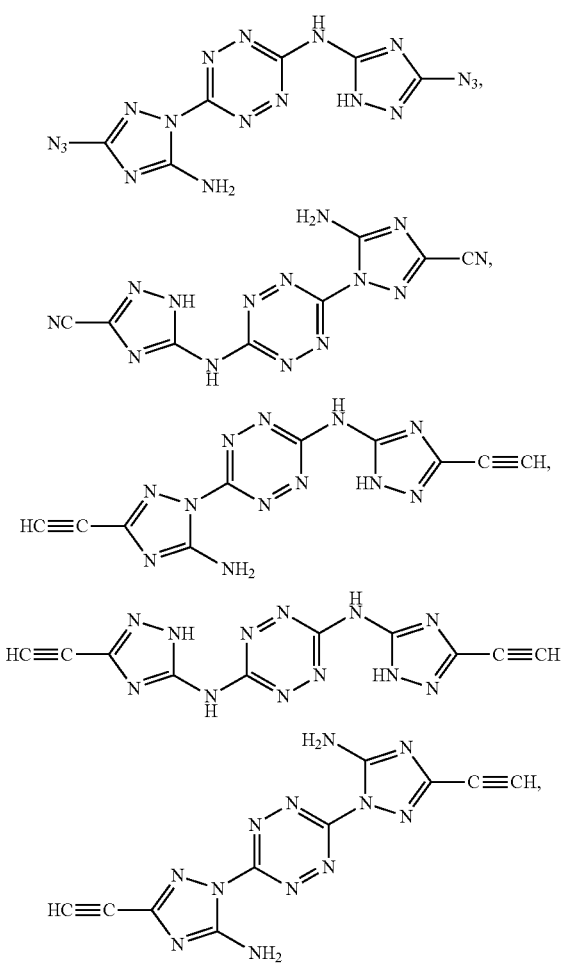
-continued
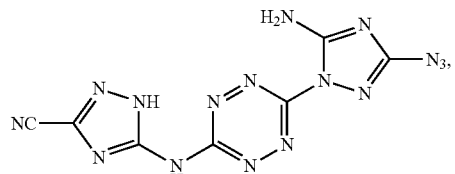
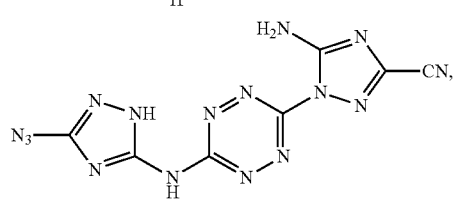
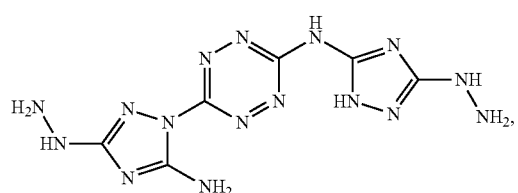
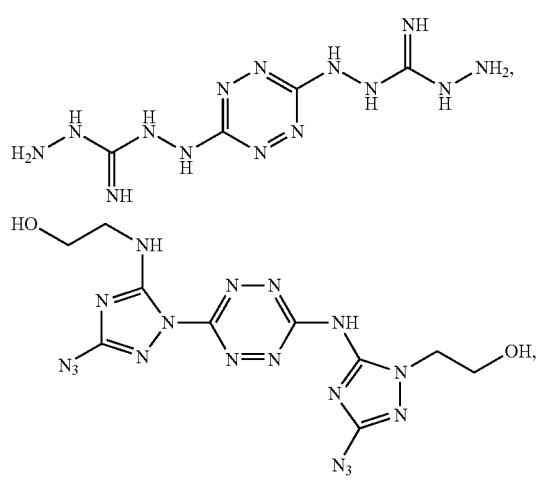

-continued

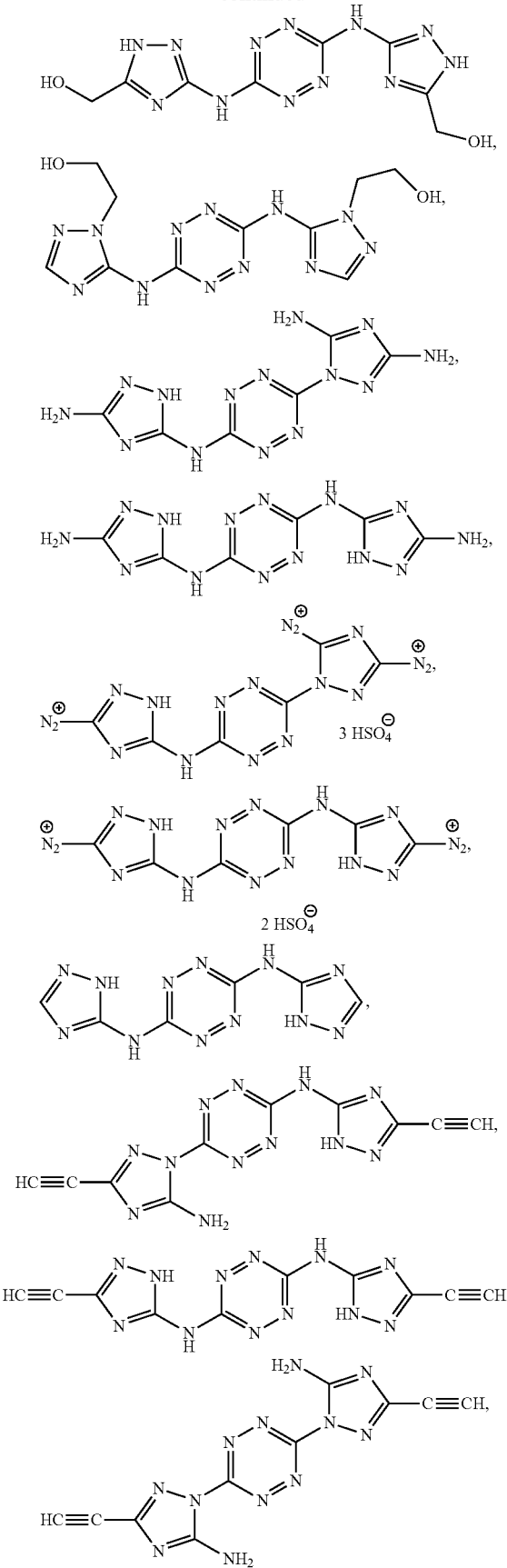

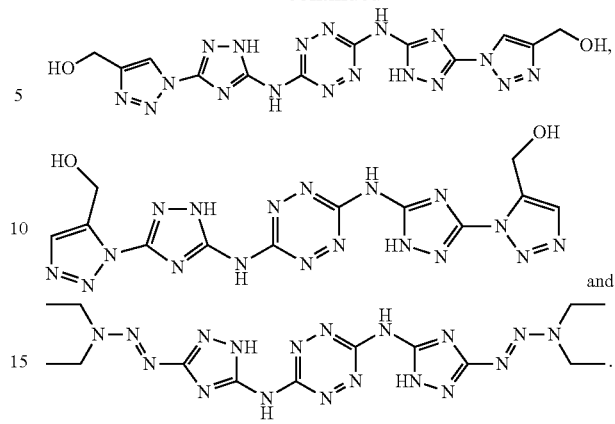

According to an aspect of some embodiments of the present invention there is provided a mixture of monomers, comprising at least a first monomer and a second monomer, the first monomer being represented by the Formula I:

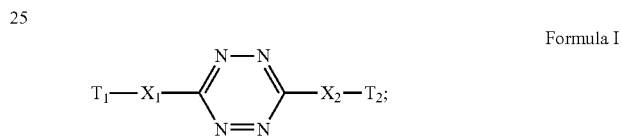

Formula I wherein:

each of X1 and X2 is independently NR or a covalent bond,

R is H or C1-4 alkyl, each of T1 and T2 is independently a moiety selected from the group consisting of a triazole moiety, a tetrazole moiety and a guanidine moiety, at least one of the T1 and T2 being substituted by at least one polymerizable group, the polymerizable group being selected from the group consisting of azido, cyano, diazonium, ethynyl, hydrazine, hydroxyl, hydrazide, amine, ethanolamine, isocyanate, cyanate, amide, imidate, ester, carboxyl and azo, and a C1-4 alkyl terminated with azido, cyano, diazonium, ethynyl, hydrazine, hydroxyl, hydrazide, amine, ethanolamine, isocyanate, cyanate, amide, imidate, ester, carboxyl and azo, and the second monomer being selected so as to form a polymer upon reacting with the first monomer via a reaction selected from metal-catalyzed click polymerization, organocatalysis, heterogeneous catalysis, poly-condensation and coupling, such that at least a portion of the backbone units of the polymer are derived from the first monomer and the second monomer.

According to some embodiments of the invention, at least one of the polymerizable groups of the first monomer is capable of forming a linking moiety with at least one of the polymerizable group of the second monomer, thereby forming the polymer.

According to some embodiments of the invention, the second monomer is represented by Formula I.

According to some of any of the embodiments of the invention, the guanidine moiety is represented by Formula II:

Formula II

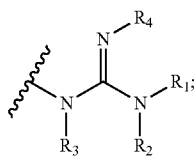

wherein each of R1, R2, R3 and R4 is independently H or the polymerizable group, provided that at least one of R1, R2, R3 and R4 is the polymerizable group.

According to some embodiments of the invention, R1 is amino, each of R2, R3 and R4 is H and the guanidine moiety is 1-aminoguanidine.

According to some of any of the embodiments of the invention, the triazole moiety is represented by a formula selected from the group consisting of Formula III, Formula IV and Formula V:

Formula III

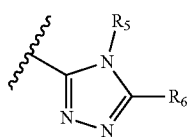

Formula IV

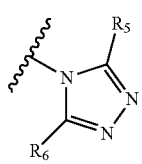

Formula V

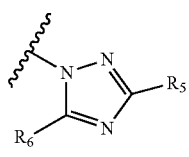

wherein each of R5 and R6 is independently H or the polymerizable group, provided that at least one of R5 and R6 is the polymerizable group.

According to some of any of the embodiments of the invention, the triazole moiety is selected from the group consisting of:

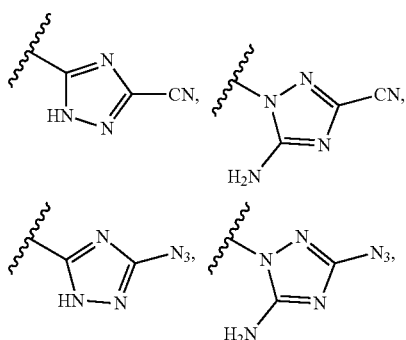

-continued

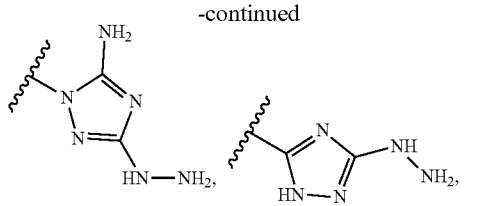

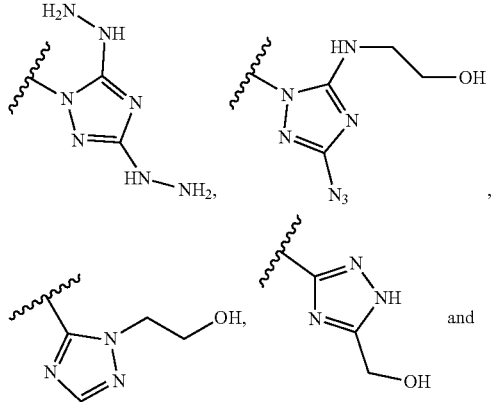

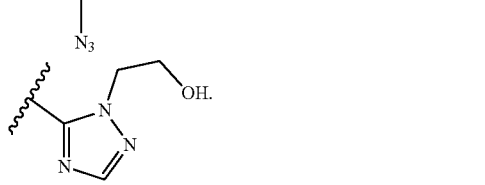

According to some of any of the embodiments of the invention, the tetrazole moiety is represented by a formula selected from the group consisting of:

Formula VI

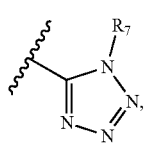

Formula VII

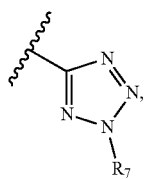

Formula VIII and

Formula IX

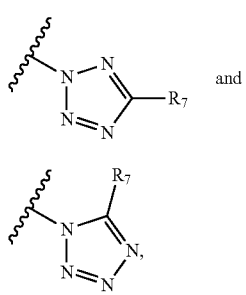

wherein R7 is the polymerizable group.

According to some of any of the embodiments of the invention, the tetrazole moiety is selected from the group consisting of:

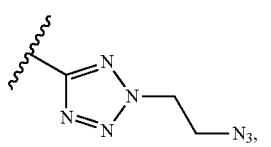
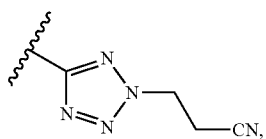
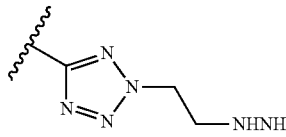 and
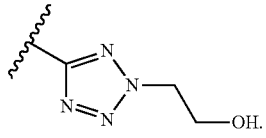
According to some of any of the embodiments of the invention, the first monomer is selected from the group consisting of:
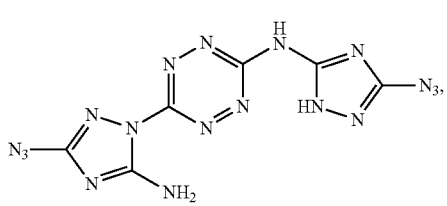
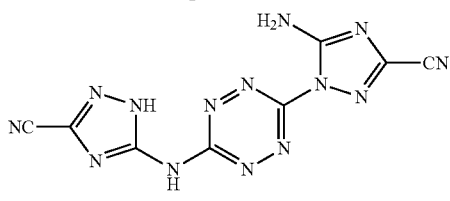
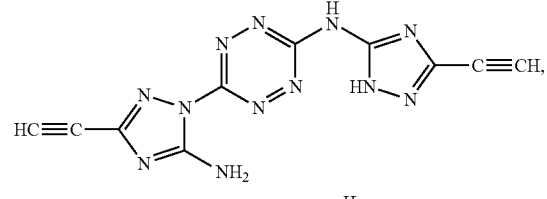
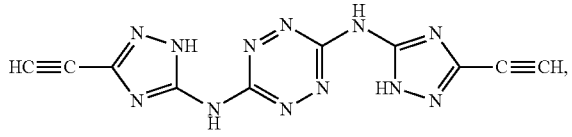
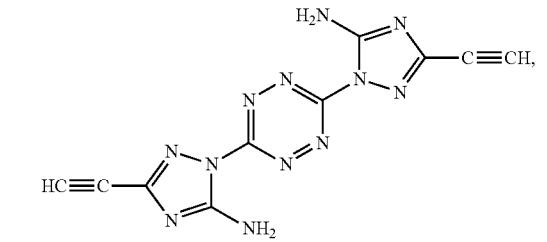
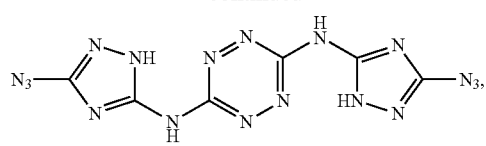
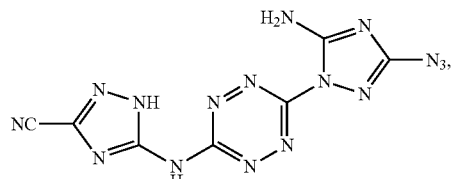
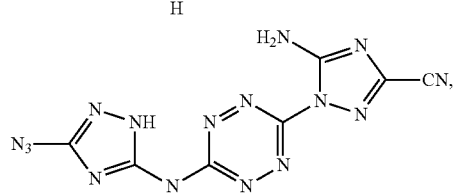
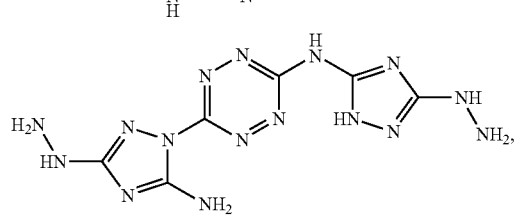
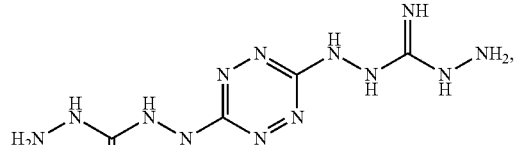
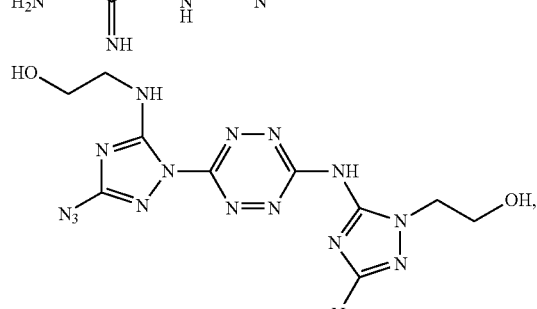
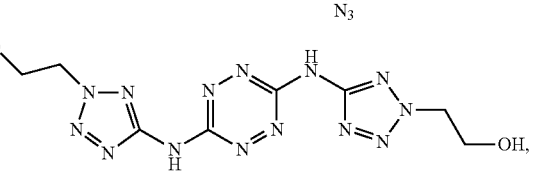
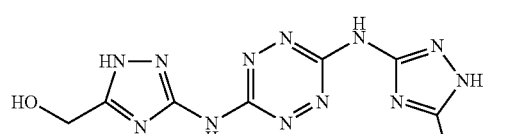
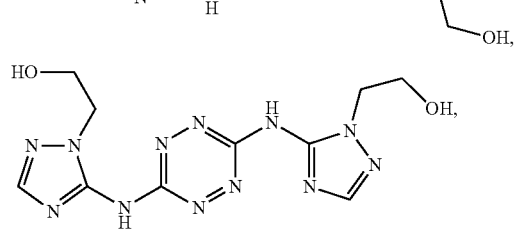

-continued

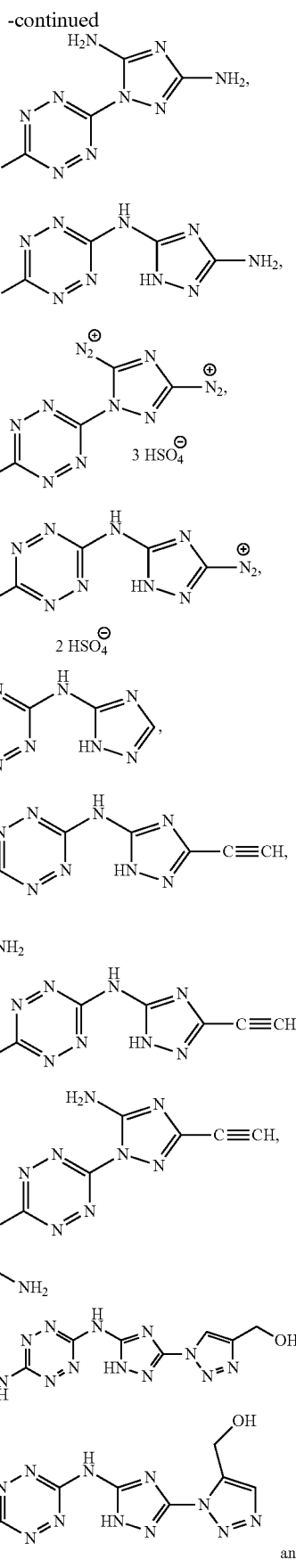

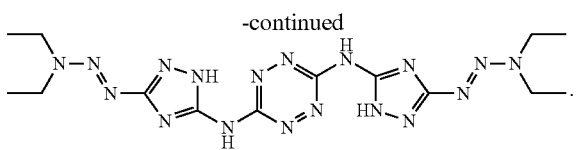

According to some of any of the embodiments of the invention, the second monomer is represented by Formula X:

$$R_8\text{—}A\text{—}R_9 \qquad \text{Formula X;}$$

wherein:

A is selected from the group consisting of C1-6 alkyl, cycloalkyl, heteroalicyclic, aryl and heteroaryl, and each of R8 and R9 is independently a polymerizable group selected from the group consisting of azido, cyano, diazonium, ethynyl, hydrazine, hydroxyl, hydrazide, amine, ethanolamine, isocyanate, cyanate, amide, imidate, ester, carboxyl and azo.

According to some of any of the embodiments of the invention, the second monomer is selected from the group consisting of 1,6-diisocyanatohexane, 1,4-dicyanobutane (adiponitrile) and dimethyl adipimidate.

According to some of any of the embodiments of the invention, the second monomer is a silane represented by Formula XI:

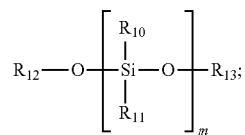

Formula XI wherein:

m is an integer ranging from 1 to 4; and each of R10 and R11 is independently selected from the group consisting of H, $C_{1-4}$ alkyl, $C_{1-4}$ alkenyl, aryl, heterocyclic and heteroaryl; and each of R12 and R13 is independently selected from the group consisting of H, a silane, $C_{1-4}$ alkyl and $C_{1-4}$ alkenyl.

According to some of the embodiments of the invention, m is 1, and each of R10, R11, R12 and R13 is independently and $C_{1-4}$ alkyl.

According to some of the embodiments of the invention, the silane is selected from the group consisting of dimethoxydimethylsilane and diethoxydimethylsilane.

According to an aspect of some embodiments of the present invention there is provided a polymer derived from the mixture of monomers according to some of any of the embodiments of the present invention such that at least a portion of the backbone units of the polymer are derived from the first monomer and the second monomer.

According to an aspect of some embodiments of the present invention there is provided a polymer obtainable by subjecting the mixture of monomer according to some of any of the embodiments of the present invention to conditions which promote a reaction selected from metal-catalyzed click polymerization, organocatalysis, heterogeneous catalysis, poly-condensation and coupling, such that at least a portion of the backbone units of the polymer are derived from the first monomer and the second monomer.

According to an aspect of some embodiments of the present invention there is provided an article of manufacturing comprising the polymer according to some of any of the embodiments of the present invention.

According to some of the embodiments of the invention, article is forming a part of a system selected from the group consisting of a fire extinguishing system, a safety airbag, an inflatable device, a buoy, a flotation device, a liquid nebulizer, a powder deployment device, a pneumatic actuator, a gas supply device and a valve actuator.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1B present an electrospray mass spectrogram (FIG. 1A) and a differential scanning calorimetric measurement (FIG. 1B) of TAUMC5003, an exemplary cyclic energetic polymer according to some embodiments of the present invention, comprising two 3,6-dihydrazinyl-1,2,4,5-tetrazine monomers and two 1,6-diisocyanatohexane monomers.

DESCRIPTION OF SPECIFIC EMBODIMENTS OF THE INVENTION

Figure 1B:
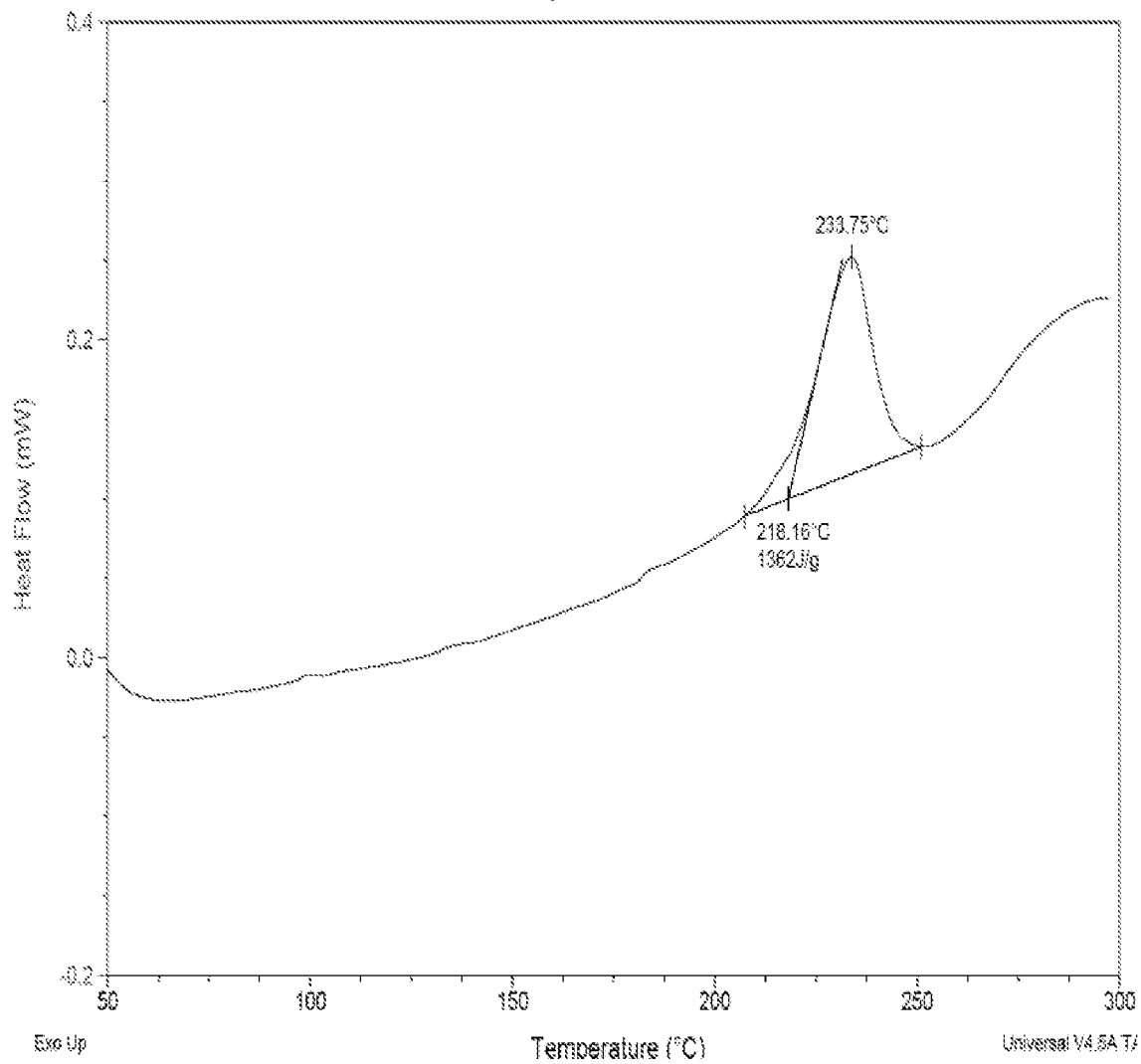

The present invention, in some embodiments thereof, relates to chemistry and, more particularly, but not exclusively, to energetic monomers, energetic macrocycles, energetic oligomers, energetic polymers and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, many of the presently employed chemicals in safety systems, such as fire-extinguishing systems and safety airbags, are toxic and/or environmentally hazardous. The present inventors have considered a family of nitrogen-rich energetic compounds, which can be used as monomers in the synthesis of nitrogen-rich energetic polymers.

The present inventors have recognized that polymers having nitrogen-rich energetic backbone units would possess a number of significant advantages over the presently known nitrogen-rich energetic small compounds. These advantages include significantly lower toxicity (due to higher molecular weight, lower volatility and extremely low solubility in water), a potential to control a burn-rate and other energetic properties, by adjusting polymer molecular weight, chemical composition, structure and morphology, and the ability to be molded, casted or otherwise take a large variety of macroscopic forms and shapes.

The present inventors have devised and practiced novel nitrogen-enriched monomers and polymers composed thereof, which can be used for providing products and systems, which are reasonably safe and environmentally friendly.

Monomers:

According to an aspect of some embodiments of the present invention, there is provided an energetic and polymerizable compound, or monomer, based on 1,2,4,5-tetrazine and represented by the general Formula I:

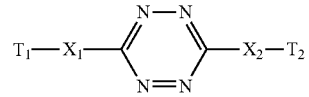

Formula I wherein:

each of $X_1$ and $X_2$ is independently NR or a covalent bond,

R is H or C1-4 alkyl, and each $T_1$ and $T_2$ is independently a moiety selected from the group consisting of a triazole moiety, a tetrazole moiety and/or a guanidine moiety, and at least one of said $T_1$ and $T_2$ being substituted by at least one polymerizable group.

Exemplary polymerizable group, according to some embodiments of the present invention, include without limitation, azido, cyano, diazonium, ethynyl, alkynyl, hydrazine, hydroxyl, hydrazide, amine, ethanolamine, isocyanate, cyanate, amide, imidate, ester, carboxyl and azo, and a C1-4 alkyl terminated with azido, cyano, diazonium, ethynyl, alkynyl, hydrazine, hydroxyl, hydrazide, amine, ethanolamine, isocyanate, cyanate, amide, imidate, ester, carboxyl and azo, as these terms are defined hereinbelow.

According to some embodiments of the present invention, the guanidine moiety is having the general Formula II:

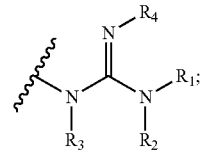

Formula II wherein each of $R_1$, $R_2$, $R_3$ and $R_4$ is independently H or a polymerizable group, provided that at least one of $R_1$, $R_2$, $R_3$ and $R_4$ is a polymerizable group.

It is noted that the wavy line across a bond represents the position/bond connecting the moiety to a respective position in a molecular structure, such as Formula I.

Exemplary guanidine moieties, according to some embodiments of the present invention, include without limitations, guanidine moieties wherein $R_1$ is amino and each of $R_2$, $R_3$ and $R_4$ is H. Such guanidine moiety is referred to as 1-amino-guanidine or hydrazine-carboximidamide.

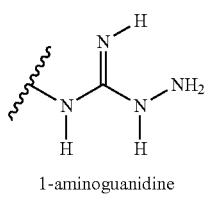 [SMILES: *N/C(=N/[H])NN]

1-aminoguanidine

According to some embodiments of the present invention, the triazole moiety can be represented by three general formulae:

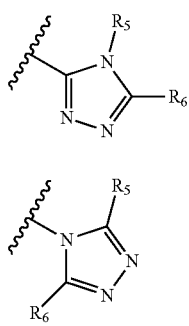

Formula III

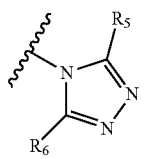

Formula IV

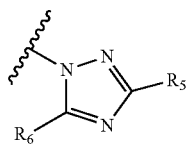

Formula V wherein each of $R_5$ and $R_6$ is independently H or a polymerizable group, provided that at least one of $R_5$ and $R_6$ is a polymerizable group.

Exemplary triazole moieties, according to embodiments of the present invention, include without limitation:

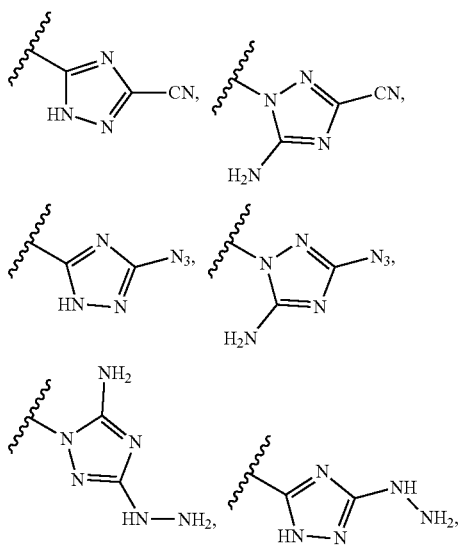

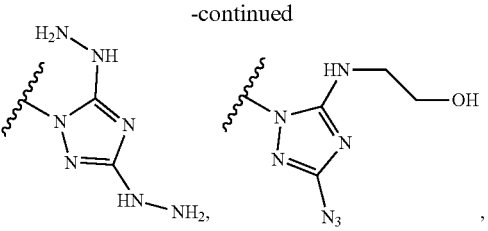

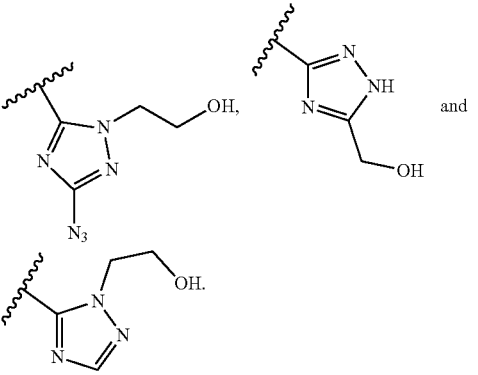

According to some embodiments of the present invention, the tetrazole moiety can be represented by four general formulae:

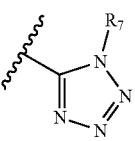

Formula VI

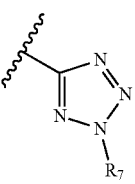

Formula VII

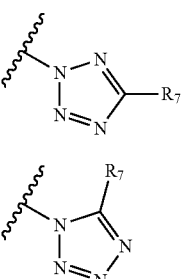

Formula VIII

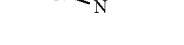

Formula IX wherein $R_7$ is said polymerizable group.

Exemplary tetrazole moieties, according to embodiments of the present invention, include without limitation:

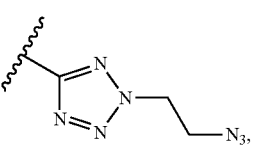

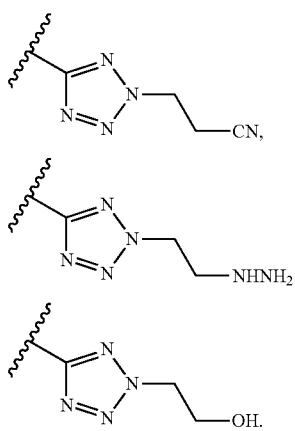

As discussed hereinabove, the nitrogen-rich energetic polymerizable compound represented by Formula I is contemplated as a monomer of a nitrogen-rich energetic polymer.

Exemplary monomers that fall under Formula I, according to embodiments of the present invention, include without limitation:

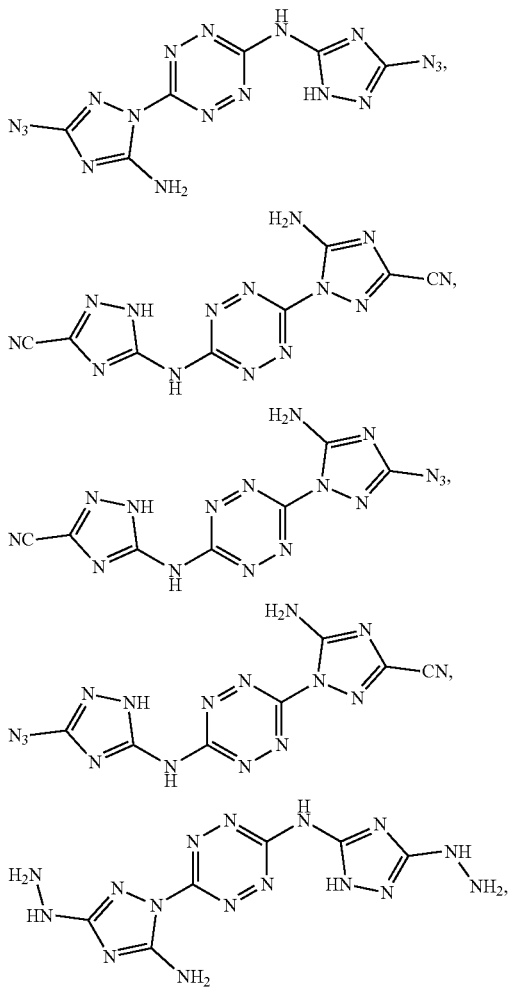

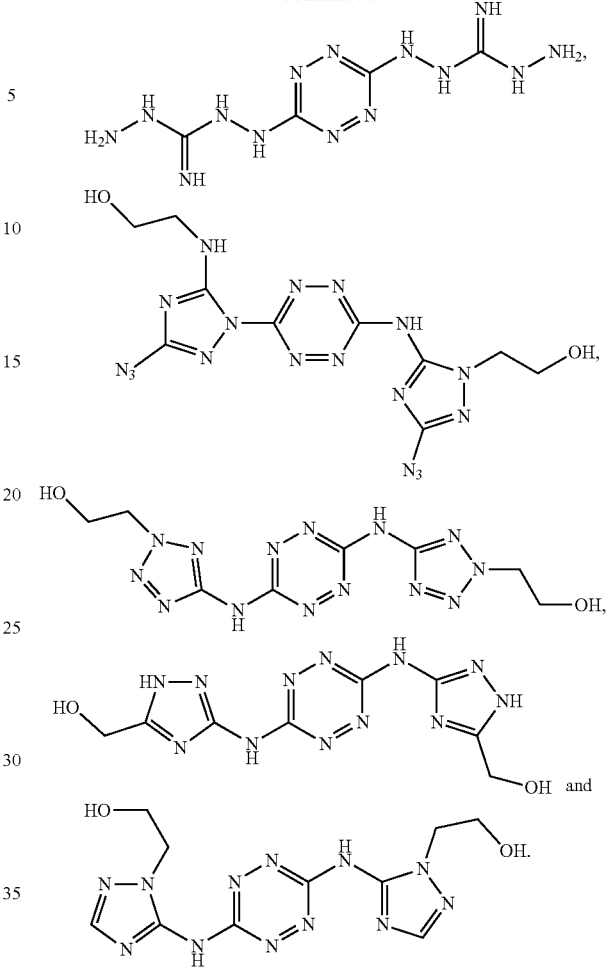

According to some embodiments, the N:C ratio (the ratio of nitrogen to carbon atoms in the molecule), is more than 1.1, more than 1.3, more than 1.5, more than 1.7, more than 1.9, more than 2.1, more than 2.3, more than 2.5, more than 2.7, more than 2.9, more than 3 or more than 3.5.

Mixture of Monomers:

According to an aspect of some embodiments of the present invention, there is provided a mixture of monomers, which comprises at least a first monomer and a second monomer; wherein the first monomer is represented by general Formula I described hereinbelow. According to embodiments of the present invention, the first and second monomers are selected such that the two types of monomers are compatible in the sense that they can undergo a polymerization reaction and substantially become backbone units of a polymer. In other words, and first and second monomers are selected so as to form a polymer upon reacting the monomers therebetween via a polymerization reaction, as presented hereinbelow. In the context of embodiments of the present invention, at least a portion of the backbone units of the resulting polymer are derived from the first and second monomers.

According to some embodiments, the mixture of monomers is such that at least one of the polymerizable groups of the first monomer, represented by general Formula I, is capable of forming a linking moiety with at least one of the polymerizable groups of the second monomer, thereby forming the backbone of a polymer.

Scheme A below presents a schematic illustration of the definitions of the terms "monomer", "polymerizable group" (PG), "linking moiety" (LM), "backbone" and "polymer":

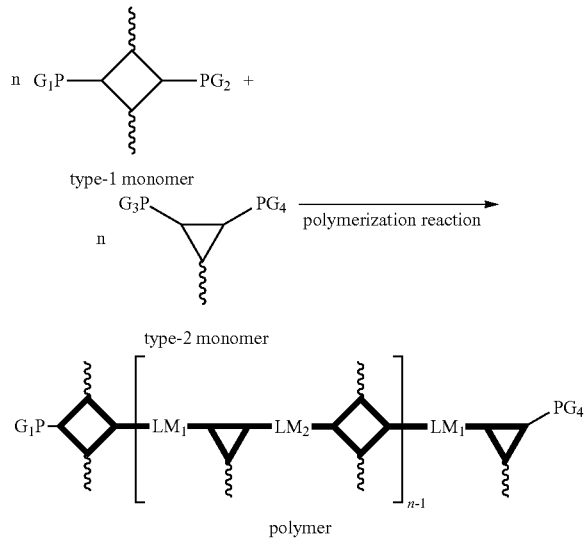

type-1 monomer type-2 monomer polymer

As can be seen in the exemplary polymerization reaction, illustrated in Scheme A, each of the types of monomers has two types polymerizable groups, denoted $PG_1$-$PG_4$, wherein $PG_1$ is capable of reacting with $PG_4$ to form one type of linking moiety ($LM_2$), and $PG_2$ is capable of reacting with $PG_3$ to form another type of linking moiety ($LM_1$), such that upon subjecting a mixture of monomers to polymerization reaction conditions, a polymer is formed from the monomers, the backbone of which is shown in bold in Scheme A.

It is noted that Scheme A is an illustration of a particular exemplary case of polymerization, namely a co-polymerization of two different types of monomers, each having two different polymerizable groups which form two types of linking moieties; however, there are other types of polymerizations in the field of polymers. A polymer can be formed from a single type of monomer, having two types of polymerizable groups that form a single type of a linking moiety. A polymer can be formed from two types of monomers, each having the same two types of polymerizable groups that form a single type of linking moiety.

Typically, a polymer that is afforded from more than one type of monomers is referred to as a co-polymer, and in the context of the present invention, the term "polymer" encompasses all types of polymers, including single-monomer polymers (homopolymers), co-polymers, alternating co-polymers, periodic co-polymers, statistical co-polymers and block co-polymers, as these terms are known in the art.

According to some embodiments of the present invention, each of the first and the second monomers can be independently represented by general Formula I, provided that at least one polymerizable group of the first monomer is capable of forming a linking moiety with at least one polymerizable group of the second monomer.

Polymerizable groups that are capable of forming a linking moiety in a polymer are referred to herein and throughout as "compatible polymerizable groups".

According to some embodiments, the first and second monomers under Formula I are the same, and having at least two compatible polymerizable groups that can form linking moieties in a homopolymer made therefrom.

According to some embodiments, the second monomer is having the general Formula X:

wherein:

A is selected from the group consisting of C1-6 alkyl, cycloalkyl, heteroalicyclic, aryl and heteroaryl, and each of R8 and R9 is independently a polymerizable group selected from the group consisting of azido, cyano, diazonium, ethynyl, hydrazine, hydroxyl, hydrazide, amine, ethanolamine, isocyanate, cyanate, amide, imidate, ester, carboxyl and azo, as these are defined herein.

Non-limiting examples of a second monomer include 1,6-diisocyanatohexane, 1,4-dicyanobutane (adiponitrile) and dimethyl adipimidate.

According to some embodiments, the second monomer is a silane having the general Formula XI:

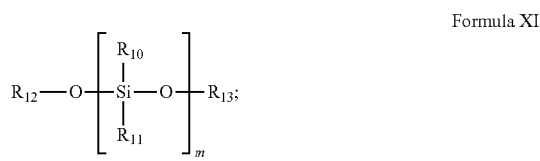

wherein:

m is an integer ranging from 1 to 4; and each of R10 and R11 is independently selected from the group consisting of H, $C_{1-4}$ alkyl, $C_{1-4}$ alkenyl, aryl, heterocyclic and heteroaryl; and each of R12 and R13 is independently selected from the group consisting of H, a silane, $C_{1-4}$ alkyl and $C_{1-4}$ alkenyl.

Representative non-limiting examples of a silane-based second monomer can be found in, for example, WO 2012/172176, which is incorporated by reference herein.

Other exemplary silane-based second monomer include, without limitation, silane compounds according to Formula XI wherein m is 1, and each of R10, R11, R12 and R13 is independently and $C_{1-4}$ alkyl, such as dimethoxydimethylsilane and diethoxydimethylsilane.

Polymerization:

According to some of any of the embodiments, the first and the second monomers undergo a polymerization reaction, such as a metal-catalyzed "click polymerization" reaction (also known as metal-catalyzed Huisgen 1,3-dipolar cycloaddition), organocatalysis, heterogeneous catalysis, a polycondensation reaction and a coupling reaction.

Briefly, the phrase "metal-catalyzed click polymerization reaction", as used herein, refers to a polymerization reaction which is catalyzed by a base, a ligand that would be coordinated to a metal ion and a metal ion, typically copper, ruthenium, silver, iridium, zinc, palladium, platinum, phosphomolybdic acid ($H_3Mo_{12}O_{40}P$) and titania-supported gold nanoparticles, or a combination thereof, and involved the formation of a nitrogen-rich 5-membered heteroaryl moiety by fusing an azido polymerizable group with a polymerizable group having a triple bond, such as an ethynyl (resulting in the formation of a triazole moiety) or a cyano polymerizable group (resulting in the formation of a tetrazole moiety).

Scheme B and Scheme C below present the concept of the click polymerization reaction, wherein Scheme B illustrates the formation of a co-polymer characterized by fusion of a cyano polymerizable group and an azido polymerizable group into a tetrazole moiety, and Scheme C illustrates the formation of a homopolymer characterized by fusion of an ethynyl polymerizable group and an azido polymerizable group into a triazole moiety.

Scheme D and Scheme E below illustrate exemplary poly-condensation reactions between a diimidate (Scheme D) or a diisocyanate (Scheme E) molecule and a dihydrazine molecule:

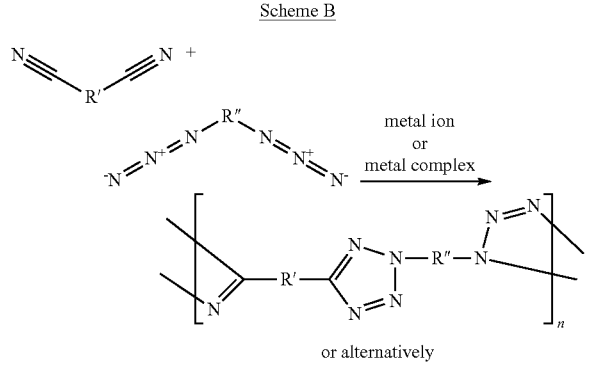

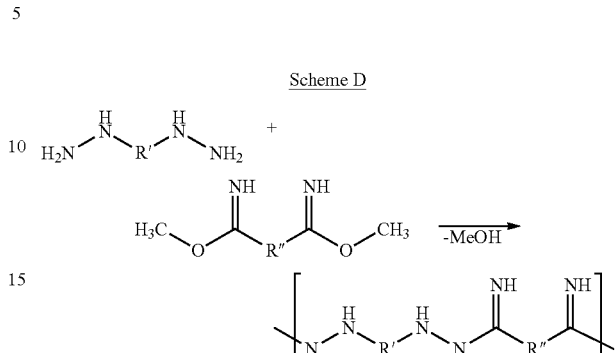

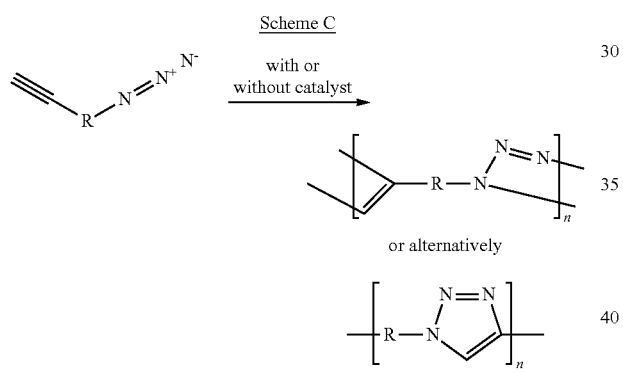

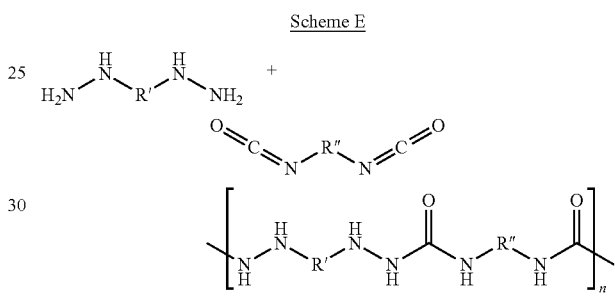

Scheme F below illustrates an exemplary poly-condensation reaction between a dihydroxyl molecule and a silane-based molecule:

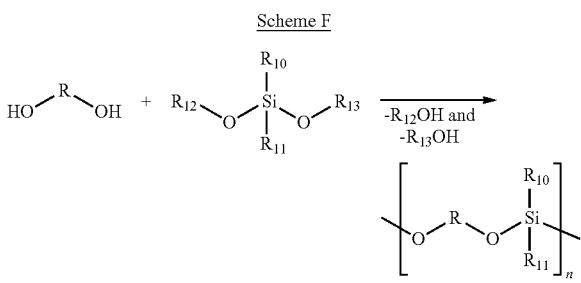

It is noted that in Schemes B and C, and any other schematic illustration of a polymer presented herein, the polymer is presented as having an infinite length; however it is to be understood that unless the polymer is cyclic, it is capped by terminal groups that can be the terminal polymerizable groups of the terminal monomer, or any other terminal groups, as well as groups that branch the polymer (as in a T, Y or hub links) or prevent further propagation and elongation of the polymer.

A comprehensive overview of the "click" polymerization methodology is presented, for example, by Qin, A. et al. [*Macromolecules*, 2010, 43, pp. 8693-8702].

It is noted herein that since during "click" polymerization process a nitrogen-rich moiety is formed, this type of polymerization is useful in the context of embodiments of the present invention.

The term "poly-condensation reaction", as used herein, refers to a chemical reaction in which two molecules, moieties, functional or polymerizable groups, combine to form a larger molecule in a reaction that releases a small molecule, typically water, hydrogen chloride, methanol or acetic acid. Exemplary types of condensation polymers include polyamides, polyacetals and polyesters.

The term "coupling reaction", as used herein, refers to a chemical reaction that binds two or more compounds containing an amine and/or hydrazine polymerizable groups, each to a coupling agent which is a compound containing aldehyde and/or isocyanate polymerizable groups, whereas a residue of the coupling agent bridges between the two or more compounds. Exemplary types of coupling reaction involve formaldehyde, glyoxal or a diisocyanate that act as a coupling agent between two compounds having at least two amine groups, at least two hydrazine groups or combinations thereof.

Scheme G below illustrates an exemplary coupling polymerization reaction between a dihydrazine molecule and formaldehyde:

Scheme G

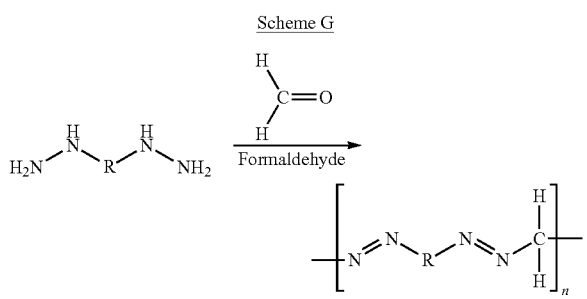

Scheme H below illustrates an exemplary coupling polymerization reaction between a dihydrazine molecule and glyoxal:

Scheme H

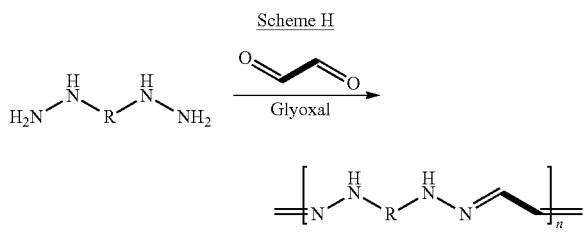

Scheme I below illustrates an exemplary coupling polymerization reaction between a dihydrazine molecule and a diisocyanate molecule:

Scheme I

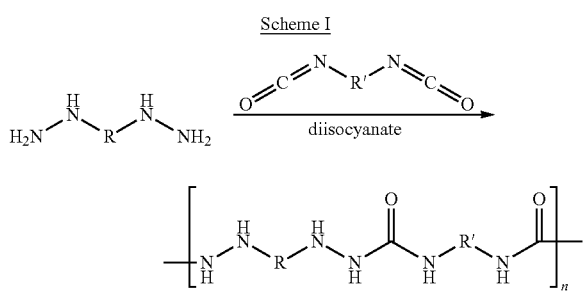

As presented hereinabove, the polymerizable groups of each of the first and second monomers are selected such that they can undergo a polymerization reaction that forms a linking moiety therebetween. For non-limiting examples, an azido group is compatible to form a linking moiety with both nitrile (cyano) and alkynyl polymerizable groups ("click" polymerization reaction) and afford a tetrazole or a triazole linking moiety respectively; a hydrazine polymerizable group is compatible with, for a non-limiting example, an isocyanate polymerizable group (condensation polymerization reaction) and affords an amino-urea linking moiety; an imidate polymerizable group is compatible with, for a non-limiting example, a carboxyl polymerizable group (condensation polymerization reaction) and affords an imido-hydrazide linking moiety; a hydroxyl group is compatible with a alkoxy-silyl group (R—O—Si(R)$_2$— group) (condensation polymerization reaction) and affords an ether linking moiety; and the likes, as these compatibility pairs of polymerizable groups are known in the art.

Polymer:

According to an aspect of some embodiments of the present invention, there is provided a polymer, which is derived from any one of the mixtures of the first monomer and the second monomer presented hereinabove, such that at least a portion of the backbone units of the polymer are derived from the monomers.

According to an aspect of any of the embodiments presented herein, there is provided a polymer, which is obtainable by subjecting the mixture of monomer presented herein to conditions, which promote a reaction selected from metal-catalyzed click polymerization, poly-condensation and coupling, such that at least a portion of the backbone units of the polymer are derived from the first monomer and second monomers.

Exemplary polymers, according to embodiments of the present invention, can be formed from a plurality of identical monomers represented by Formula I, or by a plurality of two different types of monomers represented by Formula I, or by a plurality of two different types of monomers, at least one of which is represented by Formula I. It is to be understood that the polymers provided herewith are not limited to polymers derived from two types of monomers, and can be derived from one, two, three, four or more types of monomers, at least one of which is represented by Formula I.

According to one exemplary embodiment of the present invention, the polymer, which is derived from one type of monomer having two types of compatible polymerization groups, is:

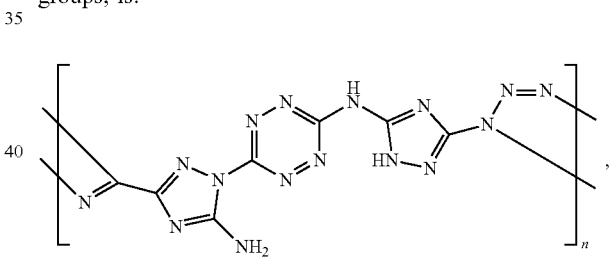

wherein the monomer being represented by general Formula I is:

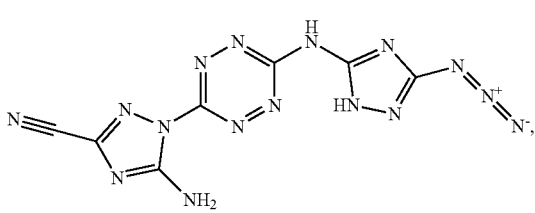

one of the polymerizable groups is azido, the other polymerizable group is cyano, and the linking moiety, which is formed upon polymerization is a tetrazole.

According to another exemplary embodiment of the present invention, the polymer, which is derived from two types of monomers, each having one type of polymerization groups compatible with the type of polymerizable groups of the other monomer, is:

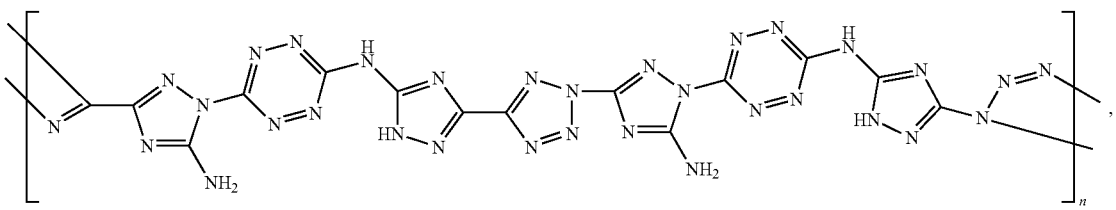

wherein one of the monomers being represented by general Formula I is:

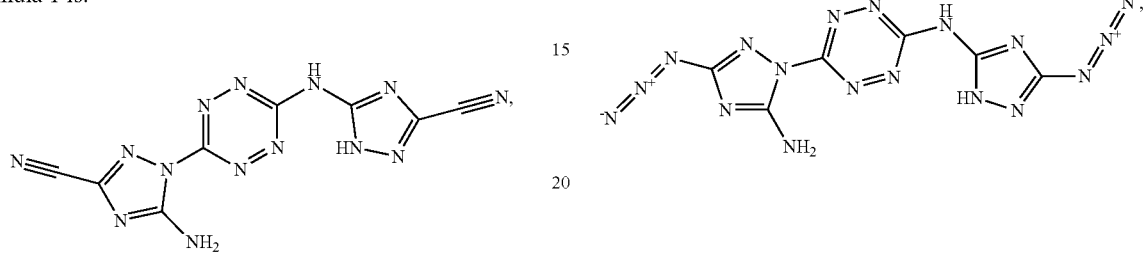

having two cyano polymerizable groups, the other monomers also being represented by general Formula I is:

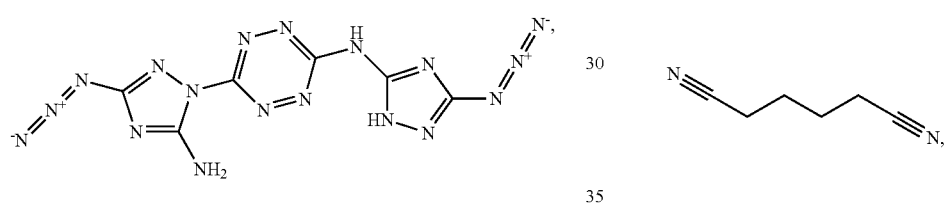

having two azido polymerizable groups, and the linking moiety, which is formed upon polymerization is a tetrazole.

According to another exemplary embodiment of the present invention, the polymer, which is derived from two types of monomers, each having one type of polymerization groups compatible with the type of polymerizable groups of the other monomer, is:

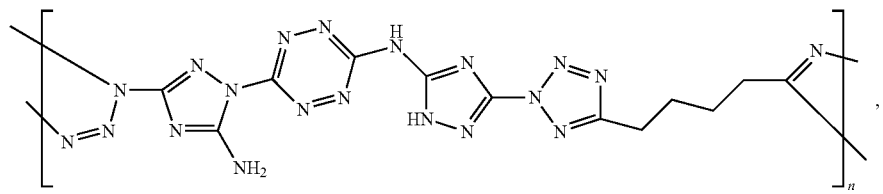

wherein one of the monomers being represented by general Formula I is:

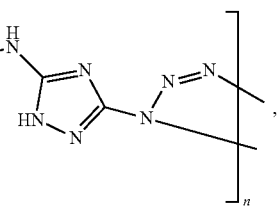

having two azido polymerizable groups, the other monomer is:

N≡C—CH₂CH₂CH₂CH₂—C≡N, having two cyano polymerizable groups, and the linking moiety, which is formed upon polymerization is a tetrazole.

According to an aspect of some embodiments of the present invention, the polymer that can be formed from the mixture of monomers presented hereinabove, include, without limitation:

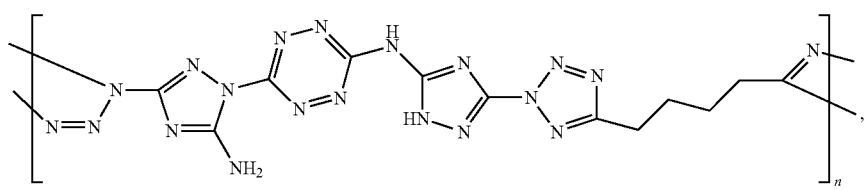

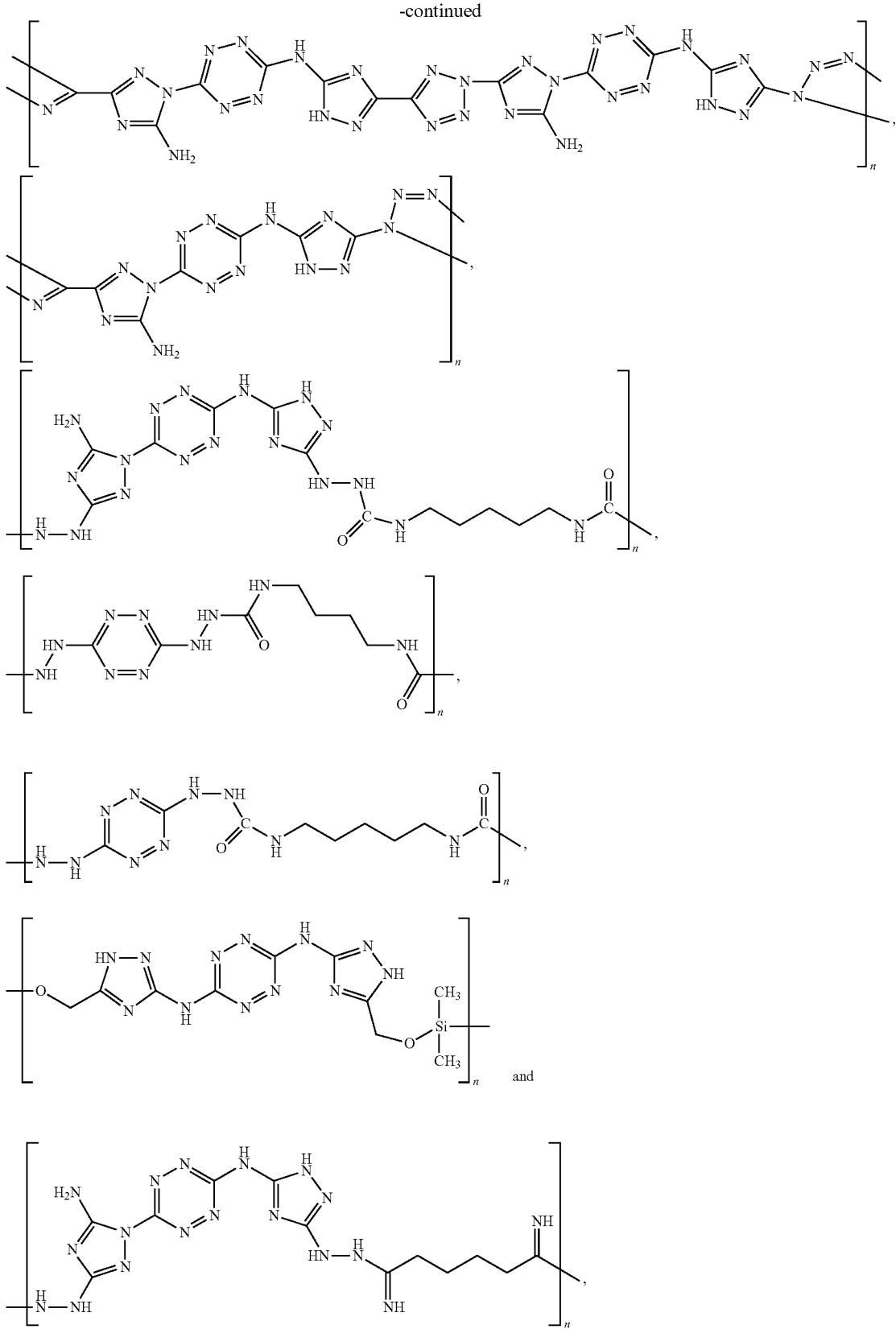
wherein n is an integer and each of the polymers can be linear or cyclic.

When the polymer is linear, it is capped by either the polymerizable group corresponding to the terminating monomers, or capped by any other group or atoms.

For example, six 6-(5-amino-3-azido-1H-1,2,4-triazol-1-yl)-N-(3-azido-1H-1,2,4-triazol-5-yl)-1,2,4,5-tetrazin-3-amine monomers and five adiponitrile monomers, that underwent a "click" polymerization reaction in the presence of copper ions, may form the following linear 11-mer polymer (polymer comprising 11 monomers, marked by numbers in Scheme G below):

According to some embodiments of the present invention, the article of manufacturing forma a part of a system selected from the group consisting of fire extinguishing systems, safety airbags, inflatable devices for expandable structures, floats, buoys and other flotation devices such as rescue boats and vests, pressurized mist generators and liquid nebulization and powder deployment systems, gas supply devices for pneumatic actuators or for gas or liquids tanks pressurization (including pressurized tanks containing fire extinguishing liquids), devices capable of pushing fluids Scheme G

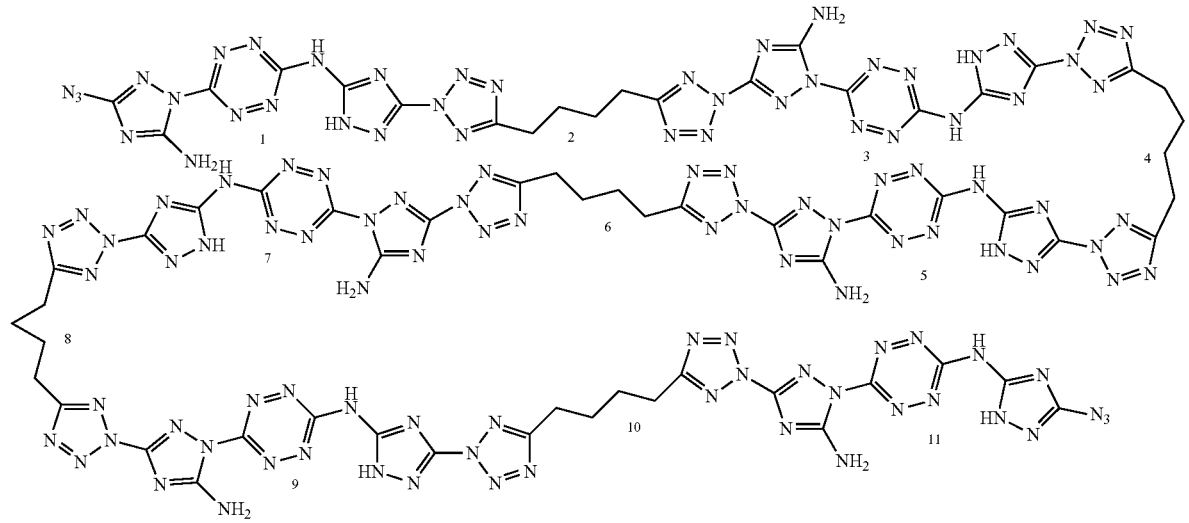

When the polymer is cyclic, it can have any number of repeating units, which are attached head to tail to form a polymeric ring. For example, two 6-(5-amino-3-hydrazinyl-1H-1,2,4-triazol-1-yl)-N-(3-hydrazinyl-1H-1,2,4-triazol-5-yl)-1,2,4,5-tetrazin-3-amine monomers and two dimethyl adipimidate monomers that underwent a polycondensation reaction, while releasing methanol, may form the following cyclic tetramer (a cyclic polymers having 2+2 monomers, marked by numbers in Scheme H below):

Scheme H

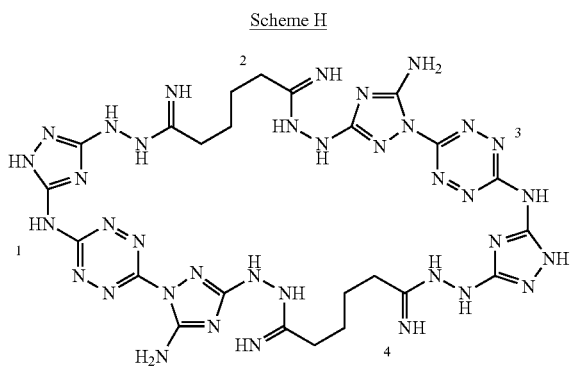 [SMILES: N=C1CCCCC(=N)NNc2nc(N)n(n2)-c2nnc(nn2)Nc2nc(n[nH]2)NNC(=N)CCCCC(=N)NNc2nc(N)n(n2)-c2nnc(nn2)Nc2nc(n[nH]2)NN1]

Article of Manufacturing:

According to an aspect of some embodiments of the present invention, there is provided an article of manufacturing comprising any one of the nitrogen-rich energetic polymers presented hereinabove.

in lab-on-a-chip applications, or to power various valve actuators.

Definitions:

As used herein, the term "monomer" refers to is a molecule that is capable of forming a chemical bond with other molecules to form a polymer. In the context of embodiments of the present invention, the term "monomer" is also used to describe a constituent of the pre-polymerization mixture, which affords a polymer upon polymerization. The pre-polymerization mixture is therefore a mixture of monomers, which is capable of undergoing a polymerization reaction that affords at least one type of polymer, whereas the monomers form a part of the polymer as a backbone unit thereof.

The term "polymerizable group", as used herein, refers to a chemical group of one compound that is capable of reacting with a compatible polymerizable group of another compound, such that the two polymerizable groups form a linking moiety, and the two compounds essentially form a part of a backbone of a polymer.

As used herein, the phrase "linking moiety" describes a bond, a chemical moiety or a chemical group, which links between backbone units in a polymer. The linking moiety can thus be, for example, formed upon reacting two polymerizable groups.

The term "backbone", as used herein, refers to the main chain of a polymer, which includes of a series of covalently bonded atoms that together create the longest continuous chain in the polymer molecule.

The term "backbone unit", as used herein, refers to a repeating moiety in a polymer that correlates to a monomer used to form the polymer.

The term "polymer", as used herein, is a molecule, which includes a plurality of backbone units, linked to one-another via linking moieties, and these terms are defined hereinabove.

As used herein, the term "alkyl" describes an aliphatic hydrocarbon that includes straight chain and branched chain groups. The alkyl may have 1-20 carbon atoms (C1-20 alkyl), 1-10 carbon atoms, 1-6 or 1-4 carbon atoms in the main (longest) chain thereof, and it may be branched or unbranched. For example, an alkyl is a low alkyl, having 1-4 carbon atoms (namely, methyl, ethyl, propyl and butyl). Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms.

The term "cycloalkyl" refers to an all-carbon monocyclic or fused ring (i.e., rings, which share an adjacent pair of carbon atoms), branched or unbranched group containing 3 or more carbon atoms, where one or more of the rings does not have a completely conjugated π-electron system, and may further be substituted or unsubstituted. Exemplary cycloalkyl groups include, for example, cyclopropyl, cyclobutyl, cyclopentyl, cyclohexyl or cyclododecyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and iso-propenyl. The alkenyl may be substituted or unsubstituted by one or more substituents.

The term "alkynyl", as defined herein, is an unsaturated alkyl having at least two carbon atoms and at least one carbon-carbon triple bond. The alkynyl may be substituted or unsubstituted by one or more substituents. An exemplary alkynyl is ethynyl, which is a radical of acetylene.

The term "heteroalicyclic", as used herein, describes a monocyclic or fused ring group having in the ring(s) one or more atoms, such as nitrogen, oxygen, silicon and sulfur. The rings may also have one or more double bonds. However, the rings do not have a completely conjugated π-electron system. The heteroalicyclic compounds may be substituted or unsubstituted. Representative examples of heteroalicyclics, include morpholine, piperidine, piperazine, tetrahydrofurane, tetrahydropyrane and the like.

The term "aryl" describes an all-carbon monocyclic or fused-ring polycyclic (i.e., rings which share adjacent pairs of carbon atoms) groups having a completely conjugated π-electron system. The aryl group may be substituted or unsubstituted by one or more substituents.

The term "heteroaryl" describes a monocyclic or fused ring (i.e., rings which share an adjacent pair of atoms) group having in the ring(s) one or more atoms, such as, for example, nitrogen, oxygen, silicon and sulfur and, in addition, having a completely conjugated π-electron system. Representative examples of heteroaryls include without limitation, triazole, tetrazole, triazine, tetrazine and the like.

The terms "azido" or "azide" describe a $—N_3$ group.

The terms "nitrile" or "cyano" describe a $—C{\equiv}N$ group.

The term "cyanate" describes a $—O—C{\equiv}N$ group.

The term "isocyanate" describes a $—N{=}C{=}O$ group.

The term "diazonium", as used herein, refers to $—N_2^+X^-$ ($—N^+{\equiv}NX^-$) group, where X is an inorganic or organic anion, such as a halogen.

The term "ethynyl" describes a $—C{\equiv}CH$ group.

As used herein, the term "hydrazine" describes a —NR'—NR"R'" group, wherein R', R" and R'" are each independently hydrogen, alkyl, cycloalkyl or aryl, as these terms are defined herein.

The term "hydrazide", as used herein, refers to a —C(=O)—NR'—NR"R'" group wherein R', R" and R'" are each independently hydrogen, alkyl, cycloalkyl or aryl, as these terms are defined herein.

As used herein, the term "amine" describes a —NR'R" group where each of R' and R" is independently hydrogen, alkyl, cycloalkyl, heteroalicyclic, aryl or heteroaryl, as these terms are defined herein.

The term "ethanolamine" describes a —NH—$CH_2$—$CH_2$—OH group.

The term "halide", as used herein, refers to the anion of a halo atom, i.e. $F^-$, $Cl^-$, $Br^-$ and $I^-$.

The term "halo" refers to F, Cl, Br and I atoms as substituents.

The terms "hydroxyl" or "hydroxy", as used herein, refer to an —OH group.

The term "alkoxy" refers to an —OR' group, wherein R' is as defined hereinabove.

The term "hydroxyalkyl," as used herein, refers to an alkyl group substituted with one hydroxy group, e.g., hydroxymethyl, para-hydroxyethyl and 4-hydroxypentyl.

The term "alkoxyalkyl," as used herein, refers to an alkyl group substituted with one alkoxy group, e.g., methoxymethyl, 2-methoxyethyl, 4-ethoxybutyl, n-propoxyethyl and tert-butylethyl.

The term "amide" describes a —NR'—C(=O)—R" or a —C(=O)—NR'R" end groups or a —NR'—C(=O)— linking moiety, where each of R' and R" is independently hydrogen, alkyl, cycloalkyl, heteroalicyclic, aryl or heteroaryl, as these terms are defined herein.

The term "imidate" describes a —C(N=R')O—R" group, where each of R' and R" is independently hydrogen, alkyl, cycloalkyl, heteroalicyclic, aryl or heteroaryl, as these terms are defined herein As used herein, the terms "carboxylate" or "ester" refer to an —C(=O)OR' group, where R' is as defined herein.

As used herein, the terms "carboxyl" or "carboxy" refer to an —C(=O)OH group.

The term "azo" or "diazo" describes an —N=NR' with R' as defined hereinabove.

As used herein, the phrase "moiety" describes a part, and preferably a major part of a chemical entity or compound, which typically has certain functionality or distinguishing features. In some embodiments, the term "moiety" also describes a part, and preferably a major part, of a chemical entity, such as a molecule or a group, which has underwent a chemical reaction and is now covalently linked to another molecular entity. This term is also used herein to define a radical of the indicated group, which substitutes a respective position of the skeleton of a compound.

It is expected that during the life of a patent maturing from this application, many relevant tetrazine-based energetic monomers and polymers, based thereon, will be uncovered, and the scope of the tetrazine-based energetic monomers and polymers is intended to include all such mutations a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges, as well as individual numerical values within that range. For example, description of a range, such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, material science, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately, or in any suitable sub-combination, or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

All materials were procured from Sigma-Aldrich Israel.
Thermal properties such as melting and decomposition points were measured on TA Q20 DSC instrument, using a heating rate of 10° C./min and by a Büchi B-540 Melting Point apparatus.

NMR measurements were performed at the ambient temperature on Bruker AVANCE 400 MHz spectrometer, using DMSO-$d_6$, $CD_3OD$ and $CD_3CN$ as solvents.

Mass spectrometry analyses were performed on ESI/MALDI Q-TOF Micromass spectrometer.

Calorimetric measurements were performed on Parr 6200 bomb calorimeter, equipped with a Parr 1104 bomb. The samples were placed in a stainless pan and burned in atmosphere of pure oxygen at 3.2 MPa pressure. Pellets of 1.0 g of benzoic acid were used as a reference standard.

Energetic parameters of the compounds were calculated using the EXPLO5 software, which is a thermochemical computer program that predicts the performance of ideal high explosives, propellants, and pyrotechnic mixtures on the basis of their chemical formulae, heat of formation, and density. As such, EXPLO5 is a useful tool in synthesis, formulation, and numerical modeling of energetic materials. Briefly, EXPLO5 calculates equilibrium composition and thermodynamic properties of state of products species at a specified temperature and pressure applying the free energy minimization techniques. These data, together with the Chapman-Jouguet detonation theory, enable calculation of detonation parameters such as detonation velocity, detonation pressure, detonation energy and the like. From the equilibrium composition and thermodynamic parameters of state along the isentropic expansion the program calculates the coefficients in Jones-Wilkins-Lee (JWL) equation of state by a JWL fitting program built in, and energy available for performing mechanical work. By combining thermodynamic properties of the products and conservation equations under constant pressure combustion conditions, the program predicts theoretical rocket performance (specific impulse, thrust coefficient, flow velocity, etc.), as well as the specific energy (or force, impetus) under constant volume combustion conditions. The program uses the Becker-Kistiakowsky-Wilson (BKW) equation of state for gaseous detonation products, the ideal gas and virial equations of state of gaseous combustion products, and the Murnaghan equation of states for condensed products.

Example 1

Synthesis and Analysis of Energetic Monomers

The following are synthetic procedure and analyses of exemplary energetic monomers, according to some embodiments of the present invention.

Synthesis of 1-(6-((3-amino-1H-1,2,4-triazol-5-yl)amino)-1,2,4,5-tetrazin-3-yl)-1H-1,2,4-triazole-3,5-diamine (EM1003)

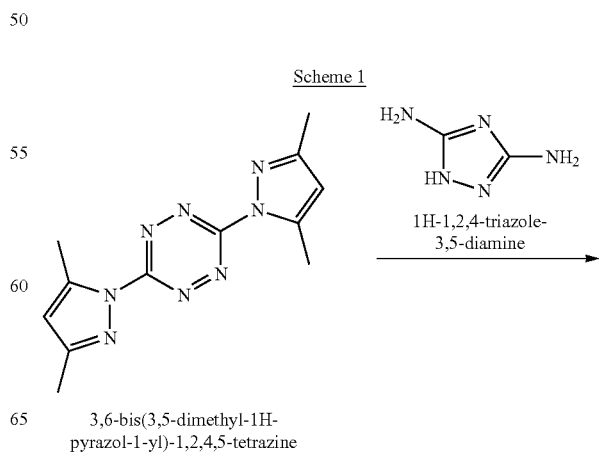

Scheme 1

3,6-bis(3,5-dimethyl-1H-pyrazol-1-yl)-1,2,4,5-tetrazine 1H-1,2,4-triazole-3,5-diamine

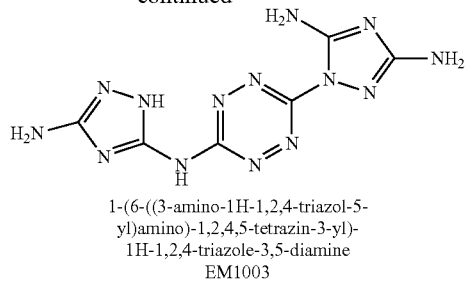

1-(6-((3-amino-1H-1,2,4-triazol-5-yl)amino)-1,2,4,5-tetrazin-3-yl)-1H-1,2,4-triazole-3,5-diamine
EM1003

A solid quantity of 3,5-diamine-1,2,4-triazol (3.2 grams, 32.3 mmol) was added to a solution of 3,6-bis(3,5-dimethyl-1H-pyrazol-1-yl)-1,2,4,5-tetrazine (BPT) (2.2 grams, 8.1 mmol) in sulfolane (50 mL) and the reaction mixture was heated at 140° C. for 24 hours. Thereafter, the reaction mixture was cooled to room temperature, DMSO (10 mL) was added, and the mixture was stirred for 1 hour. The formed precipitate was collected by filtration, washed with MeOH (80 mL) and dried under vacuum as a purple solid substance (EM1003). Yield 81.5% (1.82 grams, 6.6 mmol). $^1$H NMR (400 MHz, DMSO-$d_6$): δ 5.5 (2H, s), 6.0 (2H, br s) 7.16 (2H, s), 10.68 (1H, br s), 11.67 (1H, br s). $^{13}$C NMR (100 MHz, H$_2$SO$_4$+DMSO-$d_6$): δ 147.9, 152.9, 153.8, 155.0, 160.3, 163.8. DSC (5° C./min) 365° C. (decomp.). MS (ESI$^-$): m/z: 275 [M−H$^-$], (ESI+): m/z: 277 [M−H$^+$]. FTIR (ATR, cm$^{-1}$): 1626 (m), 1553 (m), 1468 (s), 1439 (m), 1354 (w), 1283 (w), 1117 (w), 1085 (w), 1049 (w), 1032 (w), 951 (w), 890 (w), 821 (w), 561 (m).

Synthesis of AA1085 6-(5-amino-3-azido-1H-1,2,4-triazol-1-yl)-N-(3-azido-1H-1,2,4-triazol-5-yl)-1,2,4,5-tetrazin-3-amine (AA1085)

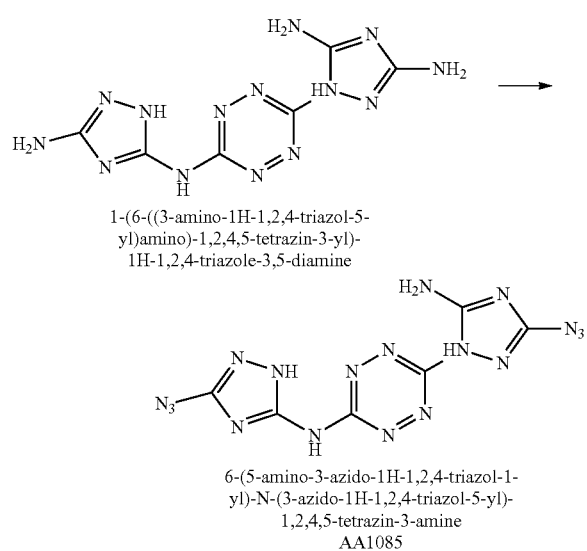

Scheme 2

1-(6-((3-amino-1H-1,2,4-triazol-5-yl)amino)-1,2,4,5-tetrazin-3-yl)-1H-1,2,4-triazole-3,5-diamine 6-(5-amino-3-azido-1H-1,2,4-triazol-1-yl)-N-(3-azido-1H-1,2,4-triazol-5-yl)-1,2,4,5-tetrazin-3-amine
AA1085

A solid quantity of 1-(6-((3-amino-1H-1,2,4-triazol-5-yl)amino)-1,2,4,5-tetrazin-3-yl)-1H-1,2,4-triazole-3,5-diamine (2 g, 7.28 mmol) was added to a solution of H$_2$SO$_4$ 30% (v/v) (43 ml) at 0° C. and the mixture was stirred for 20 minutes. A solution of aqueous NaNO$_2$ (2.03 grams, 29 mmol NaNO$_2$ in 2.5 ml of H$_2$O) was added dropwise and the solution was stirred for 1 hour. Aqueous solution of NaN$_3$ (15 ml, 5.08 g, 78 mmol) was added dropwise to the reaction solution at 0° C. and stirred 3 hours. The formed precipitate was collected by filtration, washed with H$_2$O (3×30 ml), MeOH (3×20 ml) and dried, yielding pure 6-(5-amino-3-azido-1H-1,2,4-triazol-1-yl)-N-(3-azido-1H-1,2,4-triazol-5-yl)-1,2,4,5-tetrazin-3-amine as a red solid ("AA1085", 2.28, 6.95 mmol, 95%). $^1$H NMR (400 MHz, DMSO-$d_6$): δ 7.7 (2H, s) 12.7 (1H, br s), 13.4 (1H, br s). $^{13}$C NMR (100 MHz, DMSO-$d_6$): δ 148.3, 154.8, 156.4, 157.3, 158.7. DSC (5° C./min) 212° C. (decomp.). MS (ESI$^-$): m/z: 327.2 [M−H$^-$]; (ESI$^+$): 329.3 [M+H$^-$]. FTIR (ATR, cm$^{-1}$): 3421 (w), 2145 (s), 1652 (m), 1541 (m), 1508 (m), 1456 (s), 1364 (m), 1222 (w), 1138 (w), 1104 (w), 1048 (w), 1014 (w), 951 (w), 742 (w), 554 (w), 458 (w). Bomb calorimetry: gross heat of 2,472 cal/g.

Synthesis of N$^5$,N$^{5'}$-(1,2,4,5-tetrazine-3,6-diyl)-bis(1H-1,2,4-triazole-3,5-diamine)(EM1004)

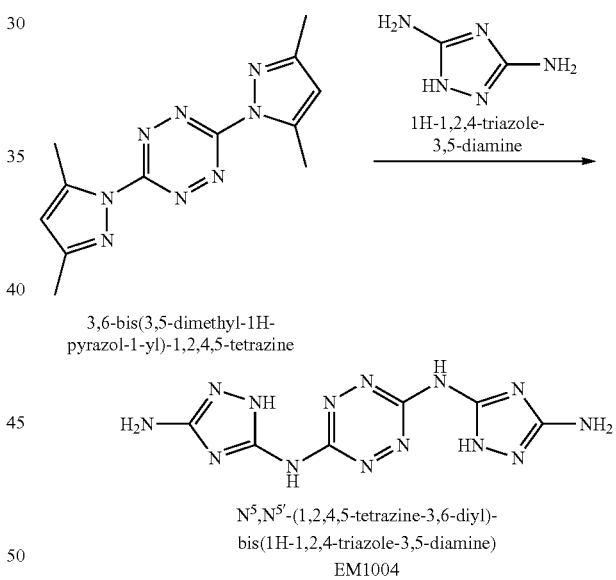

Scheme 3

3,6-bis(3,5-dimethyl-1H-pyrazol-1-yl)-1,2,4,5-tetrazine 1H-1,2,4-triazole-3,5-diamine N$^5$,N$^{5'}$-(1,2,4,5-tetrazine-3,6-diyl)-bis(1H-1,2,4-triazole-3,5-diamine)
EM1004

A solid quantity of 3,5-diamine-1,2,4-triazol (4 grams, 40.4 mmol) was added to a solution of 3,6-bis(3,5-dimethyl-1H-pyrazol-1-yl)-1,2,4,5-tetrazine (3 grams, 11.1 mmol) in sulfolane (70 mL) and the reaction mixture was heated at 210° C. in sand bath for 24 hours. Thereafter, the reaction mixture was cooled to room temperature, MeOH (15 mL) was added and the mixture was stirred for 1 hour. The formed precipitate was collected by filtration, washed with MeOH (80 mL) and dried under vacuum as a purple solid. Yield 84.5% (2.59 grams, 9.38 mmol). $^{13}$C NMR (100 MHz, H$_2$SO$_4$+DMSO-$d_6$): δ 147.5, 153.3, 160.8. DSC (5° C./min) 369° C. (decomp.). FTIR (ATR, cm$^{-1}$): 1610 (s), 1541 (s), 1439 (s), 1371 (m), 1333 (w), 1271 (m), 1097 (m), 1055 (s), 954 (s), 888 (w), 792 (m), 738 (m), 703 (m), 564 (m).

Synthesis of N³,N⁶-bis(3-azido-1H-1,2,4-triazol-5-yl)-1,2,4,5-tetrazine-3,6-diamine ("AA1095")

Scheme 4

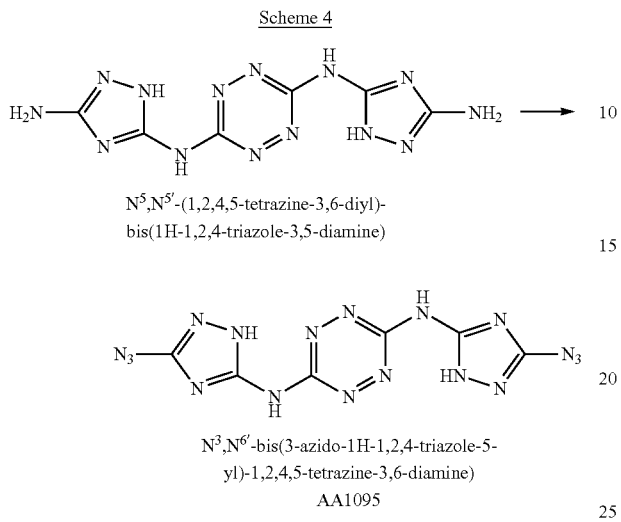

N⁵,N⁵'-(1,2,4,5-tetrazine-3,6-diyl)-
bis(1H-1,2,4-triazole-3,5-diamine)

N³,N⁶'-bis(3-azido-1H-1,2,4-triazole-5-
yl)-1,2,4,5-tetrazine-3,6-diamine)
AA1095

A solid quantity of N⁵,N⁵'-(1,2,4,5-tetrazine-3,6-diyl)bis(1H-1,2,4-triazole-3,5-diamine) (2 g, 7.28 mmol) was added to a solution of H₂SO₄ 30% (v/v) (43 ml) at 0° C. and the mixture was stirred for 20 minutes. A solution of aqueous NaNO₂ (2.05 grams, 29 mmol NaNO₂ in 2.5 ml H₂O) was added dropwise and the solution was stirred for 1 hour. Aqueous solution of NaN₃ (10 ml, 4.09 grams, 63 mmol) was added dropwise to the reaction solution at 0° C. and stirred 3 hours. The formed precipitate was collected by filtration, washed with H₂O (3×30 ml), MeOH (3×20 ml) and dried, yielding pure N³,N⁶-bis(3-azido-1H-1,2,4-triazol-5-yl)-1,2,4,5-tetrazine-3,6-diamine as a red solid ("AA1095", 1.97 g, 6 mmol, 82%). ¹H NMR (400 MHz, DMSO-d₆): δ 12.2 (2H, s), 13.2 (2H, s). ¹³C NMR (100 MHz, DMSO-d₆): δ 149.2, 154.6, 158.0. DSC (5° C./min) 203° C. (decomp.). MS (ESI⁻): m/z: 327.2 [M−H⁻]; (ESI⁺): 329.2 [M+H⁻]. FTIR (ATR, cm⁻¹): 3419 (w), 3325 (w), 2144 (m), 1615 (s), 1557 (s), 1541 (s), 1436 (s), 1363 (s), 1222 (w), 1138 (w), 1079 (w), 1053 (w), 1015 (w), 955 (w), 810 (w), 724 (w), 557 (w).

Proposed Synthesis of AA1086 (5-amino-1-(6-((3-cyano-1H-1,2,4-triazol-5-yl)amino)-1,2,4,5-tetrazin-3-yl)-1H-1,2,4-triazole-3-carbonitrile) ("AA1086")

Scheme 5

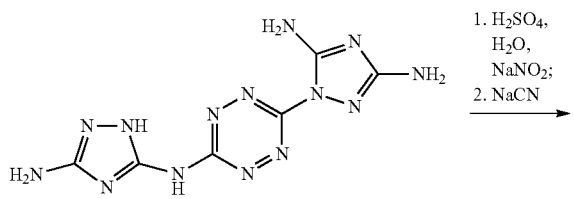

1. H₂SO₄, H₂O, NaNO₂;
2. NaCN

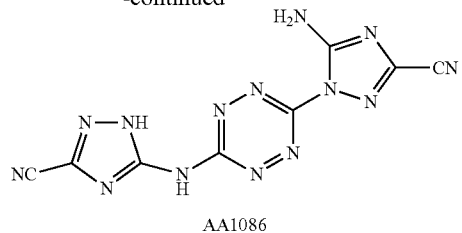

AA1086

1-(6-((3-amino-1H-1,2,4-triazol-5-yl)amino)-1,2,4,5-tetrazin-3-yl)-1H-1,2,4-triazole-3,5-diamine (1,025 mg, 3.71 mmol) is slowly added to a 4° C. cooled solution of concentrated H₂SO₄ (7 mL) in H₂O (20 mL) and stirred for 30 minutes. Thereafter, a solution of NaNO₂ (640 mg, 9.27 mmol) in H₂O (3 mL) is added dropwise, and the reaction mixture is stirred at 4° C. for 1 hour and then added over 30 minutes to a cooled solution of NaCN (2,646 mg, 54 mmol) in H₂O (100 mL). The resulting reaction mixture is stirred overnight at room temperature and the formed precipitate is collected by filtration. The crude solid is dissolved in a minimal amount of DMF, filtered at room temperature, cold water is added to the DMF solution until precipitate is obtained. The aqueous suspension is stirred for 1 hour and filtered. The final solid is washed twice with H₂O and dried under vacuum, yielding 5-amino-1-(6-((3-cyano-1H-1,2,4-triazol-5-yl)amino)-1,2,4,5-tetrazin-3-yl)-1H-1,2,4-triazole-3-carbo-nitrile ("AA1086").

Proposed Synthesis of AA1200 (6-(5-amino-3-hydrazinyl-1H-1,2,4-triazol-1-yl)-N-(3-hydrazinyl-1H-1,2,4-triazol-5-yl)-1,2,4,5-tetrazin-3-amine) ("AA1200")

Scheme 6

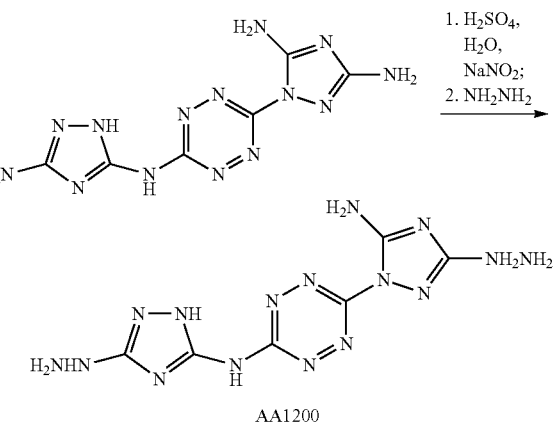

AA1200

1-(6-((3-amino-1H-1,2,4-triazol-5-yl)amino)-1,2,4,5-tetrazin-3-yl)-1H-1,2,4-triazole-3,5-diamine (1,025 mg, 3.71 mmol) is slowly added to a 4° C. cooled solution of concentrated H₂SO₄ (7 mL) in H₂O (20 mL) and stirred for 30 minutes. Thereafter, a solution of NaNO₂ (640 mg, 9.27 mmol) in H₂O (3 mL) is added dropwise, and the reaction mixture is stirred at 4° C. for 1 hour and then added over 30 minutes to a solution of aqueous hydrazine. The resulting reaction mixture is stirred for overnight at room temperature and formed precipitate is collected by filtration, yielding (6-(5-amino-3-hydrazinyl-1H-1,2,4-triazol-1-yl)-N-(3-hydrazinyl-1H-1,2,4-triazol-5-yl)-1,2,4,5-tetrazin-3-amine) ("AA1200").

Proposed Synthesis of (6-(3,5-dihydrazinyl-1H-1,2,4-triazol-1-yl)-N-(3-hydrazinyl-1H-1,2,4-triazol-5-yl)-1,2,4,5-tetrazin-3-amine) ("AA1201")

Scheme 7

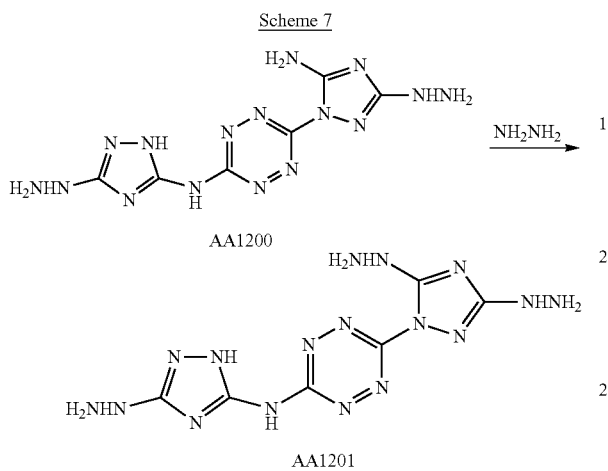

(6-(5-amino-3-hydrazinyl-1H-1,2,4-triazol-1-yl)-N-(3-hydrazinyl-1H-1,2,4-triazol-5-yl)-1,2,4,5-tetrazin-3-amine) ("AA1200") is stirred overnight in a solution of aqueous hydrazine at room temperature. The resulting reaction mixture is concentrated under vacuum to a minimum volume and formed precipitate is collected by filtration and dried, yielding (6-(3,5-dihydrazinyl-1H-1,2,4-triazol-1-yl)-N-(3-hydrazinyl-1H-1,2,4-triazol-5-yl)-1,2,4,5-tetrazin-3-amine) ("AA1201").

Proposed Synthesis of ((1,2,4,5-tetrazine-3,6-diyl)bis(hydrazine-2,1-diyl))-bis(hydrazinylmethaniminium)chloride ("AA1202")

Scheme 8

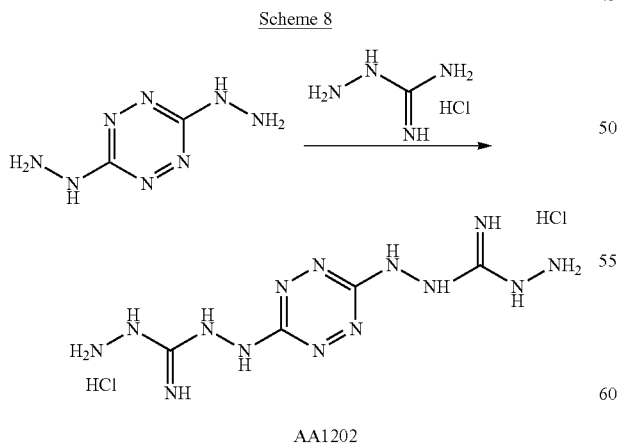

To a solution of 3,6-dihydrazinyl-1,2,4,5-tetrazine (30 mmol) in methanol (50 mL) amino(hydrazinyl)methaniminium chloride (70 mmole) is added at room temperature and the reaction mixture is heated to reflux for overnight under nitrogen atmosphere. After cooling to room temperature, the solvent volume is reduced by 50% and diethylether (50 mL) is added. The formed precipitate is filtered and dried under vacuum to afford ((1,2,4,5-tetrazine-3,6-diyl)bis(hydrazine-2,1-diyl))-bis(hydrazinylmethaniminium) chloride ("AA1202") monomer.

Proposed Synthesis of 2-((3-azido-1-(6-((3-azido-1-(2-hydroxyethyl)-1H-1,2,4-triazol-5-yl)amino)-1,2,4,5-tetrazin-3-yl)-1H-1,2,4-triazol-5-yl)amino)ethan-1-ol ("AA1600")

Scheme 9

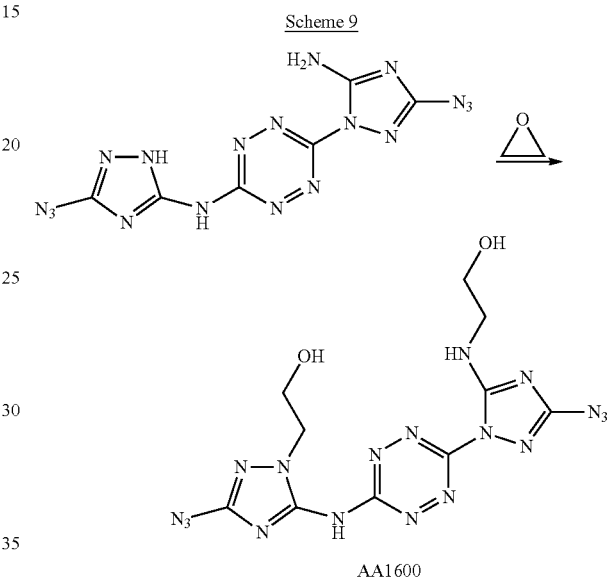

To a dispersion of 6-(5-amino-3-azido-1H-1,2,4-triazol-1-yl)-N-(3-azido-1H-1,2,4-triazol-5-yl)-1,2,4,5-tetrazin-3-amine in DMF, NaHCO$_3$ powder is added and the reaction mixture is stirred for 1 hour at room temperature. Thereafter, gaseous ethylene oxide is bubbled through the reaction mixture and the reaction mixture is heated to 70° C. for 4 hours. After cooling to room temperature, the volume of the reaction mixture is reduced by 80% and diethylether is added. The formed precipitate is filtered and dried to afford 2-((3-azido-1-(6-((3-azido-1-(2-hydroxyethyl)-1H-1,2,4-triazol-5-yl)amino)-1,2,4,5-tetrazin-3-yl)-1H-1,2,4-triazol-5-yl)amino)ethan-1-ol ("AA1600") monomer.

Proposed Synthesis of 2,2'-(((1,2,4,5-tetrazine-3,6-diyl)bis(azanediyl))bis(2H-tetrazole-5,2-diyl))-bis(ethan-1-ol) ("AA1601")

Scheme 10

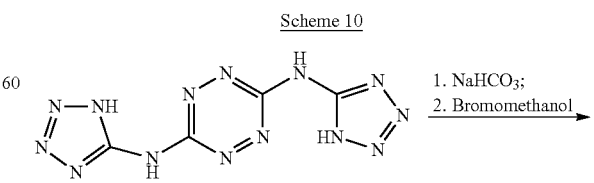

$N^3,N^6$-di(1H-tetrazol-5-yl)-1,2,4,5-tetrazine-3,6-diamine

47

-continued

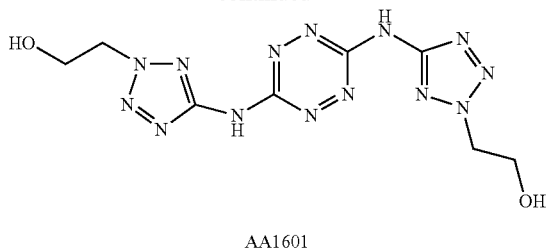

AA1601

To a dispersion of N3,N6-di(1H-tetrazol-5-yl)-1,2,4,5-tetrazine-3,6-diamine in DMF, NaHCO$_3$ powder is added and the reaction mixture is stirred for 1 hour at room temperature. Thereafter, 1,2-bromoethanol is added slowly and the reaction mixture is heated to 70° C. for 2 hours. After cooling to room temperature, the volume of the reaction mixture is reduced by 80% and water is added. The formed precipitate is filtered and dried to afford 2,2'-(((1,2,4,5-tetrazine-3,6-diyl)bis(azanediyl))bis(2H-tetrazole-5,2-diyl))-bis(ethan-1-ol) ("AA1601").

Proposed Synthesis of (((1,2,4,5-tetrazine-3,6-diyl)bis(azanediyl))bis(1H-1,2,4-triazole-5,3-diyl))dimethanol ("AA1700")

Scheme 11

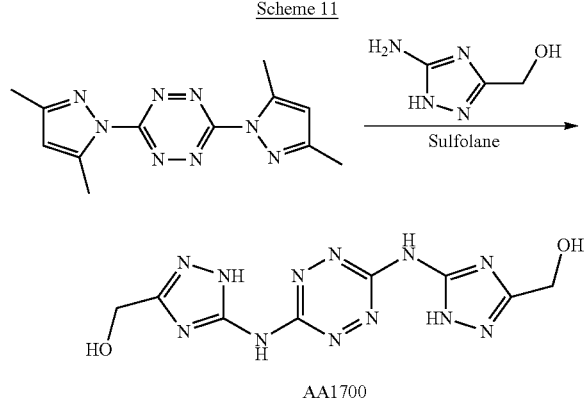

AA1700

A suspension of 3,6-bis(3,5-dimethyl-1H-pyrazol-1-yl)-1,2,4,5-tetrazine (3.74 g, 0.014 mol) and (5-amino-1H-1,2,4-triazol-3-yl)methanol (4.0 grams, 0.035 mol) in sulfolane (60 mL) is heated to about 135° C. for 24 hours. After cooling to room temperature, ethyl acetate (150 mL) is added to the reaction mixture and the formed precipitate is filtered, washed with MeOH (2×150 mL) and dried under vacuum. Thereafter, the solid is dissolved in aqueous NaHCO$_3$ (10%) under heating to 50° C. Activated carbon powder (100 mg) is added and the mixture is heated to 50° C. for 1 hour. The resulting mixture is filtered and HCl solution (10%) and added to filtrate, in order to adjust the pH to about 1.5. The formed precipitate is filtered, washed with H$_2$O (2×20 mL) and dried under vacuum to afford ((1,2,4,5-tetrazine-3,6-diyl)-bis(azanediyl))-bis(1H-1,2,4-triazole-5,3-diyl))dimethanol ("AA1700").

48

Synthesis of N$^3$,N$^6$-di(1H-1,2,4-triazol-5-yl)-1,2,4,5-tetrazine-3,6-diamine (EM1005)

Scheme 12

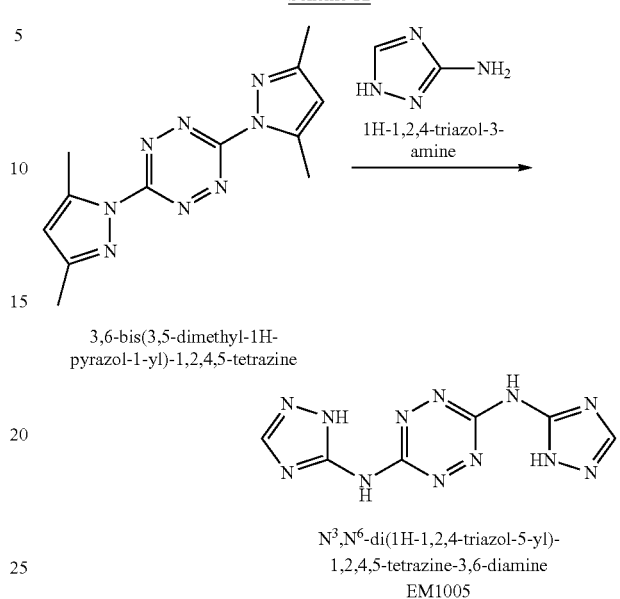

3,6-bis(3,5-dimethyl-1H-pyrazol-1-yl)-1,2,4,5-tetrazine 1H-1,2,4-triazol-3-amine N$^3$,N$^6$-di(1H-1,2,4-triazol-5-yl)-1,2,4,5-tetrazine-3,6-diamine
EM1005

A solid quantity of 1H-1,2,4-triazol-5-amine (4.23 grams, 50.31 mmol) was added to a solution of 3,6-bis(3,5-dimethyl-1H-pyrazol-1-yl)-1,2,4,5-tetrazine (6.46 grams, 23.90 mmol) in sulfolane (150 mL) and the reaction mixture was heated at 135° C. for 24 hours. Thereafter, the reaction mixture was cooled to room temperature, DMF (150 mL) was added and the mixture was stirred for 1 hour. The formed precipitate was collected by filtration, washed with MeOH (3×80 mL) and dried under vacuum, yielding pure N$^3$,N$^6$-di(1H-1,2,4-triazol-5-yl)-1,2,4,5-tetrazine-3,6-diamine as an orange solid (4.77 g, 81%). DSC (10° C./min) 332° C. (decomp.). HRMS (ESI$^-$): m/z: 245.0697 [M–H$^-$]. Elemental Analysis: calcd. (%) for C$_6$H$_6$N$_{12}$: C, 29.27, N, 68.27, H, 2.46; found: C, 29.92, N, 68.73, H, 2.55. FTIR (ATR): ν 2807 (m), 2359 (w), 1597 (s), 1542 (s), 1486 (s), 1434 (s), 1312 (m), 1268 (s), 1207 (w), 1062 (s), 1047 (s), 1027 (s), 962 (s), 896 (s), 763 (m), 719 (s), 649 (m), 557 (s). Due to a very low solubility of the compound in all tested organic solvents, the free base was converted into the corresponding nitrate salts for further analysis. $^1$H NMR (400 MHz, DMSO-d$_6$): δ 8.65 (s), 11.35 (br s). $^{13}$C NMR (100 MHz, DMSO-d$_6$): δ 143.4, 150.1, 158.6. FTIR (ATR, cm$^{-1}$): ν 2943 (w), 1697 (s), 1621 (s), 1551 (s), 1407 (s), 1303 (s), 1060 (s), 1041 (s), 999 (s), 937 (s), 855 (s), 713 (s), 557 (s).

Synthesis of (((1,2,4,5-tetrazine-3,6-diyl)bis(azanediyl))bis(1H-1,2,4-triazole-5,3-diyl))dimethanol ("AA1700")

Scheme 13

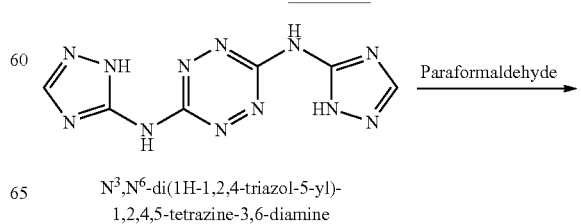

N$^3$,N$^6$-di(1H-1,2,4-triazol-5-yl)-1,2,4,5-tetrazine-3,6-diamine

Paraformaldehyde

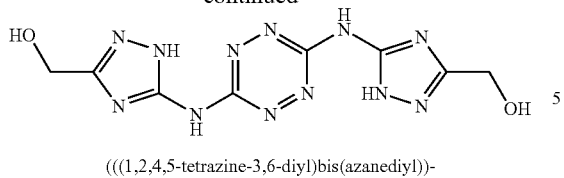

(((1,2,4,5-tetrazine-3,6-diyl)bis(azanediyl))-
bis(1H-1,2,4-triazole,5,3-diyl))dimethanol
AA1700

A solid quantity of paraformaldehyde (277 mg, 9.22 mmol) was added to a solution of $N^3,N^6$-di(1H-1,2,4-triazol-5-yl)-1,2,4,5-tetrazine-3,6-diamine (453 mg, 1.84 mmol) in acetic acid (20 mL) and the reaction mixture was stirred and heated at 95° C. After 2.5 hours, paraformaldehyde (245 mg, 8.15 mmol) was added and the reaction mixture was stirred at the same temperature for 22 hours. The reaction mixture was cooled to room temperature and the precipitate was collected by filtration, washed with H₂O and MeOH and dried under vacuum, yielding (((1,2,4,5-tetrazine-3,6-diyl)bis(azanediyl))bis(1H-1,2,4-triazole-5,3-diyl))dimethanol ("AA1700") as an orange solid (273 mg, 0.89 mmole, 48%). $^1$H NMR (400 MHz, DMSO-d₆): δ 10.68 (s, 2H), 8.46 (s, 2H), 7.02 (t, 2H), 5.39 (d, 4H). $^{13}$C NMR (100 MHz, DMSO-d₆): δ 71.1, 143.5, 157.1, 159.2. MS (ESI⁻): m/z: 305 [M–H⁻].

Synthesis of Monomers AS-1271 and AS-1272

Scheme 14

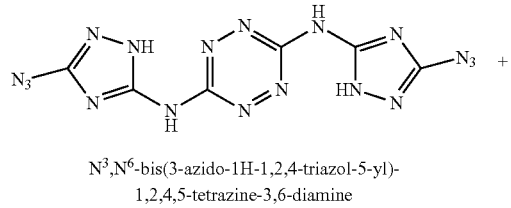

$N^3,N^6$-bis(3-azido-1H-1,2,4-triazol-5-yl)-
1,2,4,5-tetrazine-3,6-diamine

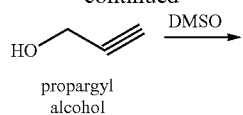

propargyl
alcohol

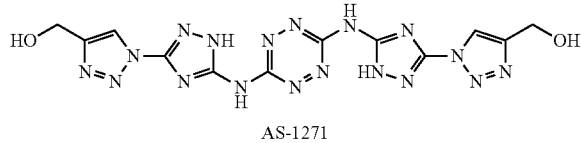

AS-1271

+

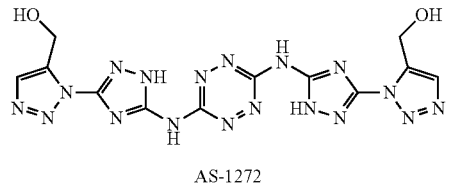

AS-1272

To a solution of $N^3,N^6$-bis(3-azido-1H-1,2,4-triazol-5-yl)-1,2,4,5-tetrazine-3,6-diamine (53 mg, 0.16 mmol) in DMSO (3 ml) propargyl alcohol (250 μl, 4.3 mmol) was added and the reaction mixture was heated at 90° C. for 24 hours. Thereafter, the reaction mixture was cooled to room temperature and H₂O (15 ml) was added. The formed precipitate was collected by filtration, washed with water and vacuum dried to yield a mixture of target isomeric monomers AS-1271 and AS-1272 (ratio between isomers was 1:3, respectively). MS (ESI⁺): m/z: 439.3. $^1$H NMR (400 MHz, DMSO-d₆): isomer AS-1271 (33%): δ 4.6 (4H, s) 5.3 (2H, s), 8.4 (2H, s), 12.5 (2H, s); isomer AS-1272 (67%): δ 4.8 (4H, s) 5.6 (2H, s), 7.8 (2H, s), 12.5 (2H, s).

Synthesis of Monomer TP-147

Scheme 15

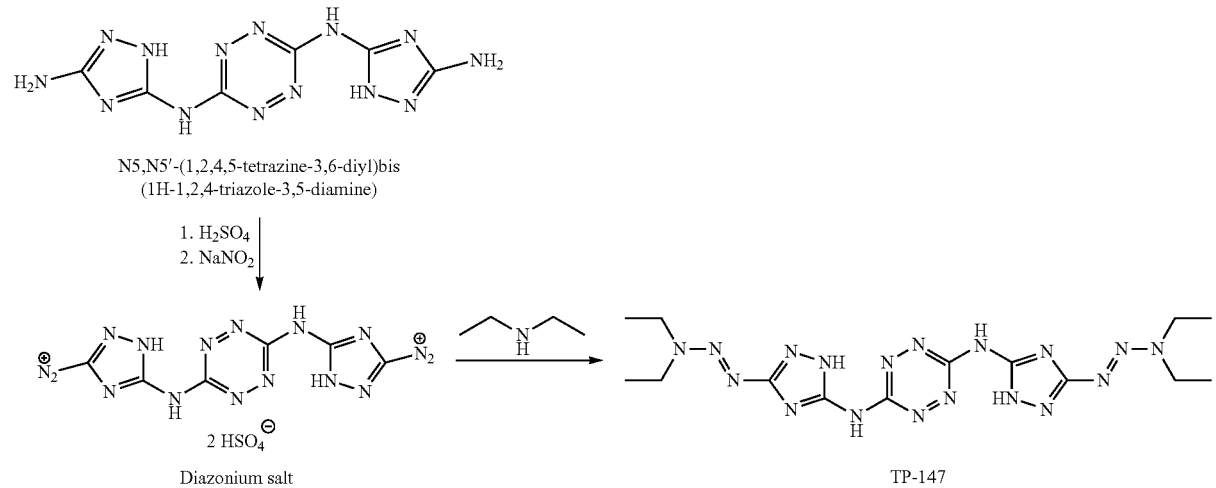

To a solution of $N^5,N^{5'}$-(1,2,4,5-tetrazine-3,6-diyl)bis(1H-1,2,4-triazole-3,5-diamine) (206 mg, 0.74 mmol) in concentrated $H_2SO_4$ (2 mL, 98%) $H_2O$ (3 mL) was added dropwise and the mixture was stirred for 1 h at 0° C. Then, to this mixture an aqueous solution of $NaNO_2$ (200 mg, 2.85 mmol, 0.5 ml) was added dropwise, while the reaction temperature was kept below 5° C. and the mixture was stirred for 1 h. After that time, $H_2O$ (20 mL) was added to the reaction mixture and formed diazonium salt (highly sensitive compound) was collected by filtration. Subsequently, wet diazonium salt was added to a solution of diethylamine (0.5 ml, 4.84 mmol) in water (30 mL) and the mixture was stirred at room temperature for 5 h. After that time, acetic acid (6 mL) was added to the reaction mixture and formed precipitate was filtered out, washed with acetonitrile (3×20 mL) and vacuum dried to yield monomer TP-147. MS (ESI+): m/z: 445.5, (ESI−): m/z 443.4. $^{13}C$ NMR (100 MHz, DMSO-$d_6$) δ 161.5, 158.9, 153, 49.2, 41.3, 14.1, 10.5. FTIR (ATR): 1594 (s), 1557 (w), 1541 (w), 1472 (s), 1434 (m), 1334 (s), 1241 (m), 1224 (m), 1072 (m), 1050 (s), 951 (m), 733 (m), 656 (m), 557 (s).

Table 1 presents the structure of the exemplary energetic monomers presented hereinabove.

TABLE 1

| Compound Ref. | Structure | N:C ratio |
| --- | --- | --- |
| AA1085 | 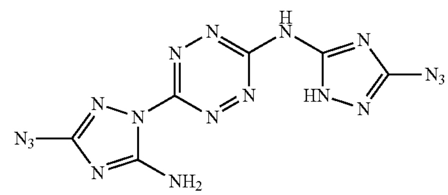 [SMILES: [N-]=[N+]=Nc1n[nH]c(Nc2nnc(-n3nc(N=[N+]=[N-])nc3N)nn2)n1] | 3 (18:6) |
| AA1086 | 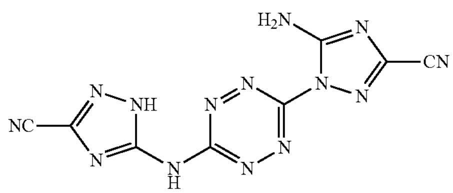 [SMILES: N#Cc1n[nH]c(Nc2nnc(-n3nc(C#N)nc3N)nn2)n1] | 1.8 (14:8) |
| AA1200 | 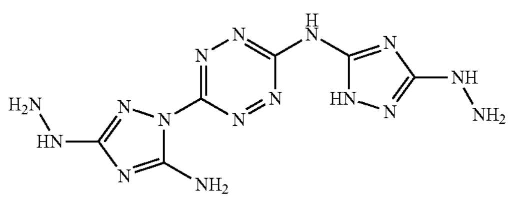 [SMILES: NNc1n[nH]c(Nc2nnc(-n3nc(NN)nc3N)nn2)n1] | 2.7 (16:6) |
| AA1201 | 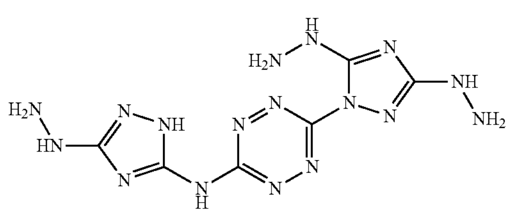 [SMILES: NNc1n[nH]c(Nc2nnc(-n3nc(NN)nc3NN)nn2)n1] | 2.8 (17:6) |
| AA1202 | 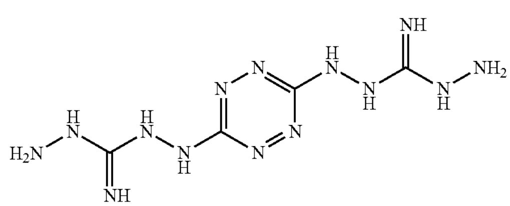 [SMILES: N=C(NN)NNc1nnc(NNC(=N)NN)nn1] | 3.5 (14:4) |

TABLE 1-continued

| Compound Ref. | Structure | N:C ratio |
|---|---|---|
| AA1600 | 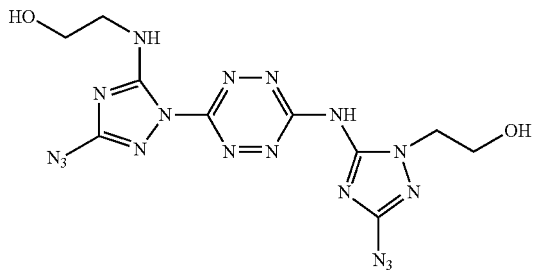 [SMILES: [N-]=[N+]=Nc1nc(Nc2nnc(-n3nc(N=[N+]=[N-])nc3NCCO)nn2)n(CCO)n1] | 1.8 (18:10) |
| AA1601 | 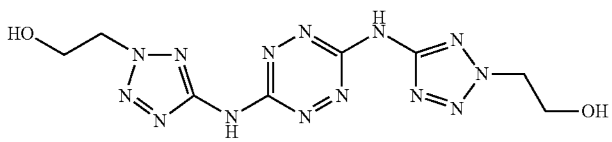 [SMILES: OCCn1nnc(Nc2nnc(Nc3nnn(CCO)n3)nn2)n1] | 1.8 (14:8) |
| AA1700 | 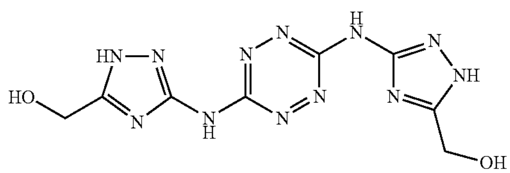 [SMILES: OCc1nc(Nc2nnc(Nc3n[nH]c(CO)n3)nn2)n[nH]1] | 1.5 (12:8) |
| AA1701 | 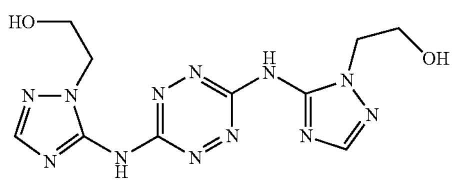 [SMILES: OCCn1ncnc1Nc1nnc(Nc2ncnn2CCO)nn1] | 1.2 (12:10) |
| EM1003 | 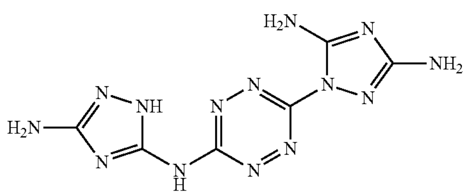 [SMILES: Nc1n[nH]c(Nc2nnc(-n3nc(N)nc3N)nn2)n1] | 2.3 (14:6) |
| EM1004 | 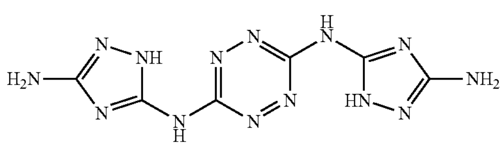 [SMILES: Nc1n[nH]c(Nc2nnc(Nc3nc(N)n[nH]3)nn2)n1] | 2.3 (14:6) |
| EM1005 | 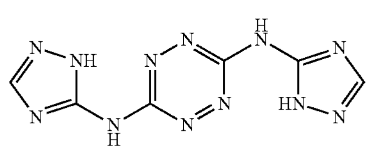 [SMILES: c1n[nH]c(Nc2nnc(Nc3ncn[nH]3)nn2)n1] | 2 (12:6) |
| EM1006 | 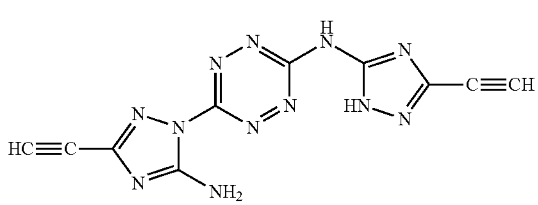 [SMILES: C#Cc1n[nH]c(Nc2nnc(-n3nc(C#C)nc3N)nn2)n1] | 1.2 (12:10) |

TABLE 1-continued
| Compound Ref. | Structure | N:C ratio |
|---|---|---|
| EM1007 | 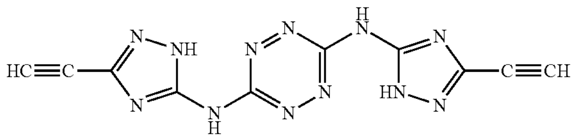 [SMILES: C#Cc1n[nH]c(Nc2nnc(Nc3nc(C#C)n[nH]3)nn2)n1] | 1.2 (12:10) |
| EM1008 | 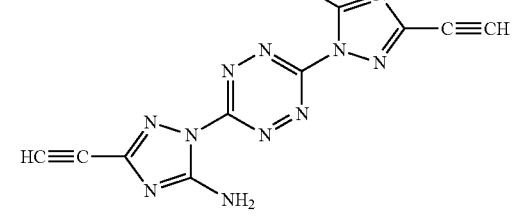 | 1.2 (12:10) |
| EM1009 | 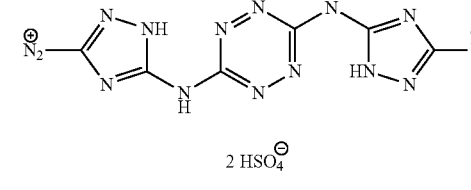 | 2.7 (16:6) |
| EM1010 | 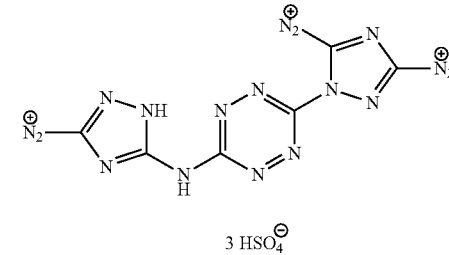 | 2.8 (17:6) |
| AA1095 | 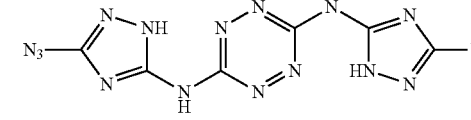 | 2.3 (14:6) |
| AA1271 | 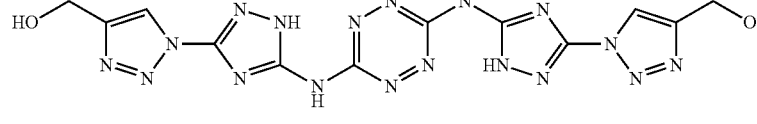 | 1.6 (18:11) |
| AA1272 | 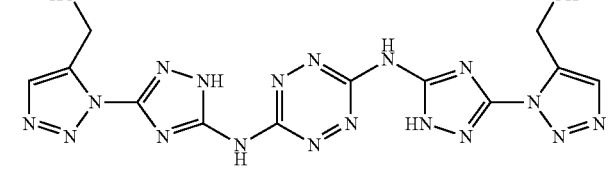 | 1.5 (18:12) |
| TP147 | 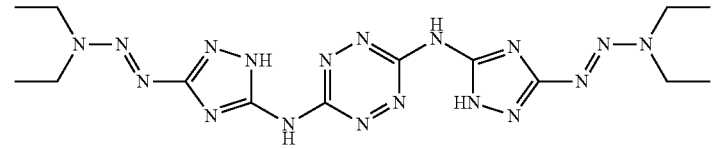 [SMILES: CCN(CC)/N=N/c1n[nH]c(Nc2nnc(Nc3nc(/N=N/N(CC)CC)n[nH]3)nn2)n1] | 1.3 (18:14) |

Example 2

Copper Catalyzed "Click" Chemistry Polymerization

The following presents exemplary syntheses of an exemplary class of energetic polymers, based on Cu-catalyzed "click" chemistry polymerization.

General Procedure

The schemes below present a general copper-catalyzed polymerization of bis-azide monomers with bis-cyanide (Scheme 8) and bis-alkynyl (Scheme 9) monomers, wherein Y and Z can each be independently alkyl, aryl, heterocyclic, heteroaryl, substituted 1,2,4,5-tetrazine and the like.

Scheme 16

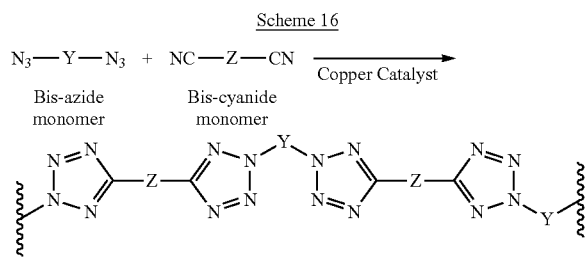

Scheme 17

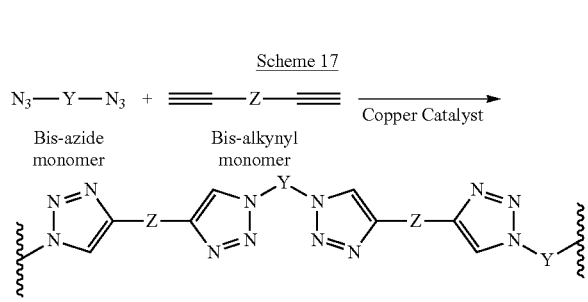

Following the rationale presented hereinabove, the schemes below present additional embodiments of a general copper-catalyzed click-chemistry polymerization:

Scheme 18

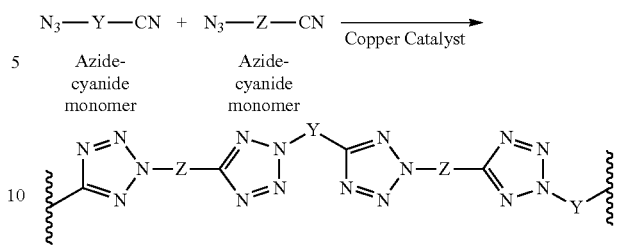

and

Scheme 19

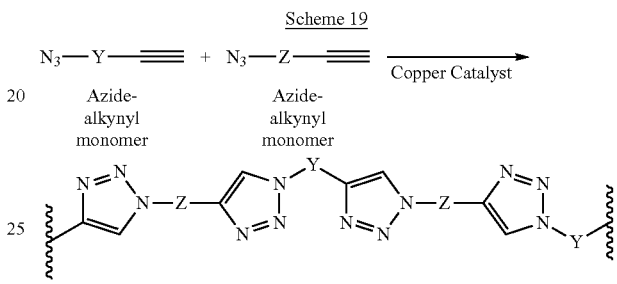

wherein Y and Z can each be independently alkyl, aryl, heterocyclic, heteroaryl, substituted 1,2,4,5-tetrazine and the like, and Y and Z may be identical.

Synthesis of an Exemplary Polymer TAUP133

The scheme below is proposed as a schematic synthetic procedure for the preparation of an exemplary energetic N-(3-(5-(4-(2-(5-amino-1-(6-((3-methyl-1H-1,2,4-triazol-5-yl)amino)-1,2,4,5-tetrazin-3-yl)-1H-1,2,4-triazol-3-yl)-2H-tetrazol-5-yl)butyl)-2H-tetrazol-2-yl)-1H-1,2,4-triazol-5-yl)-6-(5-amino-3-azido-1H-1,2,4-triazol-1-yl)-1,2,4,5-tetrazin-3-amine ("TAUP133") polymer from the exemplary 6-(5-amino-3-azido-1H-1,2,4-triazol-1-yl)-N-(3-azido-1H-1,2,4-triazol-5-yl)-1,2,4,5-tetrazin-3-amine ("AA1085") monomer and adiponitrile, in a copper-catalyzed "click" polymerization procedure.

Scheme 20

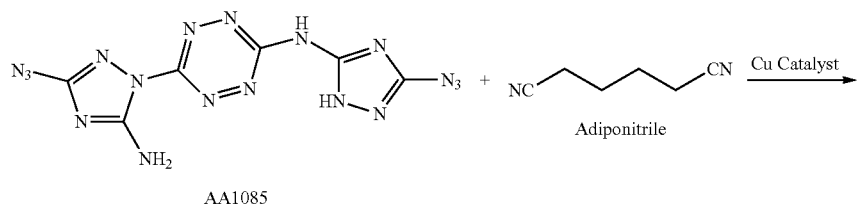

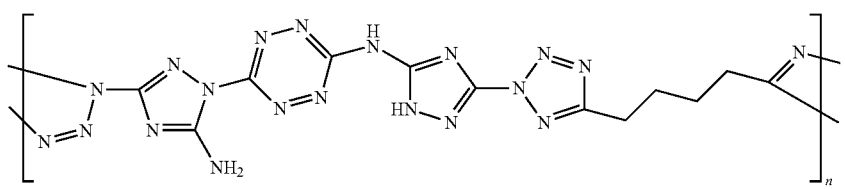

TAUP133

The procedure may follow reactions such as presented, for example, in Binder, W. H. et al. [*Macromol. Rapid Commun.* 2007, 28, pp. 15-54] and Terao, J. et al. [*Chemical Communications,* 2012, 48(10), pp. 1577-1579].

An exemplary 11-mer TAUP133 compound is characterized by chemical formula $C_{66}H_{64}N_{118}$; molecular weight 2,510.1 g/mol; calculated heat of formation ($\Delta H_f$) of 8,817.4 kJ/mol; calculated density of 1.73 $g/cm^3$; and calculated velocity of detonation (cVD) of 8,031 m/sec.

Comparatively, for n=1 the cVD is 11,072 m/sec, for n=2 the cVD is 8,720 m/sec, for n=3 the cVD is 8,150 m/sec and for n=4 the cVD is 8,057 m/sec.

Synthesis of an Exemplary Polymer TAUP183

The scheme below is proposed as a schematic synthetic procedure for the preparation of an exemplary energetic 5-amino-1-(6-((3-(2-(4-(5-(5-amino-1-(6-((3-methyl-1H-1, 2,4-triazol-5-yl)amino)-1,2,4,5-tetrazin-3-yl)-1H-1,2,4-triazol-3-yl)-2H-tetrazol-2-yl)-butyl)-2H-tetrazol-5-yl)-1H-1, 2,4-triazol-5-yl)amino)-1,2,4,5-tetrazin-3-yl)-1H-1,2,4-triazole-3-carbonitrile ("TAUP183") polymer from the exemplary 5-amino-1-(6-((3-cyano-1H-1,2,4-triazol-5-yl) amino)-1,2,4,5-tetrazin-3-yl)-1H-1,2,4-triazole-3-carbonitrile ("AA1086") monomer and 1,4-diazidobutane, using copper-catalyzed "click" polymerization.

Scheme 21

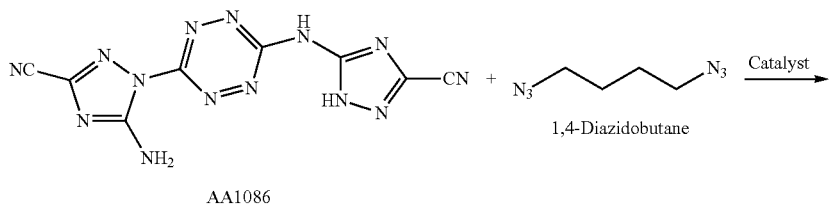

AA1086    1,4-Diazidobutane

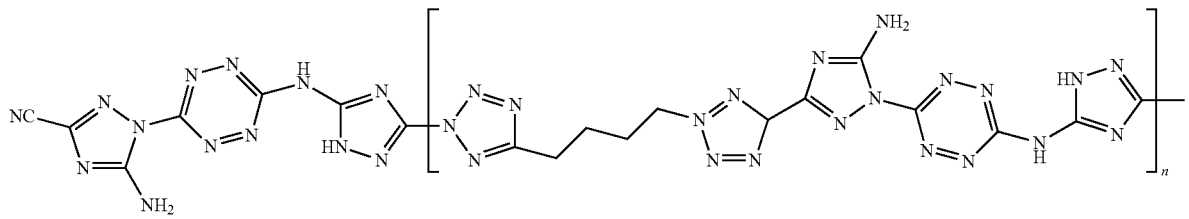

TAUP183

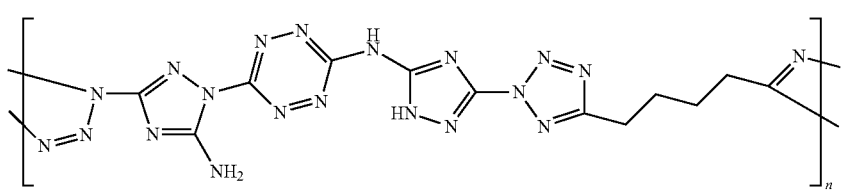

TAUP183

Synthesis of Polymer AS2-007

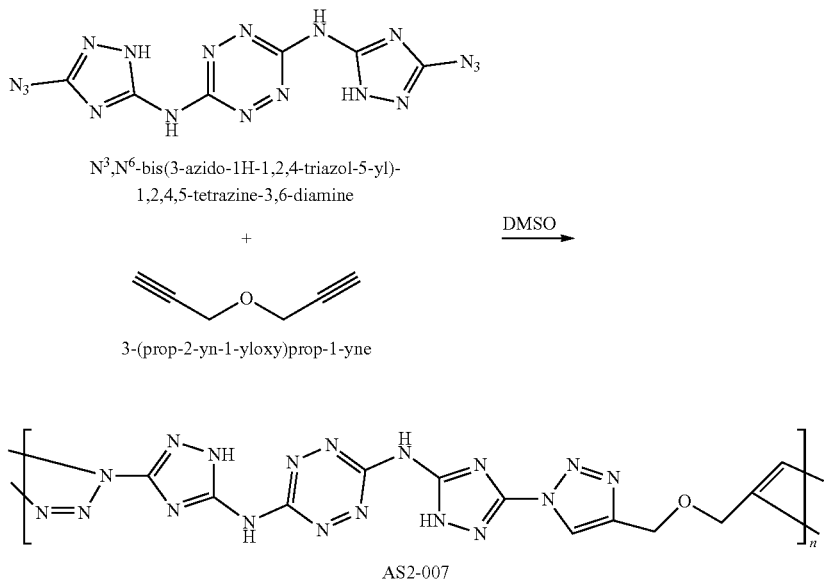

Scheme 22

To a solution of N³,N⁶-bis(3-azido-1H-1,2,4-triazol-5-yl)-1,2,4,5-tetrazine-3,6-diamine (303 mg, 0.92 mmol) in DMSO (12 mL) propargyl ether (105 µl, 1.02 mmol) was added at room temperature and the reaction mixture was heated at 110° C. for 20 days. After that time, the reaction mixture was cooled to room temperature, ethyl acetate (60 mL) was added and formed precipitate was filtered out, washed with acetonitrile (3×20 mL) and vacuum dried to yield polymer AS2-007 (128 mg). FTIR (ATR): 3247 (w), 1607 (s), 1574 (m), 1531 (m), 1474 (m), 1436 (s), 1364 (m), 1292 (m), 1243 (m), 1178 (w), 1108 (w), 1070 (m), 1046 (s), 974 (m), 955 (m), 882 (w), 838 (w), 761 (w), 728 (s), 657 (m), 558 (s).

Synthesis of Polymer AS2-008

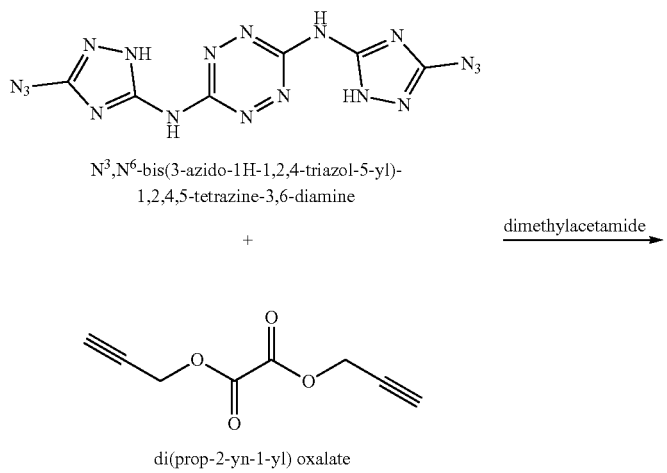

Scheme 23

-continued

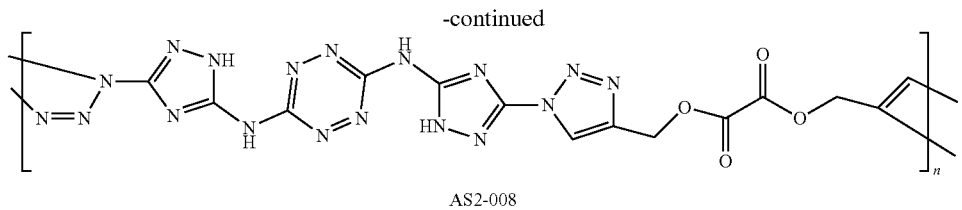

AS2-008

To a solution of N³,N⁶-bis(3-azido-1H-1,2,4-triazol-5-yl)-1,2,4,5-tetrazine-3,6-diamine (100 mg, 0.3 mmol) in dimethylacetamide (6 mL) a solution of di(prop-2-yn-1-yl) oxalate (68 mg, 0.4 mmol) in dimethylacetamide (2 mL) was added at room temperature and the reaction mixture was heated at 65° C. for 18 days. Thereafter, the reaction mixture was cooled to room temperature, ethyl acetate (15 mL) was added and formed precipitate was filtered out, washed with acetonitrile (3×20 mL) and vacuum dried to yield polymer AS2-008.

Example 3

Formaldehyde-Based Coupling Polymerization

The following presents an exemplary synthesis of an exemplary class of energetic polymers, based on a coupling polymerization reaction with formaldehyde.

General Procedure:

The scheme below presents a general polymerization of formaldehyde with bis-hydrazo monomers, wherein Z can be alkyl, aryl, heterocyclic, heteroaryl, substituted 1,2,4,5-tetrazine and the like.

Scheme 24

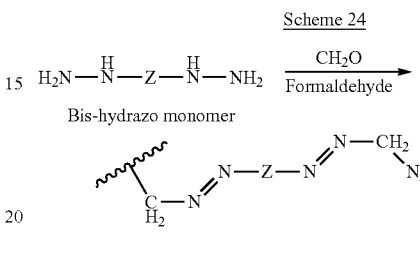

Bis-hydrazo monomer

Synthesis of an Exemplary Polymer TAUP2000

The scheme below is proposed as a schematic synthetic procedure for the preparation of an exemplary energetic N-(3-(((1E)-(((5-amino-1-(6-((3-((E)-ethyldiazenyl)-1H-1,2,4-triazol-5-yl)amino)-1,2,4,5-tetrazin-3-yl)-1H-1,2,4-triazol-3-yl)diazenyl)methyl)-diazenyl)-1H-1,2,4-triazol-5-yl)-6-(5-amino-3-(methyldiazenyl)-1H-1,2,4-triazol-1-yl)-1,2,4,5-tetrazin-3-amine ("TAUP2000") polymer from the exemplary 6-(5-amino-3-hydrazinyl-1H-1,2,4-triazol-1-yl)-N-(3-hydrazinyl-1H-1,2,4-triazol-5-yl)-1,2,4,5-tetrazin-3-amine ("AA1200") monomer and formaldehyde.

Scheme 25

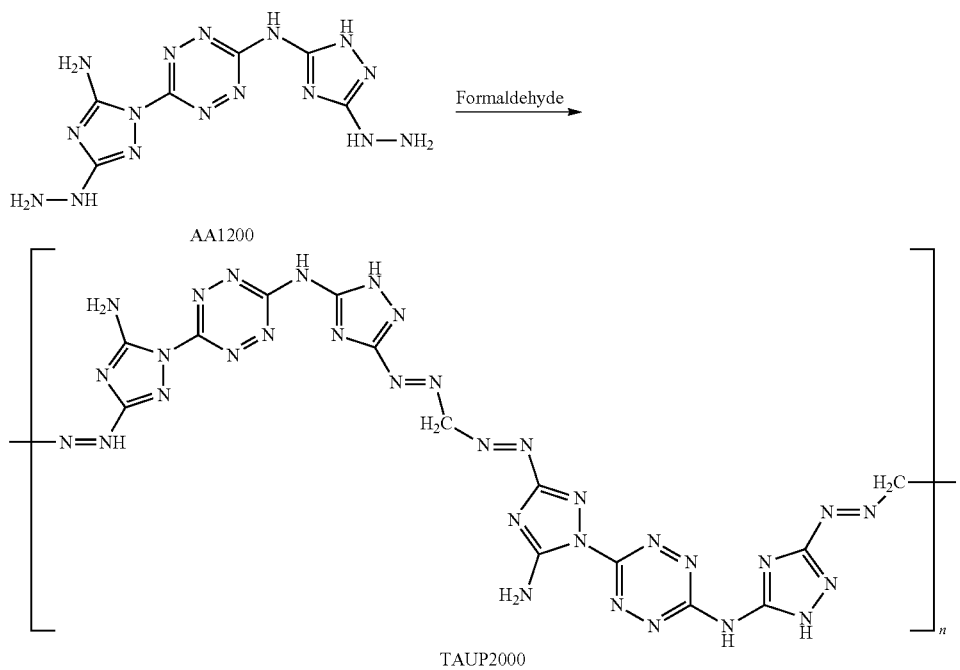

Example 4

Glyoxal-Based Coupling Polymerization

The following presents an exemplary synthesis of an exemplary class of energetic polymers, based on a coupling polymerization reaction with glyoxal.

General Procedure:

The scheme below presents a general polymerization of glyoxal with bis-hydrazo monomers, wherein Z can be alkyl, aryl, heterocyclic, heteroaryl, substituted 1,2,4,5-tetrazine and the like.

Scheme 26

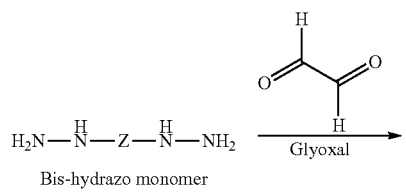

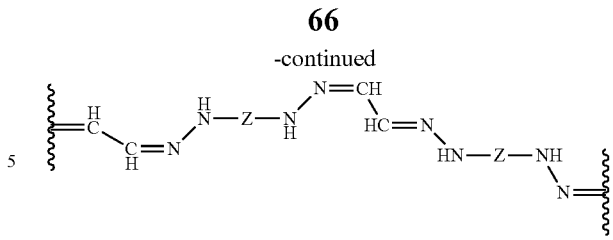

Synthesis of an Exemplary Polymer TAUP3000

The scheme below is proposed as a schematic synthetic procedure for the preparation of an exemplary energetic N-(3-(2-(((E)-allylidene)hydrazinyl)-1H-1,2,4-triazol-5-yl)-6-(5-amino-3-(2-((1E,2E)-2-(2-(5-((6-(5-amino-3-(2-methylenehydrazinyl)-1H-1,2,4-triazol-1-yl)-1,2,4,5-tetrazin-3-yl)amino)-1H-1,2,4-triazol-3-yl)hydrazono)-ethylidene) hydrazinyl)-1H-1,2,4-triazol-1-yl)-1,2,4,5-tetrazin-3-amine ("TAUP3000") polymer from the exemplary 6-(5-amino-3-hydrazinyl-1H-1,2,4-triazol-1-yl)-N-(3-hydrazinyl-1H-1,2,4-triazol-5-yl)-1,2,4,5-tetrazin-3-amine ("AA1200") monomer and glyoxal.

Scheme 27

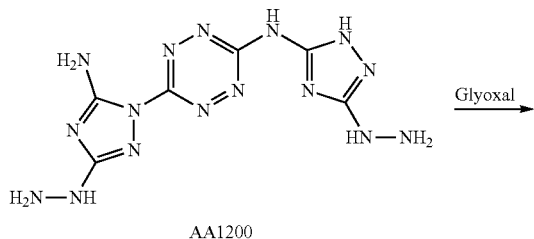

AA1200

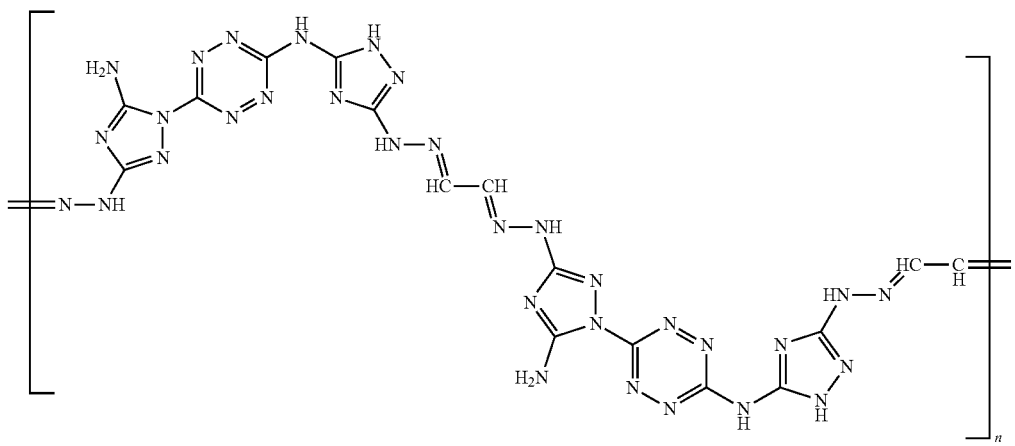

TAUP3000

The procedure may follow reactions such as presented, for example, in U.S. Pat. No. 3,375,230.

The procedure may follow reactions such as presented, for example, in U.S. Pat. No. 3,375,230.

Synthesis of Polymer AS-196

Scheme 28

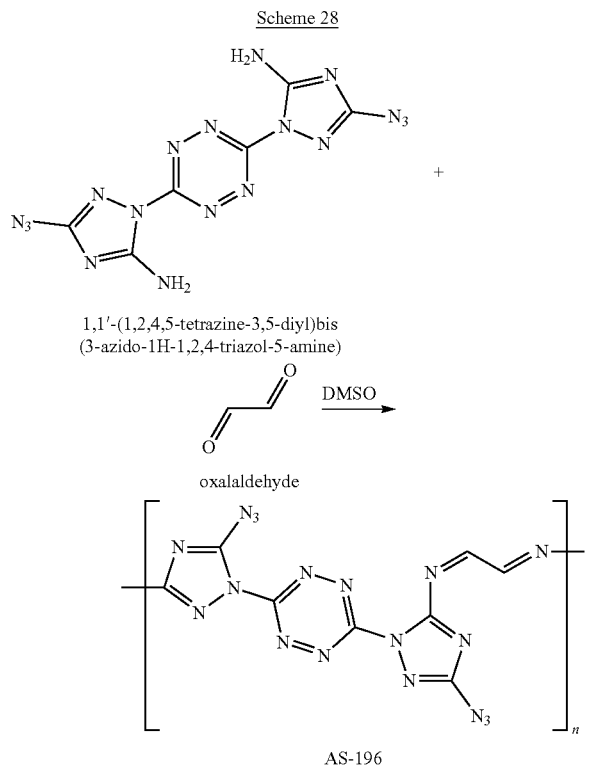

AS-196

To a solution of 1,2,4,5-tetrazine-3,6-diyl-bis(3-azido-1H-1,2,4-triazol-5-amine) (102 mg, 0.3 mmol) in DMSO (3 mL) a solution of glyoxal (65 µl, 40% w/w in water) was added and the reaction mixture was heated at 100° C. for 20 hr. Then, the reaction mixture was cooled to room temperature, stirred for additional 6 hr and ethyl acetate (30 mL) was added. Formed precipitate was collected by filtration, washed with diethylether (40 ml) and vacuum-dried to yield polymer AS-196.

Synthesis of Polymer AZ-159

Scheme 29

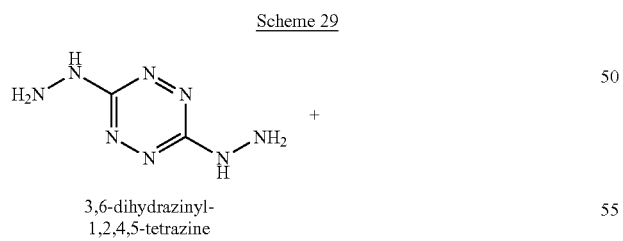

3,6-dihydrazinyl-1,2,4,5-tetrazine

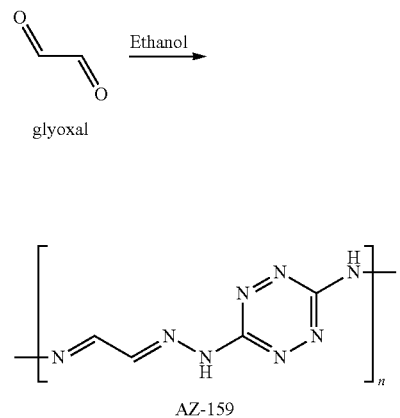

AZ-159

To a solution of 3,6-dihydrazinyl-1,2,4,5-tetrazine (142 mg, 2.0 mmol) in ethanol (10 ml) glyoxal solution (113 al, 40% w/w in water) was added and the reaction mixture was refluxed for 16 hours. Thereafter, the reaction mixture was cooled to room temperature and the formed precipitate was collected by filtration, washed with acetone and vacuum dried to yield a brown-colored AZ-159 (141 mg, 86%). FTIR (ATR): 3024 (w), 3208 (w), 1668 (w), 1632 (w), 1565 (w), 1529 (s), 1479 (s), 1416 (m), 1368 (m), 1338 (s), 1295 (w), 1282 (w), 1114 (m), 1037 (s) 939 (w), 864 (w), 822 (w), 784, 644 (w), 548 (w), 487 (w). $T_{decomp}$. (DSC) 160.1° C.

Example 5

Isocyanate-Based and Polyurethane-Based Polymerization

The following presents the exemplary synthesis and analysis of an exemplary class of energetic polymers, based on a coupling a bis-isocyanate monomer with bis-hydrazo monomer.

General Procedure:

The scheme below presents a general polymerization of a bis-isocyanate monomer with a bis-hydrazo monomer, wherein Y and Z can each be independently alkyl, aryl, heterocyclic, heteroaryl, substituted 1,2,4,5-tetrazine and the like.

Scheme 30

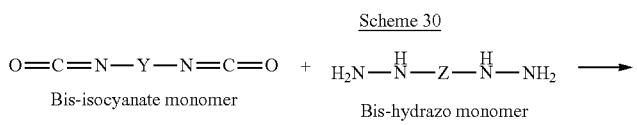

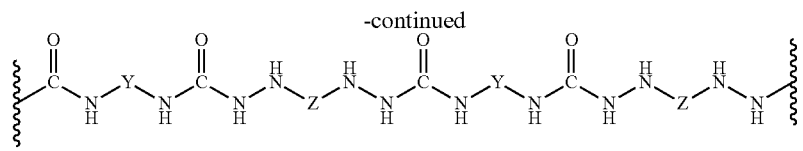

Synthesis of an Exemplary Polymer TAUP5000

The scheme below is proposed as a schematic synthetic coupling procedure for the preparation of an exemplary energetic polymer N-(5-acetamidopentyl)-2-(5-((6-(5-amino-3-(2-methyl-hydrazinyl)-1H-1,2,4-triazol-1-yl)-1,2,4,5-tetrazin-3-yl)amino)-1H-1,2,4-triazol-3-yl)-hydrazine-1-carboxamide ("TAUP5000") from the exemplary 6-(5-amino-3-hydrazinyl-1H-1,2,4-triazol-1-yl)-N-(3-hydrazinyl-1H-1,2,4-triazol-5-yl)-1,2,4,5-tetrazin-3-amine ("AA1200") monomer and 1,6-diisocyanatohexane.

Scheme 31

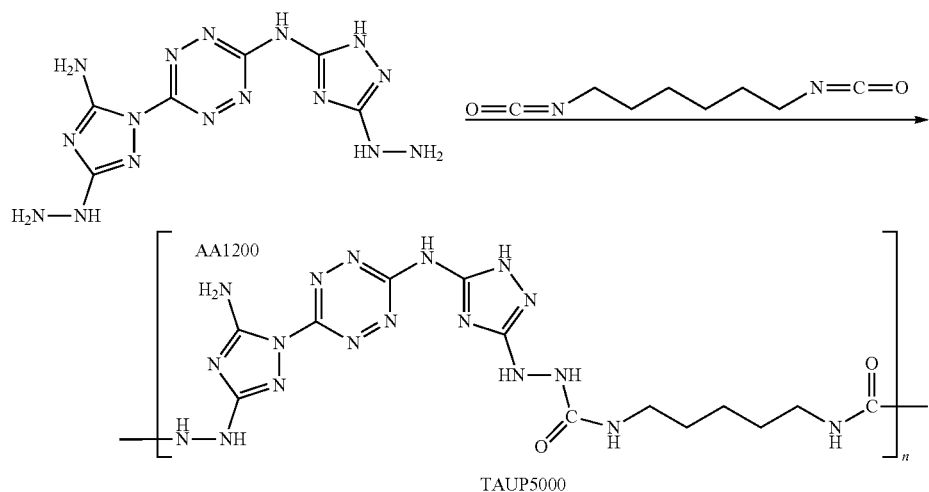

A mixture of 6-(5-amino-3-hydrazinyl-1H-1,2,4-triazol-1-yl)-N-(3-hydrazinyl-1H-1,2,4-triazol-5-yl)-1,2,4,5-tetrazin-3-amine ("AA1200") (5.0 mmol) and 1,6-diisocyanatohexane (5.2 mmol) in DFM (30 mL) is stirred for 2 days at room temperature. Thereafter, the formed precipitate is collected by filtration, washed with water and vacuum dried, to yield N-(5-acetamidopentyl)-2-(5-((6-(5-amino-3-(2-methyl-hydrazinyl)-1H-1,2,4-triazol-1-yl)-1,2,4,5-tetrazin-3-yl)amino)-1H-1,2,4-triazol-3-yl)-hydrazine-1-carboxamide ("TAUP5000") polymer.

Synthesis of an Exemplary Polymer TAUP5002

The scheme below is proposed as a schematic synthetic coupling procedure for the preparation of an exemplary energetic TAUP5002 polymer using from N',N'''-(1,2,4,5-tetrazine-3,6-diyl)di(methane-bis(imidhydrazide)) ("AA1202") monomer and 1,6-diisocyanatohexane.

Scheme 32

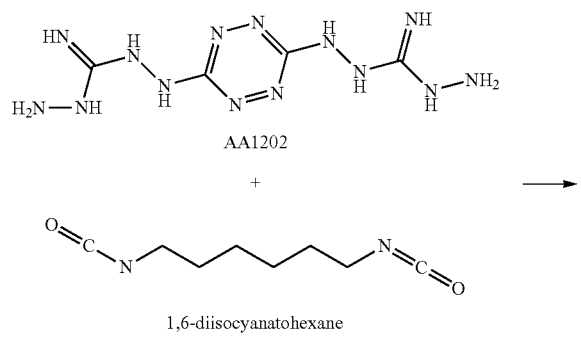

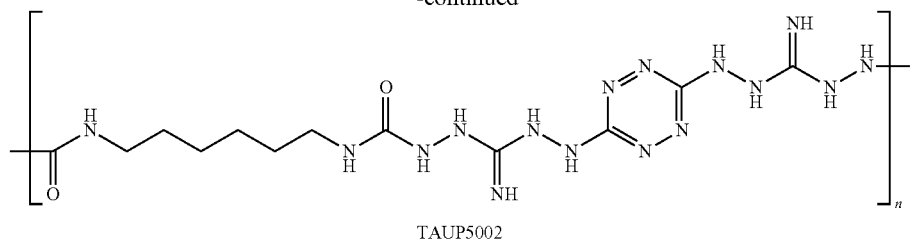

TAUP5002

A mixture of N',N'''-(1,2,4,5-tetrazine-3,6-diyl)di(methane-bis(imid-hydrazide)) ("AA1202") (5.0 mmol) and 1,6-diisocyanatohexane (5.2 mmol) in DFM (30 mL) is stirred for 2 days at room temperature. Thereafter, the formed precipitate is collected by filtration, washed with water and vacuum dried to yield TAUP5002 polymer.

Synthesis of an Exemplary Cyclic Polymer TAUMC5003

The scheme below presents a schematic synthetic coupling procedure for the preparation of a "TAUMC5003", which is an exemplary energetic cyclic "2+2" tetramer, comprising two 3,6-dihydrazinyl-1,2,4,5-tetrazine monomers and two 1,4-diisocyanatobutane monomers, each acting as a coupling agent.

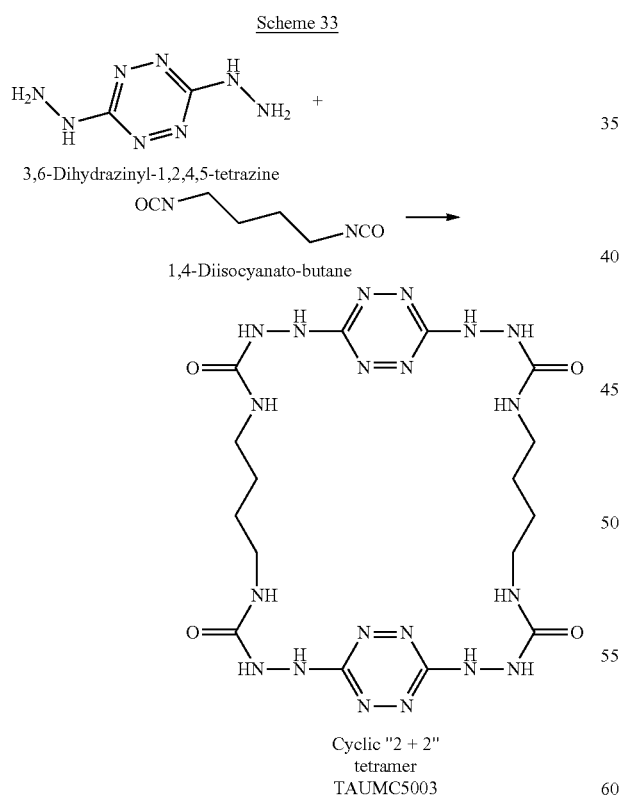

Scheme 33

3,6-Dihydrazinyl-1,2,4,5-tetrazine 1,4-Diisocyanato-butane

Cyclic "2 + 2" tetramer
TAUMC5003

To a solution of 3,6-dihydrazinyl-1,2,4,5-tetrazine (145 mg, 0.1 mmol) in DMF (30 ml) 1,4-diisocyanatobutane (145 mg, 0.1 mmol) was added and the resulted solution was stirred at room temperature for overnight. The formed precipitate was filtered, washed with THF (3×20 ml), water (3×50 ml) and vacuum dried. A crude solid material was re-dissolved in DMF (10 ml) at 90° C. and water (3 ml) was added dropwise. Upon cooling to room temperature TAUMC5003 precipitated, filtered, washed with THF (3×20 ml) and vacuum dried. Yield: 42%. $T_{decomp.}$ (DSC) 230.4° C. FTIR (ATR, cm$^{-1}$): 3271 (w), 2351 (s), 2321 (s), 1625 (m), 1566 (m), 1439 (m), 1244 (m), 1037 (s), 959 (m), 567 (m). $^1$H NMR (400 MHz, DMSO-d$_6$) δ: 1.30 (bs, 8H, CH$_2$), 2.87 (bs, 8H, CH$_2$), 6.55 (bs, 4H, NH), 7.93 (s, 4H, NH), 9.20 (s, 4H, NH). $^{13}$C NMR (100 MHz, DMSO-d$_6$) δ: 26.2 (CH$_2$), 37.9 (CH$_2$), 151.6 (C=O), 161.9 (C=N). $^{13}$C DEPT135 (100 MHz, DMSO-d$_6$) δ: 26.2 (CH$_2$), 37.9 (CH$_2$). HRMS (ESI$^-$): m/z=587.2502 [M–H$^-$]. Bomb calorimetry: gross heat of 3,382 cal/g.

FIGS. 1A-1B present an electrospray mass spectrogram (FIG. 1A) and a differential scanning calorimetric measurement (FIG. 1B) of TAUMC5003.

As can be seen in FIG. 1A, the mass spectrogram peak at 587.2 Da clearly indicates that the target cyclic "2+2" tetramer was formed as the major product. The peaks at 869.4 Da and 1151.5 Da are assigned to small amounts of the cyclic "3+3" hexamer and the cyclic "4+4" octamer respectively, were formed in trace amounts. As can be seen in FIG. 1B, evaluation of thermal properties of TAUMC5003 showed that this compound is energetic.

Synthesis of an Exemplary Cyclic Polymer TAUMC5004

The scheme below presents a schematic synthetic coupling procedure for the preparation of a "TAUMC5004", which is an exemplary energetic cyclic "2+2" tetramer, comprising two 3,6-dihydrazinyl-1,2,4,5-tetrazine monomers and two 1,6-diisocyanatohexane monomers, each acting as a coupling agent.

Scheme 34

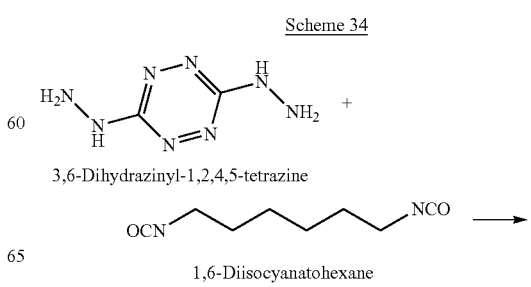

3,6-Dihydrazinyl-1,2,4,5-tetrazine 1,6-Diisocyanatohexane

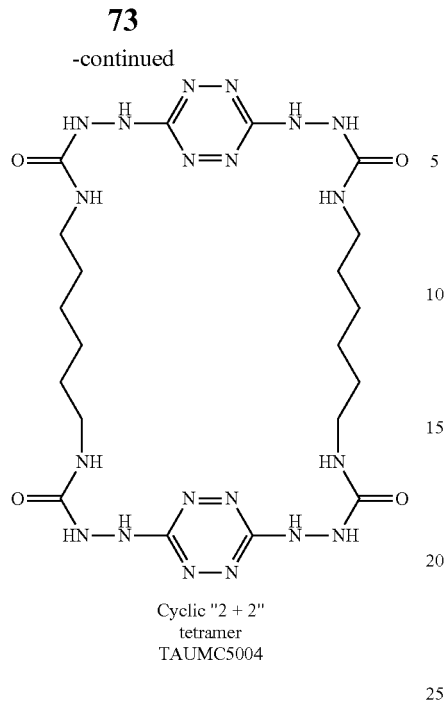

Cyclic "2 + 2" tetramer
TAUMC5004

To a solution of 3,6-dihydrazinyl-1,2,4,5-tetrazine (145 mg, 0.1 mmol) in a mixture of DMF/THF (30 ml, 1:1 v/v) 1,6-diisocyanatohexane (168 mg, 0.1 mmol) was added and the resulted solution was stirred at room temperature for overnight. The formed precipitate was filtered, washed with THF (3×20 ml), water (3×50 ml) and vacuum dried. A crude solid material was re-dissolved in DMF (20 ml) at 100° C. and water (5 ml) was added dropwise. Upon cooling to room temperature TAUMC5004 precipitated. It was filtered out, washed with THF (3×20 ml) and vacuum dried. Yield: 51%. $T_{decomp}$. (DSC) 227° C. FTIR (ATR, cm$^{-1}$): 3264 (w), 2929 (m), 2346 (m), 1648 (m), 1533 (m), 1437 (m), 1256 (s), 1055 (m), 950 (m), 568 (s). 1H NMR (400 MHz, DMSO-d6) δ: 0.33 (s, 8H, CH$_2$), 0.48 (s, 8H, CH$_2$), 2.10 (s, 8H, CH$_2$), 5.68 (bs, 4H, NH), 7.05 (s, 4H, NH), 8.31 (s, 4H, NH); 13C NMR (100 MHz, DMSO-d6) δ: 26.5 (CH$_2$), 30.3 (CH$_2$), 39.6 (CH$_2$), 159.0 (C=O), 163.4 (C=N). HRMS (ESI-): m/z=619.3146 [M-H]$^-$.

Synthesis of an Exemplary Cyclic Polymer TAUMC5005

The scheme below presents a schematic synthetic coupling procedure for the preparation of a "TAUMC5005", which is an exemplary energetic cyclic "2+2" tetramer, comprising two 3,6-dihydrazinyl-1,2,4,5-tetrazine monomers and two toluene-2,4-diisocyanate monomers, each acting as a coupling agent.

Scheme 35

3,6-Dihydrazinyl-1,2,4,5-tetrazine

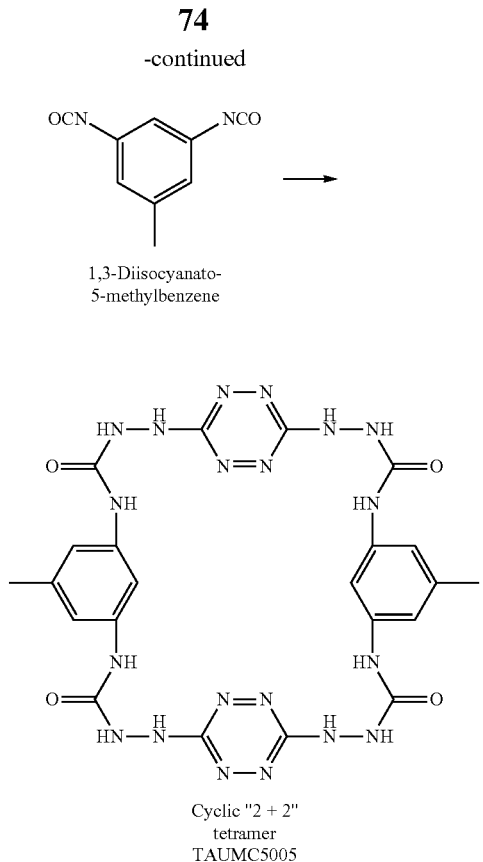

1,3-Diisocyanato-5-methylbenzene

Cyclic "2 + 2" tetramer
TAUMC5005

To a solution of 3,6-dihydrazinyl-1,2,4,5-tetrazine (145 mg, 0.1 mmol) in a mixture of DMF/THF (30 ml, 1:1 v/v) toluene-2,4-diisocyanate (175 mg, 0.1 mmol) was added and the resulted solution was stirred at room temperature for overnight. The formed precipitate was filtered, washed with THF (3×20 ml), water (3×50 ml) and vacuum dried. A crude solid material was re-dissolved in DMF (20 ml) at 60° C. and water (20 ml) was added dropwise. Upon slow cooling to room temperature TAUMC5005 precipitated, filtered, washed with THF (3×20 ml) and vacuum dried. Yield: 57%. $T_{decomp}$. (DSC) 234.2° C. FTIR (ATR, cm-1): 3738 (m), 3630 (m), 3178 (w), 2521 (w), 2171 (m), 2009 (m), 1538 (m), 1045 (m), 640 (s). (400 MHz, DMSO-d6) δ: 2.10 (s, 6H, CH$_3$), 7.04 (s, 4H, NH), 7.66-8.82 (m, 10H, 4 NH+6 aromatics), 9.43 (s, 4H, NH). $^{13}$C NMR (100 MHz, DMSO-d6) δ: 17.2 (CH$_3$), 110.3 (CH, aromatic), 126.1 (CH, aromatic), 129.6 (C—NH, aromatic), 137.8 (C—CH$_3$, aromatic), 155.8 (C=O), 162.0 (N—C—N tetrazine). HRMS (ESI-): m/z=631.2205 [M-H]$^-$.

Synthesis of an Exemplary Non-Cyclic Polymer TAUP5003

The scheme below presents a schematic synthetic coupling procedure for the preparation of a "TAUMC5003", which is an exemplary energetic polymer, comprising of 3,6-dihydrazinyl-1,2,4,5-tetrazine monomers and 1,4-biisocyanatobutane, each acting as a coupling agent.

Scheme 36

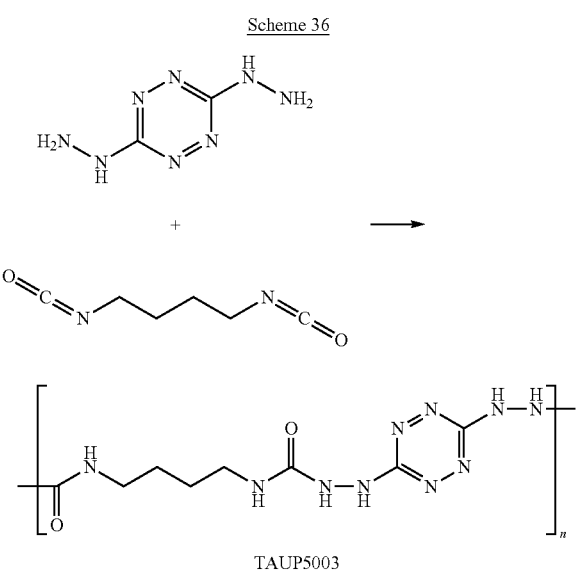

TAUP5003

To a dispersion of 3,6-dihydrazinyl-1,2,4,5-tetrazine (145 mg, 0.1 mmol) in DMF (1 ml) 1,4-diisocyanatobutane (145 mg, 0.1 mmol) was added and the resulted solution was stirred at room temperature for overnight. The formed rubber-like red-orange solid was filtered, washed with DMF (3×20 ml), water (5×100 ml) and extensively vacuum dried to give TAUP5003 polymer. $T_{decomp}$. (DSC) 226.4° C. FTIR (ATR, cm-1): 3226 (m), 2931.0 (m), 2340.1 (m), 1647.66 (s), 1533.0 (s), 1448.5 (s), 1261.5 (m), 1044.4 (m), 943.0 (s) 544.7 (s).

Synthesis of an Exemplary Non-Cyclic Polymer TAUP5004

The scheme below presents a schematic synthetic coupling procedure for the preparation of a "TAUMC5004", which is an exemplary energetic polymer, comprising of 3,6-dihydrazinyl-1,2,4,5-tetrazine monomers and 1,6-diisocyanatohexane, each acting as a coupling agent.

Scheme 37

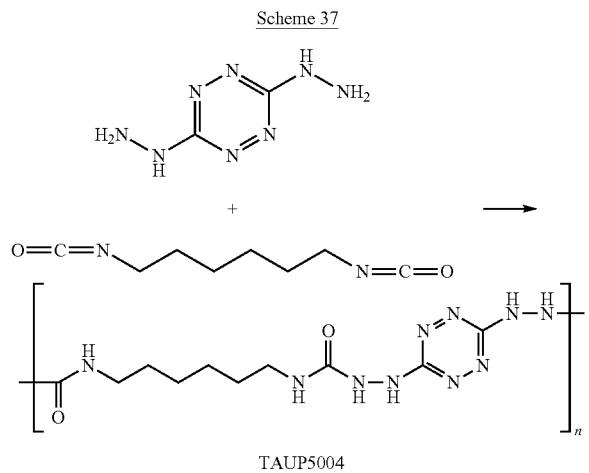

TAUP5004

To a dispersion of 3,6-dihydrazinyl-1,2,4,5-tetrazine (145 mg, 0.1 mmol) in DMF (1 ml) 1,6-diisocyanatohexane (168 mg, 0.1 mmol) was added and the resulted solution was stirred at room temperature for overnight. Formed rubber-like red-orange solid was filtered, washed with DMF (3×20 ml), water (5×100 ml) and extensively vacuum dried to give TAUP5004 polymer. $T_{decomp}$. 218.1° C. FTIR (ATR, cm-1): 3708 (m), 3243 (w), 2937 (m), 1647 (s), 1551 (s), 1413 (m), 1262 (m), 1051 (m), 943 (s), 479 (w).

Synthesis of an Exemplary Non-Cyclic Polymer TAUP5005

The scheme below presents a schematic synthetic coupling procedure for the preparation of a "TAUMC5005", which is an exemplary energetic polymer, comprising of 3,6-dihydrazinyl-1,2,4,5-tetrazine monomers and toluene-2,4-diisocyanate, each acting as a coupling agent.

Scheme 38

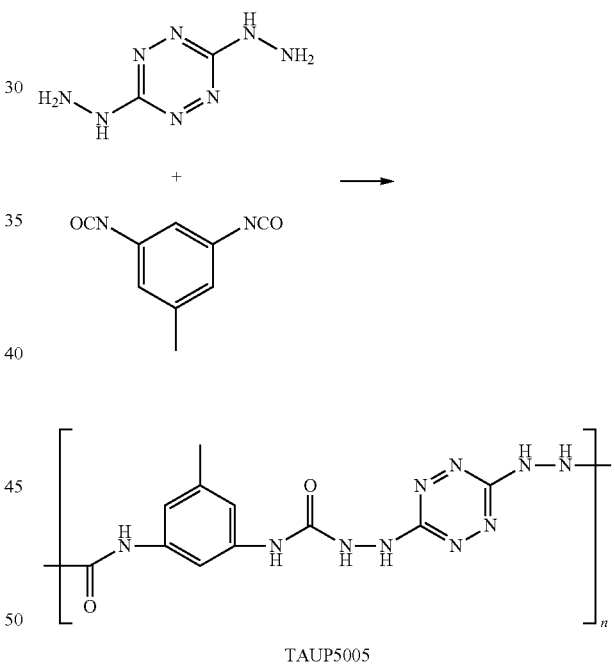

TAUP5005

To a dispersion of 3,6-dihydrazinyl-1,2,4,5-tetrazine (145 mg, 0.1 mmol) in DMF (1 ml) toluene-2,4-diisocyanate (175 mg, 0.1 mmol) was added and the resulted solution was stirred at room temperature for overnight. The formed rubber-like red-orange solid was filtered, washed with DMF (3×20 ml), water (5×100 ml) and extensively vacuum dried to give TAUP5005 polymer. $T_{decomp}$. (DSC) 206.8° C. FTIR (ATR, cm−1): 3220 (w), 2340 (m), 1659 (s), 1520 (s), 1442 (s), 1316 (m), 1238 (s), 1039 (m), 949 (s), 666 (w), 551 (s), 485 (m).

Synthesis of an Exemplary Non-Cyclic Polymer
AS-199

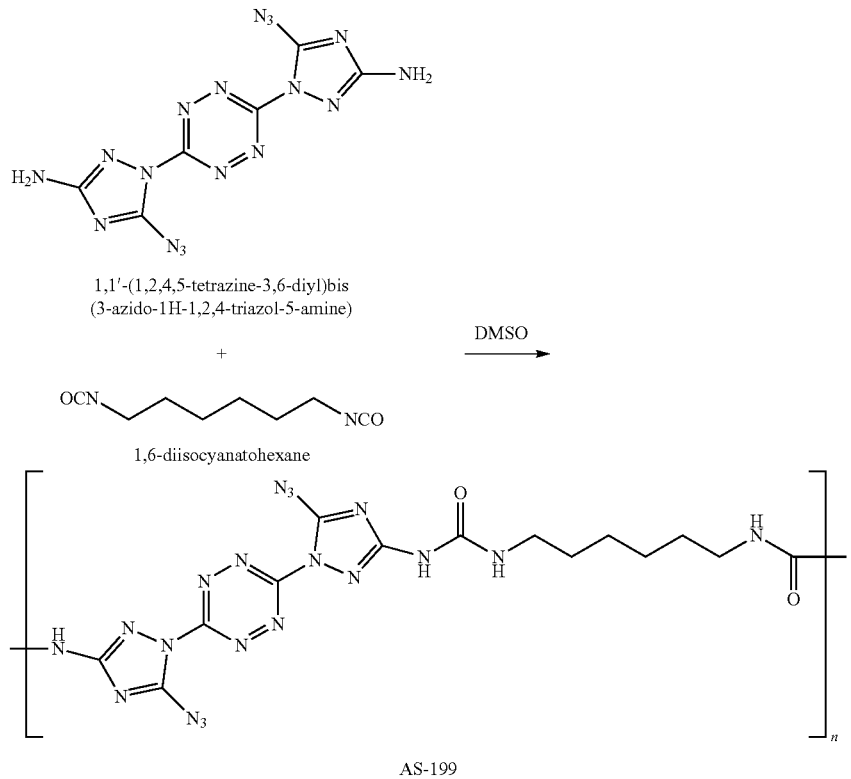

Scheme 39

1,1'-(1,2,4,5-tetrazine-3,6-diyl)bis
(3-azido-1H-1,2,4-triazol-5-amine)

1,6-diisocyanatohexane

AS-199

To a solution of 1,2,4,5-tetrazine-3,6-diyl-bis(3-azido-1H-1,2,4-triazol-5-amine) (250 mg, 0.76 mmol) in DMSO (5 mL) a solution of 1,6-diisocyano-hexane (160 al, 1 mmol) was added and the reaction mixture was stirred at 65° C. for 7 days. After that time, the reaction mixture was cooled to room temperature and formed precipitate was collected by filtration, washed with diethylether and vacuum dried to yield polymer AS-199 as a red solid (284 mg). FTIR (ATR): 3317 (m), 2932 (m), 2856 (m), 2139 (m), 1706 (s), 1570 (s), 1476 (m), 1459 (m), 1459 (m), 1437 (m), 1375 (w), 1337 (w), 1251 (m), 1213 (w), 1076 (s), 733 (w), 612 (s).

Example 6

Imidamide-Based Polymerization

The following presents an exemplary synthesis of an exemplary class of energetic polymers, based on polymerization of bis-imidate monomers with bis-hydrazo monomers.

General Procedure:

The scheme below presents a general polymerization of a bis-imidate monomer with a bis-hydrazo monomer, wherein Y and Z can each be independently alkyl, aryl, heterocyclic, heteroaryl, substituted 1,2,4,5-tetrazine and the like.

Scheme 40

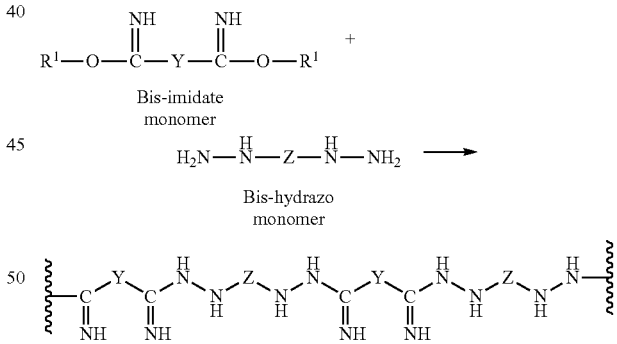

Synthesis of an Exemplary Polymer TAUP6000

The scheme below is proposed as a schematic synthetic procedure for the preparation of an exemplary energetic N'1-(5-amino-1-(6-((3-(2-(1,6-diiminoheptyl)hydrazinyl)-1H-1,2,4-triazol-5-yl)amino)-1,2,4,5-tetrazin-3-yl)-1H-1,2,4-triazol-3-yl)-N'6-(5-((6-(5-amino-3-(2-methylhydrazinyl)-1H-1,2,4-triazol-1-yl)-1,2,4,5-tetrazin-3-yl)amino)-1H-1,2,4-triazol-3-yl)adipimidohydrazide ("TAUP6000") polymer from the exemplary 6-(5-amino-3-hydrazinyl-H-1,2,4-triazol-1-yl)-N-(3-hydrazinyl-1H-1,2,4-triazol-5-yl)-1,2,4,5-tetrazin-3-amine ("AA1200") monomer and dimethyl adipimidate.

Scheme 41

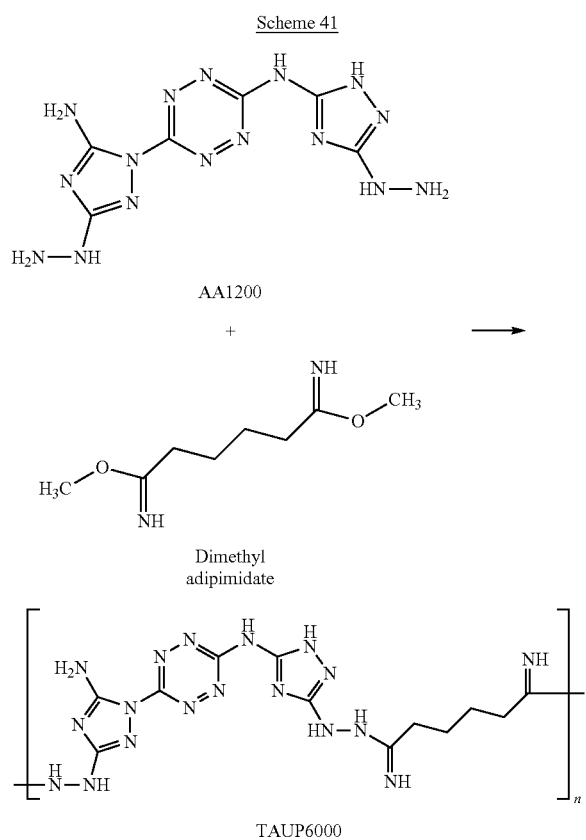

AA1200

Dimethyl adipimidate

TAUP6000

A mixture of 6-(5-amino-3-hydrazinyl-1H-1,2,4-triazol-1-yl)-N-(3-hydrazinyl-1H-1,2,4-triazol-5-yl)-1,2,4,5-tetrazin-3-amine ("AA1200") (5.0 mmol) and dimethyl adipimidate (5.2 mmol) in DFM (30 mL) is stirred for 2 days at room temperature. Thereafter, the formed precipitate is collected by filtration, washed with water and vacuum dried, to yield N'1-(5-amino-1-(6-((3-(2-(1,6-diiminoheptyl)hydrazinyl)-1H-1,2,4-triazol-5-yl)amino)-1,2,4,5-tetrazin-3-yl)-1H-1,2,4-triazol-3-yl)-N'6-(5-((6-(5-amino-3-(2-methylhydrazinyl)-1H-1,2,4-triazol-1-yl)-1,2,4,5-tetrazin-3-yl)amino)-1H-1,2,4-triazol-3-yl)adipimidohydrazide ("TAUP6000") polymer.

Synthesis of an Exemplary Polymer TAUMC6002

The scheme below is proposed as a schematic synthetic procedure for the preparation of a cyclic 2,3,10,11,13,14,21,22-octaaza-1,12(3,6)-ditetrazinacyclodocosaphane-4,9,15,20-tetraimine ("TAUMC6002"), which is an exemplary energetic cyclic "2+2" tetramer, comprising two 3,6-dihydrazinyl-1,2,4,5-tetrazine monomers and two dimethyl adipimidate monomers.

Scheme 42

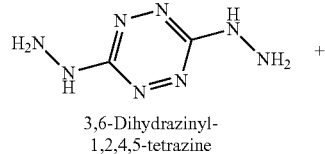

3,6-Dihydrazinyl-1,2,4,5-tetrazine

+

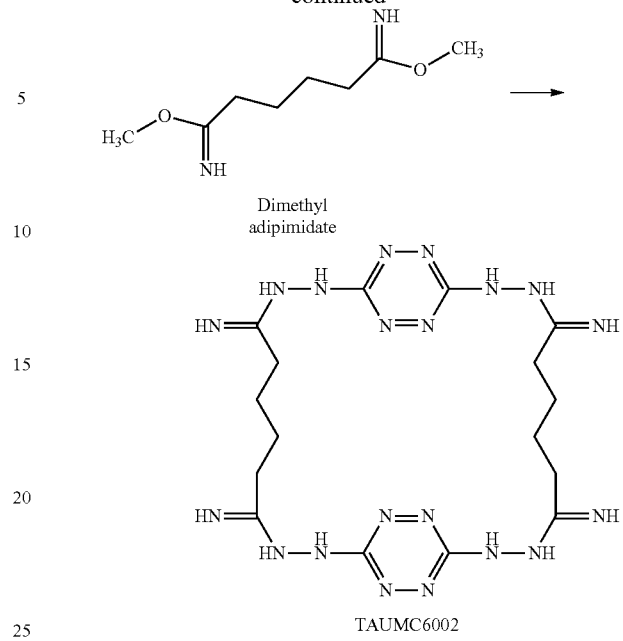

Dimethyl adipimidate

TAUMC6002

A mixture of 3,6-dihydrazinyl-1,2,4,5-tetrazine (726 mg, 5.14 mmol) and dimethyl adipimidate (5.17 mmol) in DFM (30 mL) is stirred for 2 days at room temperature. Thereafter, the formed precipitate is collected by filtration, washed with water and vacuum dried, yielding cyclic 2,3,10,11,13,14,21,22-octaaza-1,12(3,6)-ditetrazinacyclodocosaphane-4,9,15,20-tetraimine ("TAUMC6002") polymer.

Example 7

Polysiloxane-Based Polymerization

The following presents an exemplary synthesis of an exemplary class of energetic polymers, based on polymerization of bis-alkoxysilane monomers with diol monomers.

General Procedure.

The scheme below presents a general polymerization of a bis-alkoxysilane monomer with a diol monomer, wherein R1 and R2 can each be independently alkyl, aryl, heterocycle or heteroaryl, and Z can be alkyl, aryl, heterocyclic, heteroaryl, substituted 1,2,4,5-tetrazine and the like.

Scheme 43

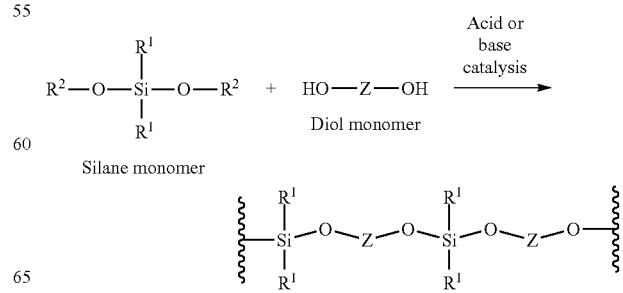

Synthesis of an Exemplary Polymer TAUP7000

The scheme below is proposed as a schematic synthetic procedure for the preparation of an exemplary energetic N-(3-azido-1-(2-(((2-((3-azido-1-(6-((3-azido-1-(2-methoxy-ethyl)-1H-1,2,4-triazol-5-yl)amino)-1,2,4,5-tetrazin-3-yl)-1H-1,2,4-triazol-5-yl)-amino)ethoxy)-dimethylsilyl)-oxy)ethyl)-1H-1,2,4-triazol-5-yl)-6-(3-azido-5-((2-((trimethylsilyl)-oxy)ethyl)amino)-1H-1,2,4-triazol-1-yl)-1,2,4,5-tetrazin-3-amine ("TAUP7000") polymer from 2-((3-azido-1-(6-((3-azido-1-(2-hydroxyethyl)-1H-1,2,4-triazol-5-yl)amino)-1,2,4,5-tetrazin-3-yl)-1H-1,2,4-triazol-5-yl)amino)ethan-1-ol ("AA1600") monomer and diethoxydimethylsilane.

and dried, yielding N-(3-azido-1-(2-(((2-((3-azido-1-(6-((3-azido-1-(2-methoxyethyl)-1H-1,2,4-triazol-5-yl)amino)-1,2,4,5-tetrazin-3-yl)-1H-1,2,4-triazol-5-yl)amino)ethoxy)-dimethylsilyl)-oxy)ethyl)-1H-1,2,4-triazol-5-yl)-6-(3-azido-5-((2-((trimethylsilyl)-oxy)ethyl)amino)-1H-1,2,4-triazol-1-yl)-1,2,4,5-tetrazin-3-amine ("TAUP7000").

Synthesis of an Exemplary Polymer TAUP7001

The scheme below is proposed as a schematic synthetic procedure for the preparation of an exemplary energetic N3-(5-((((dimethyl((3-((6-((5-((((trimethylsilyl)oxy)methyl)-1H-1,2,4-triazol-3-yl)amino)-1,2,4,5-tetrazin-3-yl)amino)-1H-1,2,4-triazol-5-yl)-methoxy) silyl)oxy)methyl)-1H-1,2,

Scheme 44

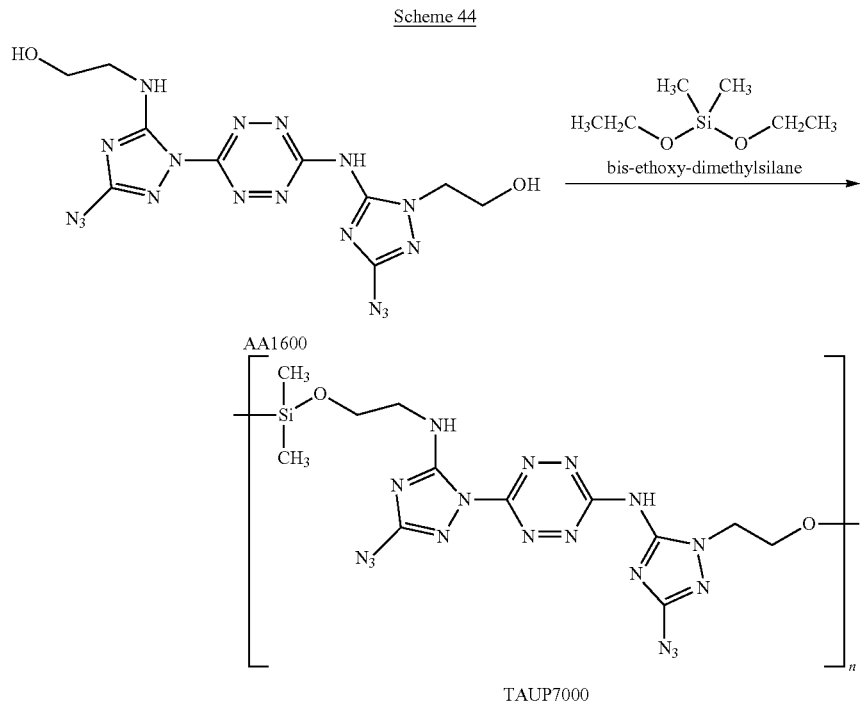

TAUP7000

To the suspension of 2-((3-azido-1-(6-((3-azido-1-(2-hydroxyethyl)-1H-1,2,4-triazol-5-yl)amino)-1,2,4,5-tetrazin-3-yl)-1H-1,2,4-triazol-5-yl)amino)ethan-1-ol ("AA1600") (0.345 mol) in methanol (1.0 L) diethoxydimethylsilane (0.726 mol) is added and the reaction mixture is stirred for 12 hours at room temperature. Formed precipitate is filtered 4-triazol-3-yl)-N6-(5-(methoxymethyl)-1H-1,2,4-triazol-3-yl)-1,2,4,5-tetrazine-3,6-diamine ("TAUP7001") polymer, from (5-((6-((3-(hydroxylmethyl)-1H-1,2,4-triazol-5-yl)amino)-1,2,4,5-tetrazin-3-yl)amino)-4H-1,2,4-triazol-3-yl)-methanol ("AA1700") monomer and diethoxydimethylsilane.

Scheme 45

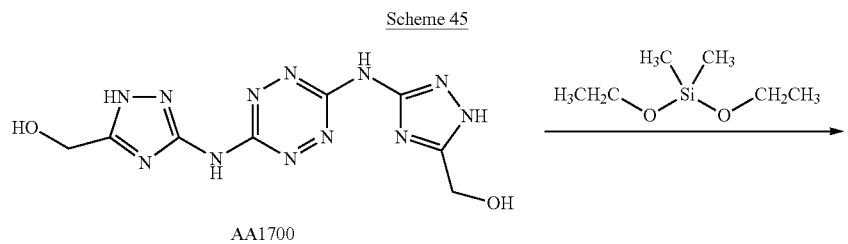

AA1700

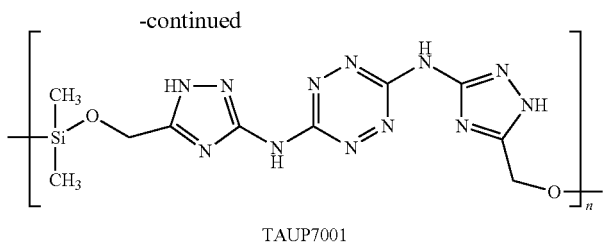

TAUP7001

To the suspension of (5-(((6-(((3-(hydroxylmethyl)-1H-1,2,4-triazol-5-yl)amino)-1,2,4,5-tetrazin-3-yl)amino)-4H-1,2,4-triazol-3-yl)-methanol ("AA1700") (0.345 mol) in methanol (1.0 L) diethoxydimethylsilane (0.726 mol) is added and the reaction mixture is stirred for 12 hours at room temperature. Formed precipitate is filtered and dried, yielding N3-(5-(((dimethyl((3-(((6-(((5-(((trimethylsilyl)oxy)-methyl)-1H-1,2,4-triazol-3-yl)amino)-1,2,4,5-tetrazin-3-yl)amino)-1H-1,2,4-triazol-5-yl)-methoxy)silyl)oxy)methyl)-1H-1,2,4-triazol-3-yl)-N6-(5-(methoxymethyl)-1H-1,2,4-triazol-3-yl)-1,2,4,5-tetrazine-3,6-diamine ("TAUP7001") polymer.

Example 8

Diazonium-Based Polymerization

The following presents exemplary syntheses of an exemplary class of diazonium-based energetic polymers.

It is noted herein that in the diazomium-based polymerization that goes via formation of a diazonium ion intermediate from the corresponding amine-containing monomer, the diazonium ion can be isolated in the form of a salt, albeit such intermediates tend to be highly sensitive (explosive) and require special safely steps and procedures for handling, such as keeping these intermediates in solution.

Synthesis of Polymer TP-121

To a solution of $N^5,N^{5'}$-(1,2,4,5-tetrazine-3,6-diyl)bis(1H-1,2,4-triazole-3,5-diamine) (275 mg, 1 mmol) in concentrated $H_2SO_4$ (2 mL, 98%) $H_2O$ (3 mL) was added dropwise and the mixture was stirred for 1 hour at 0° C. Then, to this mixture a solution of $NaNO_2$ (200 mg, 2.85 mmol) in water (0.5 ml) was added dropwise, while the reaction temperature was kept below 5° C. and the mixture was stirred for 1 hour. Thereafter, $H_2O$ (20 mL) was added to the reaction mixture and formed diazonium salt (highly sensitive compound) was collected by filtration. Subsequently, wet diazonium salt was added to a solution of piperazine (108 mg) in water (15 mL) at 0° C. and the reaction mixture was allowed to heat up to room temperature and was stirred for overnight. Thereafter, the formed precipitate was filtered out, washed with acetonitrile (3×20 mL) and vacuum dried to yield purple-brown colored polymer TP-121.

Scheme 46

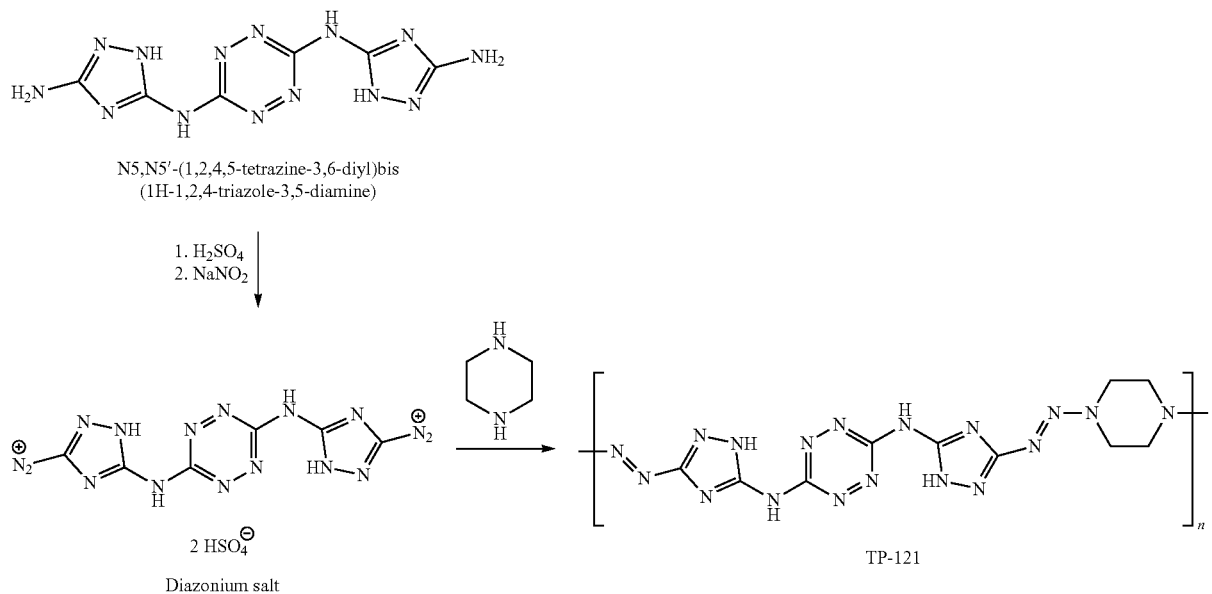

Synthesis of Polymer TP-113

Scheme 47

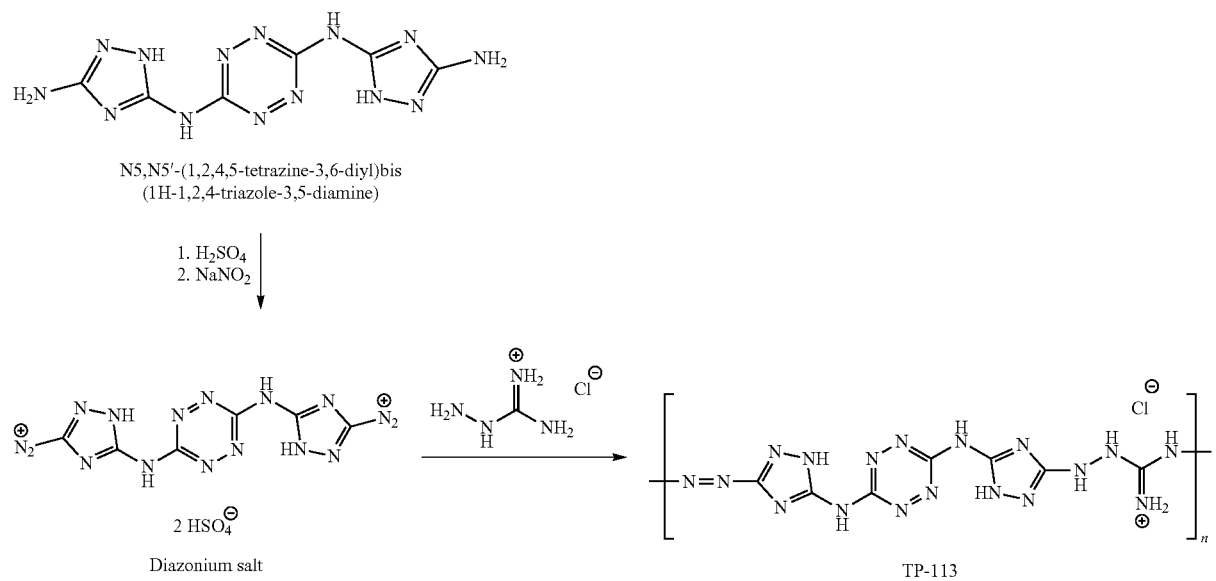

To a solution of N⁵,N⁵'-(1,2,4,5-tetrazine-3,6-diyl)bis(1H-1,2,4-triazole-3,5-diamine) (275 mg, 1 mmol) in concentrated H₂SO₄ (2 mL, 98%) H₂O (3 mL) was added dropwise and the mixture was stirred for 1 hour at 0° C. Thereafter, a solution of NaNO₂ (200 mg, 2.85 mmol) in water (0.5 ml) was added dropwise to the reaction mixture, while maintaining the mixture below 5° C. and stirred for 1 hour. Thereafter, H₂O (20 mL) was added to the reaction mixture and formed diazonium salt (highly sensitive compound) was collected by filtration. Subsequently, wet diazonium salt was added to a solution of aminoguanidine hydrochloride (137 mg, 1.24 mmol) in water (20 mL) at room temperature and the reaction mixture was stirred for overnight. Thereafter, the formed precipitate was filtered out, washed with acetonitrile (3×20 mL) and vacuum dried to yield polymer TP-113.

Synthesis of Polymer TP-116

Scheme 48

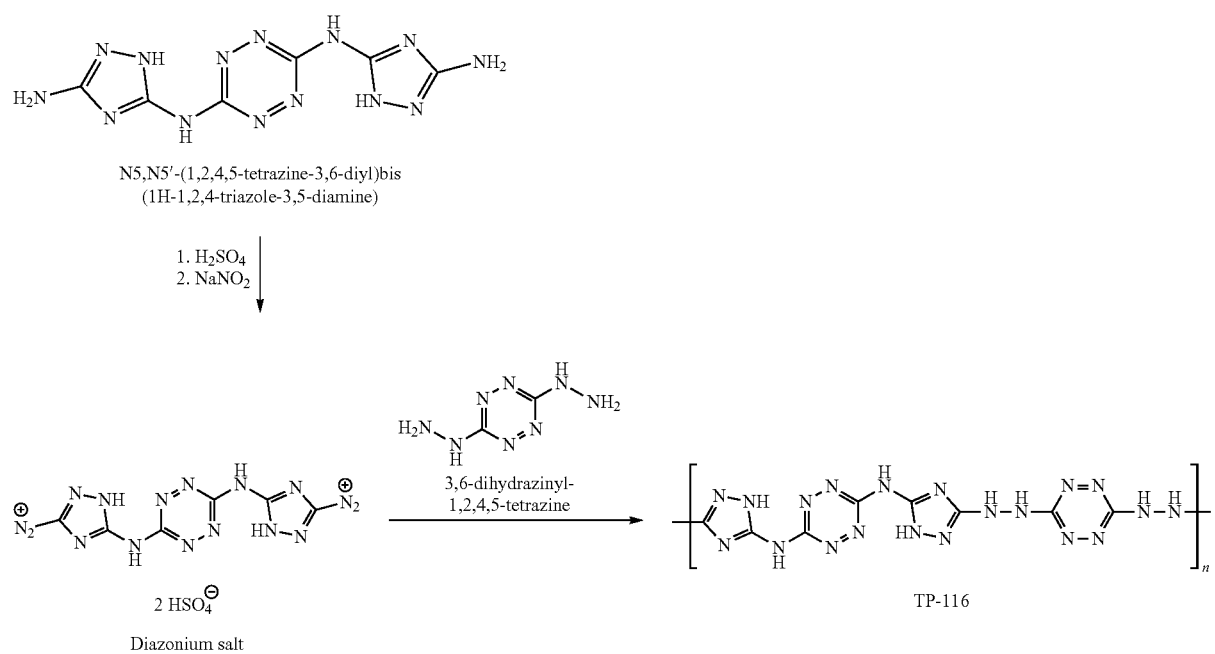

To a solution of $N^5,N^{5'}$-(1,2,4,5-tetrazine-3,6-diyl)bis(1H-1,2,4-triazole-3,5-diamine) (275 mg, 1 mmol) in concentrated $H_2SO_4$ (2 mL, 98%) $H_2O$ (3 mL) was added dropwise and the mixture was stirred for 1 hour at 0° C. Thereafter, to this mixture a solution of $NaNO_2$ (200 mg, 2.85 mmol) in water (0.5 ml) was added dropwise, while the reaction temperature was kept below 5° C. and the mixture was stirred for 1 hour. Thereafter, $H_2O$ (20 mL) was added to the reaction mixture and the formed diazonium salt (highly sensitive compound) was collected by filtration. Subsequently, wet diazonium salt was added dropwise to a solution of 3,6-dihydrazinyl-1,2,4,5-tetrazine (160 mg, 1.13 mmol) in water (20 mL) at 0° C. and stirred at this temperature for 2 hours. Thereafter, the reaction mixture was allowed to warm up to room temperature and was stirred for 30 minutes. Thereafter, the formed precipitate was filtered out, washed with acetonitrile (3×20 mL) and vacuum dried to yield purple-colored polymer TP-116.

Synthesis of Polymer TP-138

To a solution of $N^5,N^{5'}$-(1,2,4,5-tetrazine-3,6-diyl)bis(1H-1,2,4-triazole-3,5-diamine) (275 mg, 1 mmol) in concentrated $H_2SO_4$ (2 mL, 98%) $H_2O$ (3 mL) was added dropwise and the mixture was stirred for 1 hour at 0° C. Thereafter, to this mixture a solution of $NaNO_2$ (200 mg, 2.85 mmol) in water (0.5 ml) was added dropwise, while the reaction temperature was kept below 5° C. and the mixture was stirred for 1 hour. Thereafter, $H_2O$ (20 mL) was added to the reaction mixture and formed diazonium salt (highly sensitive compound) was collected by filtration. Subsequently, wet diazonium salt was added dropwise to a solution of 1,3-diaminoguanidine hydrochloride (134 mg, 1.06 mmol) in water (15 mL) at 0° C. and stirred at this temperature for 2 hours. Thereafter, the reaction mixture was allowed to warm up to room temperature and was stirred for 2 hours. Thereafter, the formed precipitate was filtered out, washed with acetonitrile (3×20 mL) and vacuum dried to yield purple-colored polymer TP-138.

Scheme 49

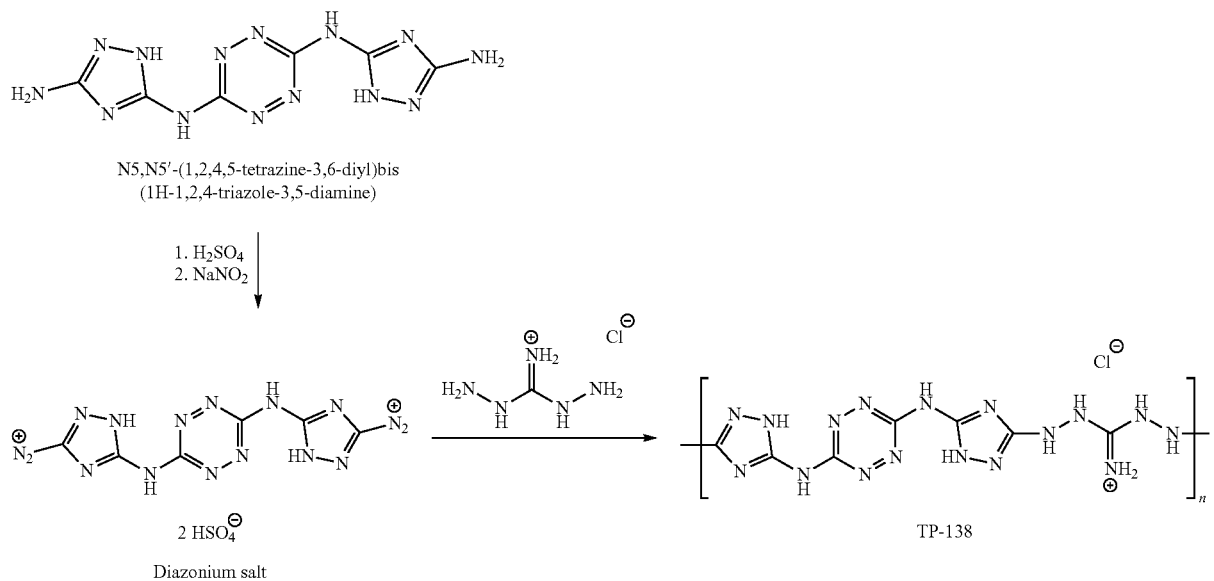

Synthesis of Polymer TP-143

Scheme 50

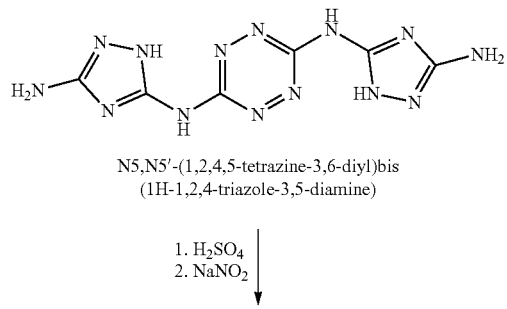

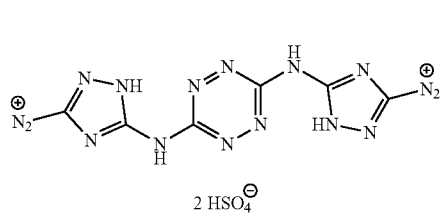

2 HSO$_4^\ominus$

Diazonium salt

-continued

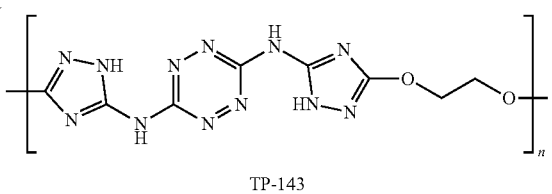

TP-143

To a solution of N$^5$,N$^{5'}$-(1,2,4,5-tetrazine-3,6-diyl)bis(1H-1,2,4-triazole-3,5-diamine) (275 mg, 1 mmol) in concentrated H$_2$SO$_4$ (2 mL, 98%) H$_2$O (3 mL) was added dropwise and the mixture was stirred for 1 hour at 0° C. Thereafter, to this mixture a solution of NaNO$_2$ (200 mg, 2.85 mmol) in water (0.5 ml) was added dropwise, while the reaction temperature was kept below 5° C. and the mixture was stirred for 1 hour. Thereafter, H$_2$O (20 mL) was added to the reaction mixture and formed diazonium salt (highly sensitive compound) was collected by filtration. Subsequently, wet diazonium salt was added dropwise to a solution of ethylene glycol (67 µl, 1.1 mmol) in water (15 mL) at 0° C. and stirred at this temperature for 2 hours. Thereafter, the reaction mixture was allowed to warm to room temperature and was stirred for 2 days. Thereafter, the formed precipitate was filtered out, washed with acetonitrile (3×20 mL) and vacuum dried to yield purple-colored polymer TP-143.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A mixture of monomers, each independently represented by the Formula I:

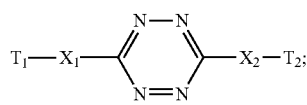

Formula I wherein:
each of X$_1$ and X$_2$ is independently NR or a covalent bond, and at least one of said X$_1$ and X$_2$ is NR,
R is H or C$_{1-4}$ alkyl,
each of T$_1$ and T$_2$ is independently a moiety selected from the group consisting of a triazole moiety, a tetrazole moiety and a guanidine moiety, at least one of said T$_1$ and T$_2$ being substituted by at least one polymerizable group, at least one of said T$_1$ and T$_2$ being said guanidine moiety or said tetrazole moiety, said polymerizable group being selected from the group consisting of azido, cyano, diazonium, ethynyl, hydrazine, hydroxyl, hydrazide, amine, ethanolamine, isocyanate, cyanate, amide, imidate, ester, carboxyl and azo, and a C1-4 alkyl terminated with azido, cyano, ethynyl, hydrazine, hydroxyl, hydrazide, amine, ethanolamine, isocyanate, cyanate, amide, imidate, ester, carboxyl and azo, and said monomers form a polymer via a reaction selected from metal-catalyzed click polymerization, poly-condensation and coupling.

2. The mixture of claim 1, wherein said guanidine moiety is represented by Formula II:

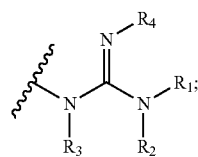

Formula II wherein each of R1, R2, R3 and R4 is independently H or said polymerizable group, provided that at least one of R1, R2, R3 and R4 is said polymerizable group.

3. The mixture of claim 2, wherein R1 is amino, each of R2, R3 and R4 is H and said guanidine moiety is 1-aminoguanidine.

4. The mixture of claim 1, wherein said triazole moiety is represented by a formula selected from the group consisting of Formula III, Formula IV and Formula V:

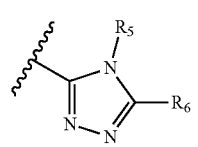

Formula III

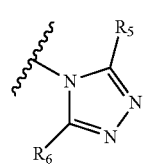

Formula IV

Formula V

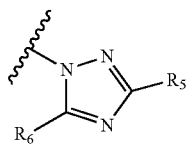

wherein each of R5 and R6 is independently H or said polymerizable group, provided that at least one of R5 and R6 is said polymerizable group.

5. The mixture of claim 4, wherein said triazole moiety is selected from the group consisting of:

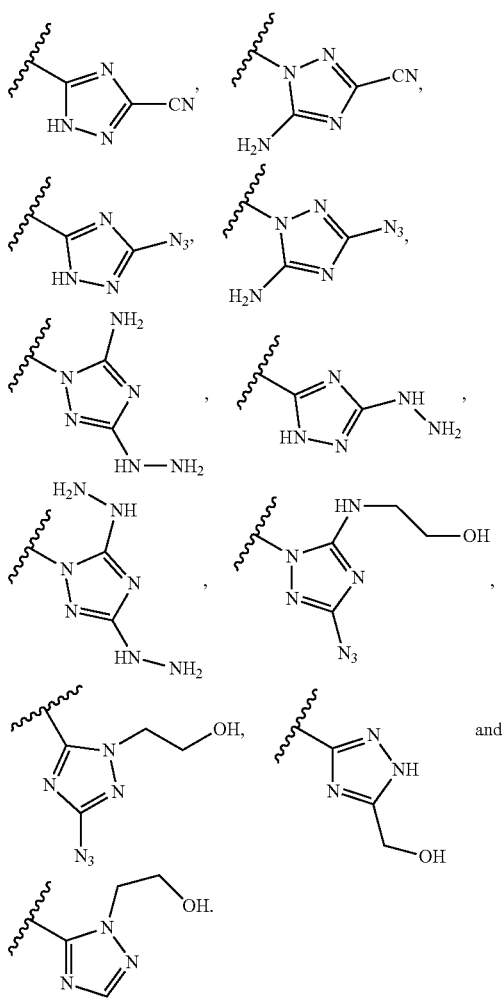

6. The mixture of claim 1, wherein said tetrazole moiety is represented by a formula selected from the group consisting of:

Formula VI

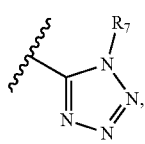

Formula VII

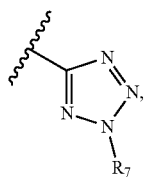

Formula VIII and

Formula IX

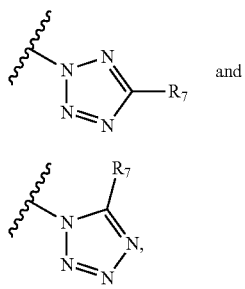

wherein R7 is said polymerizable group.

7. The mixture of claim 6, wherein said tetrazole moiety is selected from the group consisting of:

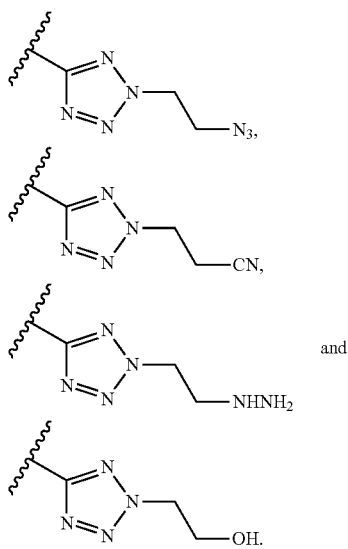

8. The mixture of claim 1, wherein said first monomer is selected from the group consisting of:

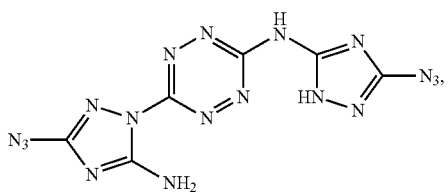

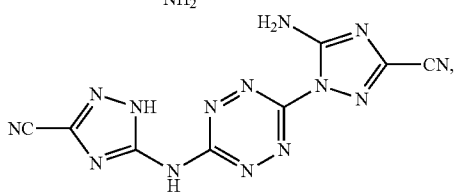

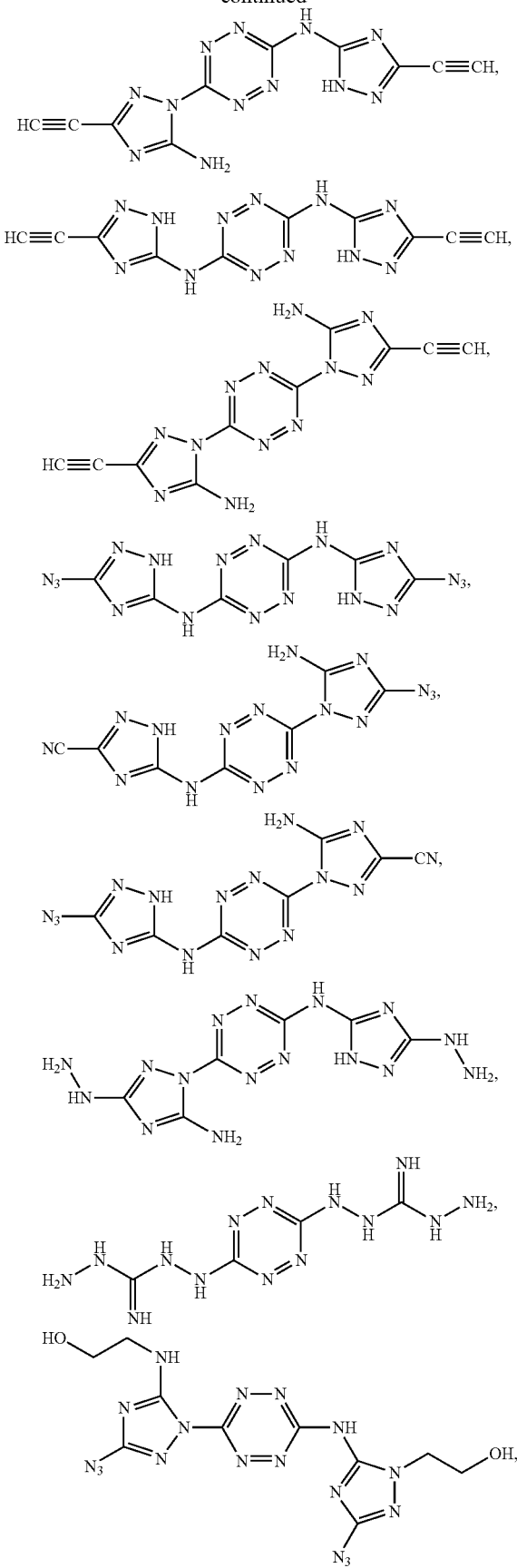
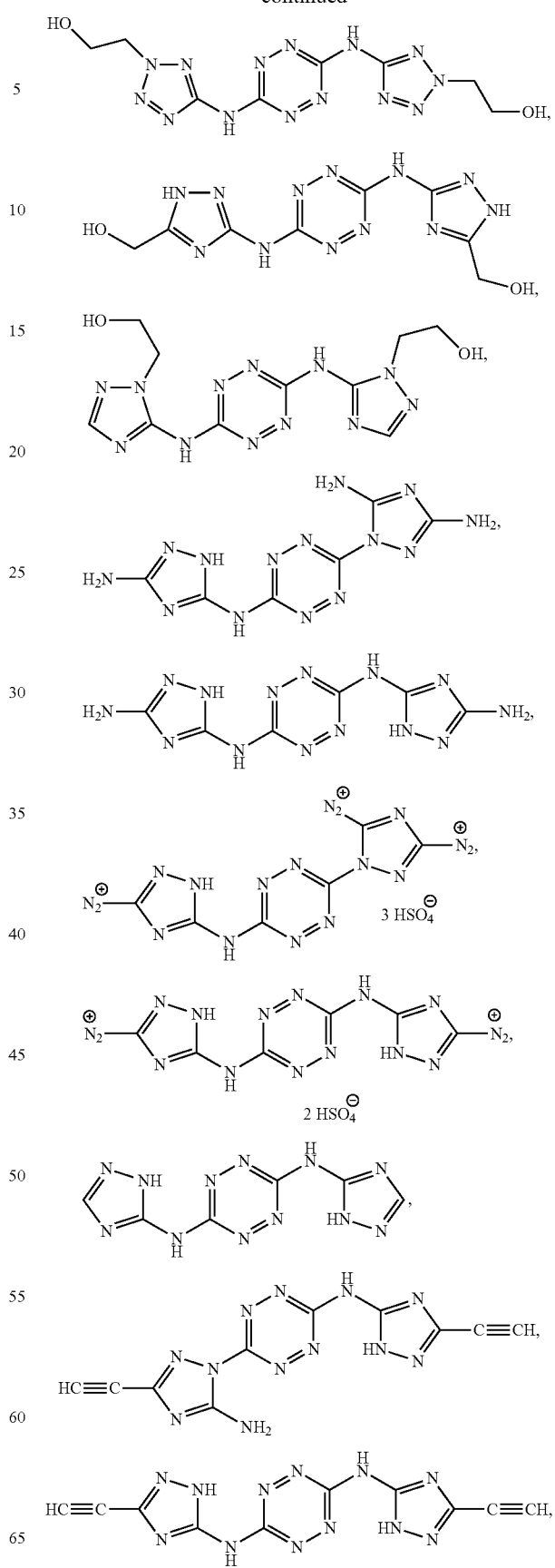

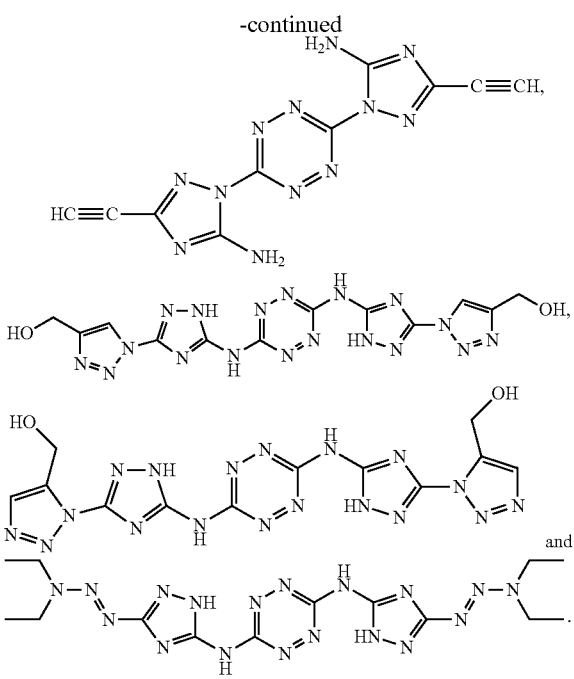

9. The mixture of claim 1, further comprising a second monomer represented by Formula X:

R$_8$—A—R$_9$    Formula X;

wherein:

A is selected from the group consisting of C$_{1-6}$ alkyl, cycloalkyl, heteroalicyclic, aryl and heteroaryl, and each of R8 and R9 is independently a polymerizable group selected from the group consisting of azido, cyano, diazonium, ethynyl, hydrazine, hydroxyl, hydrazide, amine, ethanolamine, isocyanate, cyanate, amide, imidate, ester, carboxyl and azo.

10. The mixture of claim 9, wherein said second monomer is selected from the group consisting of 1,6-diisocyanato-hexane, 1,4-dicyanobutane (adiponitrile) and dimethyl adipimidate.

11. The mixture of claim 1, wherein said second monomer is a silane represented by Formula XI:

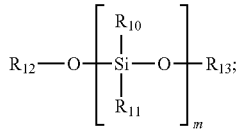

Formula XI wherein:

m is an integer ranging from 1 to 4 ; and each of R10 and R11 is independently selected from the group consisting of H, C$_{1-4}$ alkyl, C$_{1-4}$ alkenyl, aryl, heterocyclic and heteroaryl; and each of R12 and R13 is independently selected from the group consisting of H, a silane, C$_{1-4}$ alkyl and C$_{1-4}$ alkenyl.

12. The mixture of claim 11, wherein m is 1, and each of R10, R11, R12 and R13 is independently and C$_{1-4}$ alkyl.

13. The mixture of claim 12, wherein said silane is selected from the group consisting of dimethoxydimethyl-silane and diethoxydimethylsilane.

14. A polymer derived from the mixture of monomers of claim 1 such that at least a portion of the backbone units of the polymer are derived from said first monomer and said second monomer.

15. An article of manufacturing comprising the polymer of claim 14.

16. The article of claim 15, forming a part of a system selected from the group consisting of a fire extinguishing system, a safety airbag, an inflatable device, a buoy, a flotation device, a liquid nebulizer, a powder deployment device, a pneumatic actuator, a gas supply device and a valve actuator.

* * * * *